US012653835B2

(12) United States Patent
(10) Patent No.: US 12,653,835 B2
(45) Date of Patent: Jun. 16, 2026

Kasibhatla et al.

(54) PHOSPHONATES AS INHIBITORS OF ENPP1 AND CDNP

(71) Applicant: STINGRAY THERAPEUTICS, INC., Houston, TX (US)

(72) Inventors: Srinivas Rao Kasibhatla, San Diego, CA (US); Sunil Sharma, Phoenix, AZ (US); Mohan Kaadige, Scottsdale, AZ (US); Alexis Weston, Phoenix, AZ (US); Trason Thode, Phoenix, AZ (US)

(73) Assignee: STINGRAY THERAPEUTICS, INC., Houston, TX (US)

( * ) Notice: Subject to any disclaimer, the term of this patent is extended or adjusted under 35 U.S.C. 154(b) by 472 days.

(21) Appl. No.: 18/254,753

(22) PCT Filed: Dec. 8, 2021

(86) PCT No.: PCT/US2021/062328

§ 371 (c)(1),
(2) Date: May 26, 2023

(87) PCT Pub. No.: WO2022/125613

PCT Pub. Date: Jun. 16, 2022

(65) Prior Publication Data

US 2025/0099493 A1 Mar. 27, 2025

Related U.S. Application Data

(60) Provisional application No. 63/123,304, filed on Dec. 9, 2020, provisional application No. 63/123,287, filed on Dec. 9, 2020.

(51) Int. Cl.

| | |
|---|---|
| *A61K 31/675* | (2006.01) |
| *A61K 9/00* | (2006.01) |
| *A61K 9/20* | (2006.01) |
| *C07F 9/6558* | (2006.01) |

(52) U.S. Cl.

CPC .......... *A61K 31/675* (2013.01); *A61K 9/0053* (2013.01); *A61K 9/2013* (2013.01); *A61K 9/2018* (2013.01); *A61K 9/2054* (2013.01); *A61K 9/2059* (2013.01); *C07F 9/65583* (2013.01)

(58) Field of Classification Search

CPC .. A61K 31/675; A61K 9/0053; A61K 9/2013; A61K 9/2018; A61K 9/2054; A61K 9/2059; C07F 9/65583

See application file for complete search history.

(56) References Cited

U.S. PATENT DOCUMENTS

2022/0056052 A1 * 2/2022 Hawley ............... C07F 9/65583

FOREIGN PATENT DOCUMENTS

WO WO-2020160333 A1 * 8/2020 .......... C07F 9/65583

* cited by examiner

*Primary Examiner* — Savitha M Rao

(74) *Attorney, Agent, or Firm* — Seed IP Law Group LLP

(57) ABSTRACT

Compounds having activity as inhibitors of ENPP1, CdnP, or both are provided herein. Some embodiments provide compounds having one of the following Structures (I) or (II): or a pharmaceutically acceptable salt, tautomer, stereoisomer, or prodrug thereof, wherein $R^1$, $R^2$, $R^3$, $R^4$, $R^5$, $R^6$, $R^{7a}$, $R^{7b}$, $R^{7b}$, $R^{7c}$, $R^{25}$, $R^{26}$, $R^{27a}$, $R^{27b}$, $R^{27c}$, $L^1$, $L^5$, $L^6$, $G^1$, $G^2$, $G^3$ and $G^6$ are as defined herein. This disclosure provides methods associated with preparation and use of such compounds, pharmaceutical compositions comprising such compounds, and methods for treating disorders associated with ENPP1, including uncontrolled cellular proliferation, cancer and virial or bacterial infections in a mammal.

(I)

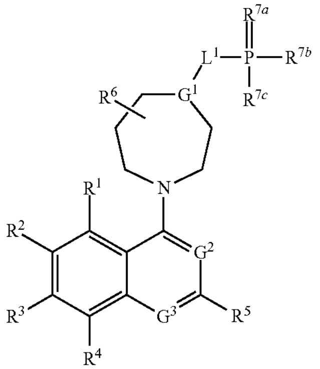

(II)

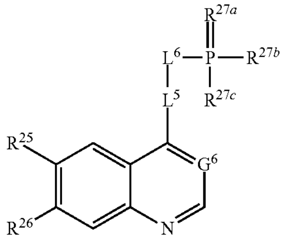

6 Claims, No Drawings

PHOSPHONATES AS INHIBITORS OF ENPP1 AND CDNP

BACKGROUND

Technical Field

Embodiments of the present disclosure are generally directed to compounds and methods for their preparation and use as therapeutic or prophylactic agents, for example for treatment of mycobacterial infections, and/or cancers (e.g., solid tumors, breast cancer, leukemia, lymphoma).

Description of the Related Art

Ectonucleotide Pyrophophatase/Phosphodiesterase (ENPP) family members include seven isoforms, ENPP1-7, which are type II transmembrane glycoproteins or ectoenzymes. Mass spectrometry and proteomics analysis from more than 370 protein targets led to the identification of an extracellular protein ENPP1 as one of the top hit which exhibited high hydrolytic activity. ATP is an identified substrate of ENPP1, which is hydrolyzed to AMP and PPi. CD73 converts AMP to adenosine and inorganic phosphate (Pi). The kinetic experimental data indicates that the ENPP1 is capable of hydrolyzing ATP. These ectonucleotide enzymes are involved in the hydrolysis of pyrophosphate (PPi) and phosphodiester bonds in extracellular nucleotides; such as triphosphates, oligonucleotides and that generates nucleoside 5'-monophosphates. One of the key isoforms, ENPP1 (Plasma cell membrane glycoprotein-1, PC-1), is involved in a number of physiological processes, such as development, formation and trafficking, as well as in pathophysiological conditions. Aberrant ENPP1 expression has been detected in breast cancers relative to normal mammary epithelium, an evidence of its potential in the development of bone metastasis (occurs in approximately 80% cases), Hodgkin's lymphoma, hepatocellular carcinoma, follicular lymphoma, glioblastoma and in other malignant tumor tissues. Furthermore, ENPP1 activity has also been implicated in diseases caused by bacteria and/or viruses, and therefore modulators of ENPP1 can be used to treat bacterial and/or viral diseases and conditions.

*M. tuberculosis* is a stubborn pathogen with the ability to subvert the host cell's defense response and successfully survive within the infected cell. It has evolved several mechanisms to evade host immune system and one such mechanism is subversion of host signaling molecules, particularly nucleotide second messengers. CdnP degrades both bacterial (c-di-AMP) and host (2'3'-cGAMP) CDNs and thus serve as a dual function protein by preventing host-recognition of bacterial CDN as well as degrading host 2'3'-cGAMP. The virulence of a CdnP-disrupted *M. tuberculosis* strain was shown to be substantially dampened when compared with the wild type strain in a mouse model and mice infected with the mutant strain lived 6 months longer than mice infected with the wild type strain. This suggests that CdnP could be a therapeutic target for *M. tuberculosis* treatment. It has been shown that pA(S)A, an analog of the intermediate linear dinucleotide pApA substrate, inhibits CdnP activity and potentiates CDN signaling. However, because of poor permeability, these analogs showed moderate effects in the context of cellular infectivity with *M. tuberculosis*. CdnP shares a predicted homology with the host ENPP1, an enzyme that specifically degrades the host 2'3'-cGAMP and blocks activation of the STING signaling pathway. ENPP1, like CdnP, can cleave the bacterial c-di-AMP but at a slower rate and deletion of ENPP1 inhibits the growth of *M. tuberculosis* in infected cells. Thus, both CdnP and ENPP1 appear to play an important role in promoting virulence and intracellular microbial survival by destroying the bacterial and host CDN ligands necessary for the activation of STING-IRF3-IFN pathway. Inhibiting bacterial CdnP or host ENPP1 or both may be an attractive therapeutic strategy to fight mycobacterial infections.

Accordingly, there is need for improved inhibitors of ENPP1, CdnP, or both, and use of the same to treat various diseases. The present disclosure provides these and related advantages.

BRIEF SUMMARY

In brief, embodiments of the present disclosure provide compounds, including pharmaceutically acceptable salts, stereoisomers, and tautomers thereof having activity as inhibitors of ENPP1, CdnP, or both. One embodiment provides compounds having the following Structure (I):

(I)

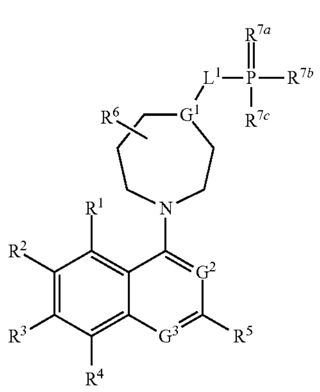

or a pharmaceutically acceptable salt, tautomer, stereoisomer, or prodrug thereof, wherein $R^1$, $R^2$, $R^3$, $R^4$, $R^5$, $R^6$, $R^{7a}$, $R^{7b}$, $R^{7b}$, $R^{7c}$, $L^1$, $G^1$, $G^2$, and $G^3$ are as defined herein. Another embodiment provides pharmaceutical compositions comprising one or more compounds of Structure (I) and a pharmaceutically acceptable carrier or excipient.

Other embodiments of the present disclosure provide compounds, including pharmaceutically acceptable salts, stereoisomers, and tautomers thereof having activity as inhibitors of ENPP1, CdnP, or both. One embodiment provides compounds have the following Structure (II):

(II)

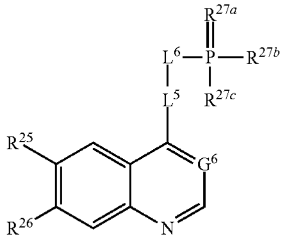

or a pharmaceutically acceptable salt, tautomer, stereoisomer, or prodrug thereof, wherein $R^{25}$, $R^{26}$, $R^{27a}$, $R^{27b}$, $R^{27c}$, $L^5$, $L^6$ and $G^6$ are as defined herein. Another embodiment provides pharmaceutical compositions comprising one or more compounds of Structure (II) and a pharmaceutically acceptable carrier or excipient.

One specific embodiment provides a method for treating a mycobacterial infection comprising administering a pharmaceutical composition comprising a pharmaceutically acceptable carrier, diluent, or excipient and a compound having the following Structure (III).

(III)

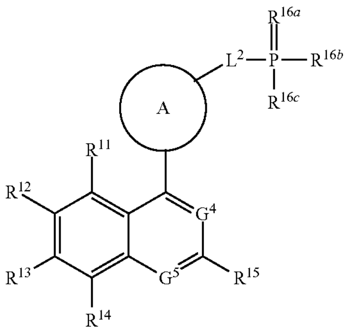

or a stereoisomer, tautomer, or pharmaceutically acceptable salt thereof, wherein:

$R^{11}$, $R^{12}$, $R^{13}$, $R^{14}$, $R^{15}$, $R^{16a}$, $R^{16b}$, $R^{16c}$, $G^4$, $G^5$, $L^2$ and A are as defined herein.

In yet another embodiment of the present disclosure, a method of treatment for a disease or disorder (e.g., mycobacterial infection or cancer) is provided, the method comprising administering to a mammal an effective amount of a compound of Structure (I), (II), or (III). These and other aspects of the disclosure will be apparent upon reference to the following detailed description.

DETAILED DESCRIPTION

In the following description, certain specific details are set forth in order to provide a thorough understanding of various embodiments of the disclosure. However, one skilled in the art will understand that the disclosure may be practiced without these details.

Unless the context requires otherwise, throughout the present specification and claims, the word "comprise" and variations thereof, such as, "comprises" and "comprising" are to be construed in an open, inclusive sense, that is, as "including, but not limited to".

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size, or thickness, are to be understood to include any integer within the recited range, unless otherwise indicated. As used herein, the terms "about" and "approximately" mean ±20%, ±10%, ±5% or ±1% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives.

Reference throughout this specification to "one embodiment" or "an embodiment" means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Unless defined otherwise, all technical and scientific terms used herein have the same meaning as is commonly understood by one of skill in the art to which this disclosure belongs. As used in the specification and claims, the singular form "a", "an" and "the" include plural references unless the context clearly dictates otherwise.

"Amino" refers to the $—NH_2$ radical.

"Carboxy" or "carboxyl" refers to the $—CO_2H$ radical.

"Cyano" refers to the —CN radical.

"Hydroxy" or "hydroxyl" refers to the —OH radical.

"Oxo" refers to the =O substituent.

"Nitro" refers to the $—NO_2$ radical.

"Thiol" or "thio" refers to the —SH substituent.

"Carbonyl" refers to a —C(=O)— moiety.

"Alkyl" refers to a saturated, straight or branched hydrocarbon chain radical consisting solely of carbon and hydrogen atoms, having, for example, from one to twelve carbon atoms ($C_1$-$C_{12}$ alkyl), one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl and the like. Unless stated otherwise specifically in the specification, an alkyl group is optionally substituted.

"Alkylene" or "alkylene chain" refers to a straight or branched divalent hydrocarbon chain linking the rest of the molecule to a radical group, consisting solely of carbon and hydrogen, which is saturated and having, for example, from one to twenty-four carbon atoms ($C_1$-$C_{24}$ alkylene), one to fifteen carbon atoms ($C_1$-$C_{15}$ alkylene), one to twelve carbon atoms ($C_1$-$C_{12}$ alkylene), one to eight carbon atoms ($C_1$-$C_8$ alkylene), one to six carbon atoms ($C_1$-$C_6$ alkylene), two to four carbon atoms ($C_2$-$C_4$ alkylene), one to two carbon atoms ($C_1$-$C_2$ alkylene), e.g., methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula $—OR_a$ where $R_a$ is an alkyl radical as defined above containing one to twelve carbon atoms ($C_1$-$C_{12}$ alkoxy), one to eight carbon atoms ($C_1$-$C_8$ alkoxy) or one to six carbon atoms ($C_1$-$C_6$ alkoxy), or any value within these ranges. Unless stated otherwise specifically in the specification, an alkoxy group is optionally substituted.

"Alkylcarbonyl" refers to a radical of the formula $—R_aR_b$ wherein $R_a$ is a carbonyl as defined above and $R_b$ is alkyl as defined above. Unless stated otherwise specifically in the specification, an alkylcarbonyl group is optionally substituted.

"Aminyl" refers to a radical of the formula $—NR_aR_b$ wherein $R_a$ is alkyl as defined above and $R_b$ is hydrogen or alkyl as defined above. Unless stated otherwise specifically in the specification, an aminyl group is optionally substituted.

"Aminylalkyl" refers to a radical of the formula —$R_aNR_bR_c$ where $R_a$ and $R_b$ are each independently an alkyl as defined above, $R_b$ is H or alkyl as defined above. Unless stated otherwise specifically in the specification, an aminylalkyl group is optionally substituted.

"Aminylalkylene" refers to a radical of the formula —$NR_aR_b$ where $R_a$ is alkylene as defined above, $R_b$ is H or alkyl as defined above. Unless stated otherwise specifically in the specification, an aminylalkylene group is optionally substituted.

"Aminylcarbonyl" refers to a radical of the formula —$R_aNR_bR_c$ where $R_a$ is a carbonyl as defined above, $R_b$ is an alkyl as defined above, and $R_c$ is H or alkyl as defined above. Unless stated otherwise specifically in the specification, an aminylcarbonyl group is optionally substituted.

"Aminylcarbonylalkyl" refers to a radical of the formula —$R_aR_bNR_cR_a$ where $R_a$ is alkyl as defined above, $R_b$ is a carbonyl as defined above, $R_c$ is an alkyl as defined above, and Rd is H or alkyl as defined above. Unless stated otherwise specifically in the specification, an aminylcarbonylalkyl group is optionally substituted.

"Aromatic ring" refers to a cyclic planar portion of a molecule (i.e., a radical) with a ring of resonance bonds that exhibits increased stability relative to other connective arrangements with the same sets of atoms. Generally, aromatic rings contains a set of covalently bound co-planar atoms and comprises a number of 7-electrons (for example, alternating double and single bonds) that is even but not a multiple of 4 (i.e., 4n+2 π-electrons, where n=0, 1, 2, 3, etc.). Aromatic rings include, but are not limited to, phenyl, naphthenyl, imidazolyl, pyrrolyl, pyridinyl, pyrimidinyl, pyrazinyl, pyridonyl, pyridazinyl, pyrimidonyl. Unless stated otherwise specifically in the specification, an "aromatic ring" includes all radicals that are optionally substituted.

"Aryl" refers to a carbocyclic ring system (i.e., a ring system wherein each ring atom is carbon) radical comprising 6 to 18 carbon ring atoms and at least one aromatic ring. For purposes of embodiments of this disclosure, the aryl radical is a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

Addition of the suffix "-ene" implies the modification of a radical group to a divalent or multivalent group. For example the term "arylene" refers to a divalent or multivalent aryl group as defined above that links a portion of a molecule to a radical group, two or more radical groups, or a portion of a first molecule to a portion of a second molecule.

"Arylalkyl" or "aralkyl" refers to a radical of the formula —$R_bR_f$ where $R_b$ is an alkylene chain as defined above and $R_f$ is an aryl radical as defined above. Unless stated otherwise specifically in the specification, an alkylaryl group is optionally substituted.

"Aryloxy" refers to a radical of the formula —$OR_b$ where $R_b$ is an aryl group as defined above. The aryl part of the aryloxy radical may be optionally substituted as defined above.

"Cycloalkyl" refers to a stable non-aromatic monocyclic or polycyclic carbocyclic radical, which may include fused or bridged ring systems, having from three to fifteen carbon atoms, preferably having from three to ten carbon atoms, and which is saturated or partially unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group is optionally substituted.

"Fused" refers to any ring structure described herein which is fused to an existing ring structure in the compounds of the disclosure. When the fused ring is a heterocyclyl ring or a heteroaryl ring, any carbon atom on the existing ring structure that becomes part of the fused heterocyclyl ring or the fused heteroaryl ring is replaced with a nitrogen atom.

"Halo" or "halogen" refers to bromo (Br), chloro (Cl), fluoro (F) or iodo (I).

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group is optionally substituted.

"Heterocyclyl" or "heterocyclic ring" refers to a stable 3- to 18-membered non-aromatic ring radical having one to twelve ring carbon atoms (e.g., two to twelve) and from one to six ring heteroatoms selected from the group consisting of nitrogen, oxygen and sulfur. Unless stated otherwise specifically in the specification, the heterocyclyl radical is a monocyclic, bicyclic, tricyclic or tetracyclic ring system, which may include fused, spirocyclic ("spiro-heterocyclyl") and/or bridged ring systems; and the nitrogen, carbon or sulfur atoms in the heterocyclyl radical is optionally oxidized; the nitrogen atom is optionally quaternized; and the heterocyclyl radical is partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,2,3,4-tetrahydroquinolinyl, and 1,1-dioxo-thiomorpholinyl. Unless stated otherwise specifically in the specification, a heterocyclyl group is optionally substituted.

"Hydroxyalkyl" refers to an alkyl group comprising at least one hydroxyl substituent. The —OH substituent may be on a primary, secondary or tertiary carbon.

Unless stated otherwise specifically in the specification, a hydroxyalkyl group is optionally substituted.

"Heteroaryl" refers to a 5- to 18-membered, for example 5- to 6-membered, ring system radical comprising one to thirteen ring carbon atoms, one to six ring heteroatoms selected from the group consisting of nitrogen, oxygen and sulfur, and at least one aromatic ring. Heteroaryl radicals may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group is optionally substituted.

"Haloalkoxy" refers to a radical of the formula —$OR_a$ where $R_a$ is a haloalkyl radical as defined herein containing one to twelve carbon atoms. Unless stated otherwise specifically in the specification, a haloalkoxy group is optionally substituted.

"Heterocyclylalkyl" refers to a radical of the formula —$R_bR_c$ where $R_b$ is an alkylene chain as defined above and $R_c$ is a heterocyclyl radical as defined above, and if the heterocyclyl is a nitrogen-containing heterocyclyl, the heterocyclyl is optionally attached to the alkyl radical at the nitrogen atom. Unless stated otherwise specifically in the specification, a heterocyclylalkyl group is optionally substituted.

"Heteroarylalkyl" refers to a radical of the formula —$R_bR_f$ where $R_b$ is an alkylene chain as defined above and $R_f$ is a heteroaryl radical as defined above. Unless stated otherwise specifically in the specification, a heteroarylalkyl group is optionally substituted. The term "substituted" as used herein means any of the above groups wherein at least one hydrogen atom (e.g., 1, 2, 3 or all hydrogen atoms) is replaced by a bond to a non-hydrogen substituent. Examples of non-hydrogen substituents include, but are not limited to: amino, carboxyl, cyano, hydroxyl, halo, nitro, oxo, thiol, thioxo, alkyl, alkenyl, alkylcarbonyl, alkoxy, aryl, cyanoalkyl, cycloalkyl, haloalkyl, heterocyclyl, heterocyclylalkyl, heteroaryl, heteroarylalkyl and/or hydroxylalkyl substituents, each of which may also be optionally substituted with one or more of the above substituents.

In some embodiments, the optional substituents are selected from the group consisting of amino, carboxyl, cyano, halo, hydroxyl, $C_{1-6}$ alkyl, $C_{1-6}$ alkylamino, $C_{1-6}$ haloalkyl, $C_{1-6}$ alkylcarbonyl, $C_{1-6}$ alkoxy, $C_{1-6}$ haloalkoxy, $C_{1-6}$ alkoxycarbonyl, $C_6$-$C_{10}$ aryl and $C_6$-$C_{10}$ heteroaryl.

It is understood that each choice for $R^1$, $R^2$, $R^3$, $R^4$, $R^5$, $R^6$, $R^{7a}$, $R^{7b}$, $R^{7b}$, $R^{7c}$, $L^1$, $G^1$, $G^2$, and $G^3$ is optionally substituted as described above unless specifically stated otherwise, and provided that all valences are satisfied by the substitution. Specifically, each choice for $R^1$, $R^2$, $R^3$, $R^4$, $R^5$, $R^6$, $R^{7a}$, $R^{7b}$, $R^{7b}$, $R^{7c}$, $L^1$, $G^1$, $G^2$, and $G^3$ is optionally substituted unless specifically stated otherwise, and provided such substitution results in a stable molecule (e.g., groups such as H and halo are not optionally substituted).

As used herein, the term "ENPP1" refers to ectonucleotide pyrophophatase/phosphodiesterase 1.

As used herein, the term "CdnP" refers to cyclic dinucleotide phosphodiesterase.

The term "effective amount" or "therapeutically effective amount" refers to that amount of a compound described herein that is sufficient to effect the intended application including but not limited to disease treatment, as defined below. The therapeutically effective amount may vary depending upon the intended treatment application (in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment" or "treating" refer to an approach for obtaining beneficial or desired results with respect to a disease, disorder or medical condition including but not limited to a therapeutic benefit and/or a prophylactic benefit. "Therapeutic benefit" means eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, encompass administration of two or more agents to an animal, including humans, so that both agents and/or their metabolites are present in the subject at the same time. Co-administration includes simultaneous administration in separate compositions, administration at different times in separate compositions, or administration in a composition in which both agents are present.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

"Subject" refers to an animal, such as a mammal, for example a human. The methods described herein can be useful in both human therapeutics and veterinary applications. In some embodiments, the subject is a mammal, and in some embodiments, the subject is human. The term does not denote a particular age or sex. Thus, adult and newborn subjects, as well as fetuses, whether male or female, are intended to be covered. "Mammal" includes humans and both domestic animals such as laboratory animals and household pets (e.g., cats, dogs, swine, cattle, sheep, goats, horses, rabbits), and non-domestic animals such as wildlife and the like.

A patient refers to a subject afflicted with a disease or disorder. The term "patient" includes human and veterinary subjects. In some aspects of the disclosed methods, the subject has been diagnosed with a need for treatment of a disorder of uncontrolled cellular proliferation associated with an ENPP1 dysfunction prior to the administering step. In some aspects of the disclosed method, the subject has been diagnosed with a need for inhibition of ENPP1 prior to the administering step.

Prodrugs of the disclosed compounds are included in various embodiments. "Prodrug" is meant to indicate a compound that may be converted under physiological conditions or by solvolysis to a biologically active compound described herein (e.g., compound of structure (I)). Thus, the term "prodrug" refers to a precursor of a biologically active compound that is pharmaceutically acceptable. In some aspects, a prodrug is inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" includes any covalently bonded carriers, which release the active compound in vivo when such prodrug is administered to a mammalian subject. Prodrugs of an active compound, as described herein, are typically prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of a hydroxy functional group, or acetamide, formamide and benzamide derivatives of an amine functional group in the active compound and the like.

The term "in vivo" refers to an event that takes place in a subject's body.

Embodiments disclosed herein are also meant to encompass all pharmaceutically acceptable compounds of Structure (I), (II), or (III) being isotopically-labelled by having one or more atoms replaced by an atom having a different atomic mass or mass number (i.e., an "isotopic form" of a compound of Structure (I), (II), or (III)). Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabeled compounds could be useful to help determine or measure the effectiveness of the compounds, by characterizing, for example, the site or mode of action, or binding affinity to pharmacologically important site of action. Certain isotopically labeled compounds of Structure (I), (II), or (III), for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e., $^{2}H$, may afford certain therapeutic advantages resulting from greater metabolic stability, for example, increased in vivo half-life or reduced dosage requirements, and hence are preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of Structure (I), (II), or (III) can generally be prepared by conventional techniques known to those skilled in the art or by processes analogous to those described in the Examples as set out below using an appropriate isotopically-labeled reagent in place of the non-labeled reagent previously employed.

Certain embodiments are also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the embodiments include compounds produced by a process comprising administering a compound of this disclosure to a mammal for a period of time sufficient to yield a metabolic product thereof. Such products are typically identified by administering a radiolabeled compound of the disclosure in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

Often crystallizations produce a solvate of the compound of the disclosure. As used herein, the term "solvate" refers to an aggregate that comprises one or more molecules of a compound of the disclosure with one or more molecules of solvent. In some embodiments, the solvent is water, in which case the solvate is a hydrate. Alternatively, in other embodiments, the solvent is an organic solvent. Thus, the compounds of Structure (I), (II), or (III) may exist as a hydrate, including a monohydrate, dihydrate, hemihydrate, sesquihydrate, trihydrate, tetrahydrate and the like, as well as the corresponding solvated forms. In some aspects, the compound of the disclosure is a true solvate, while in other cases, the compound of the disclosure merely retains adventitious water or is a mixture of water plus some adventitious solvent.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

A "pharmaceutical composition" refers to a formulation of a compound of the disclosure and a medium generally accepted in the art for the delivery of the biologically active compound to mammals, e.g., humans. Such a medium includes all pharmaceutically acceptable carriers, diluents or excipients therefor.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

The compounds of the disclosure (i.e., compounds of Structure (I), (II), or (III) and embodiments thereof), or their pharmaceutically acceptable salts may contain one or more centers of geometric asymmetry and may thus give rise to enantiomers, diastereomers, and other stereoisomeric forms that are defined, in terms of absolute stereochemistry, as (R)- or (S)- or, as (D)- or (L)- for amino acids. Embodiments thus include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also included.

The present disclosure includes all manner of rotamers and conformationally restricted states of a compound of the disclosure.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another. Unless otherwise indicated, stereoisomers include racemers, enantiomers and diastereomers.

A "tautomer" refers to a proton shift from one atom of a molecule to another atom of the same molecule. Embodiments thus include tautomers of the disclosed compounds.

The chemical naming protocol and structure diagrams used herein are a modified form of the I.U.P.A.C. nomenclature system, using the ACD/Name Version 9.07 software program and/or ChemDraw Ultra Version 11.0.1 software naming program (CambridgeSoft). For complex chemical names employed herein, a substituent group is typically named before the group to which it attaches. For example, cyclopropylethyl comprises an ethyl backbone with a cyclopropyl substituent. Except as described below, all bonds are identified in the chemical structure diagrams herein, except for all bonds on some carbon atoms, which are assumed to be bonded to sufficient hydrogen atoms to complete the valency.

Compounds

As detailed above, the present disclosure provides compounds having activity as ENPP1 inhibitors, CdnP inhibitors, or both.

In an embodiment, the compounds are useful in the treatment of disorders of uncontrolled cellular proliferations. In a further embodiment, the disorder of uncontrolled cellular proliferation is a cancer or a tumor. In still another embodiment, the disorder of uncontrolled cellular proliferation is associated with an ENPP1 dysfunction, as further described herein.

In another embodiment, the compounds are useful in the treatment of diseases of bacterial or viral origin (e.g., diseases mediated by CdnP). Accordingly, the disclosure provides a method of treating a disease caused by bacteria or viruses, comprising administering to a subject a therapeutically effective amount of a compound of the present disclosure, or a composition derived therefrom.

Accordingly, one embodiment provides a compound having the following structure (I):

(I)

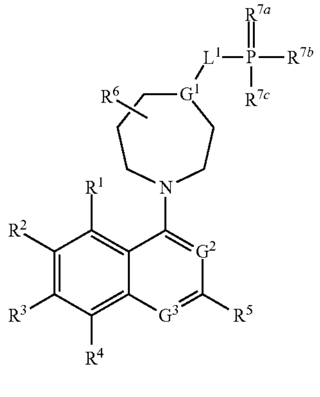

or a stereoisomer, tautomer, or pharmaceutically acceptable salt thereof, wherein:

$G^1$ is N or CH;

$G^2$ is N or $CR^9$;

$G^3$ is N or $CR^{10}$;

$L^1$ is a direct bond, $C_1$-$C_6$ alkylene, or $C_1$-$C_6$ aminylalkylene, provided that $L^1$ is a direct bond only if $G^1$ is CH;

$R^1$, $R^2$, $R^3$, $R^4$, $R^5$, $R^9$ and $R^{10}$ are each independently hydrogen, alkyl, halo, hydroxy, cyano, haloalkyl, alkoxy, haloalkoxy, hydroxyalkyl, aminylcarbonylalkyl, or aminylalkyl, aminylcarbonyl, aminyl, alkylcarbonyl, —C(═O)Oalkyl, heterocyclyl, or heteroaryl;

$R^6$ is hydrogen, alkyl, halo, hydroxy, cyano, haloalkyl, alkoxy, haloalkoxy, or hydroxyalkyl;

$R^{7a}$ is O or S;

$R^{7b}$ and $R^{7c}$ are each independently —$O^-$, —OH, —$S^-$, —SH, or —$NR^{8a}R^{8b}$; and $R^{8a}$ and $R^{8b}$ are, at each occurrence, independently hydrogen or alkyl.

In some embodiments, $G^1$ is N. In certain embodiments, $G^2$ is CH. In some more specific embodiments, $G^2$ is $CR^9$. In certain more specific embodiments, $R^9$ is hydrogen or cyano. In some embodiments, $G^2$ is N. In certain embodiments, $G^3$ is $CR^{10}$. In some specific embodiments, $G^3$ is CH. In certain specific embodiments, $G^3$ is N.

In certain embodiments, $R^1$, $R^2$, $R^3$, $R^4$, and $R^5$ are each independently hydrogen, halogen, hydroxy, alkoxy, aminylcarbonyl, aminyl, —C(═O)Oalkyl, or a 5-6 membered heteroaryl. In more specific embodiments, $R^1$ is hydrogen or alkoxy. In some embodiments, $R^1$ is hydrogen or methoxy.

In some embodiments, $R^2$ is hydrogen or alkoxy. In certain embodiments, $R^2$ is hydrogen or methoxy.

In some specific embodiments, $R^3$ is hydrogen or alkoxy. In certain specific embodiments, $R^3$ is hydrogen or methoxy.

In some more specific embodiments, $R^4$ is hydrogen or alkoxy. In certain more specific embodiments, $R^4$ is hydrogen or methoxy.

In some embodiments, $R^5$ is hydrogen. In certain embodiments, $R^6$ is hydrogen.

In certain embodiments, $R^{7a}$ is O. In some more specific embodiments, $R^{7b}$ —$O^-$ or —OH. In certain embodiments, $R^{7c}$ —$O^-$ or —OH.

In some specific embodiments, $L^1$ is $C_1$-$C_6$ alkylene optionally substituted with oxo. In certain specific embodiments, $L^1$ is unsubstituted methylene. In some more specific embodiments, $L^1$ is unsubstituted ethylene. In some embodiments, $L^1$ is unsubstituted propylene.

In some more specific embodiments of the compound of Structure (I), the compound is selected from Table 1A, below. In any one of the foregoing embodiments, a stereoisomer, tautomer, prodrug, or pharmaceutically acceptable salt thereof is also included.

TABLE 1A

Representative compounds of Structure (I)

| Cmpd. No. | Structure | Name |
|---|---|---|
| I-1 | 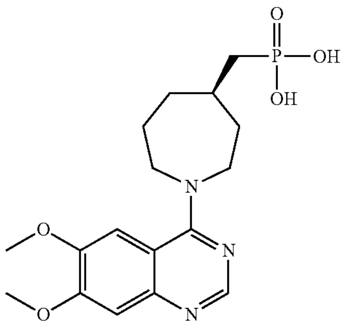 [SMILES: COc1cc2ncnc(N3CCC[C@@H](CP(=O)(O)O)CC3)c2cc1OC] | (R)-((1-(6,7-dimethoxyquinazolin-4-yl)azepan-4-yl)methyl)phosphonic acid |
| I-2 | 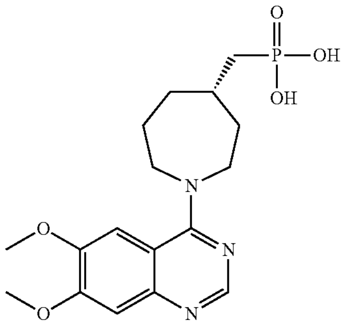 [SMILES: COc1cc2ncnc(N3CCC[C@H](CP(=O)(O)O)CC3)c2cc1OC] | (S)-((1-(6,7-dimethoxyquinazolin-4-yl)azepan-4-yl)methyl)phosphonic acid |

TABLE 1A-continued
| Representative compounds of Structure (I) | | |
|---|---|---|
| Cmpd. No. | Structure | Name |
| I-3 | 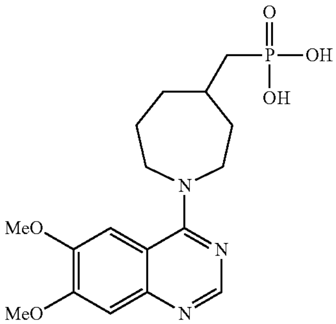 [SMILES: COc1cc2ncnc(N3CCCC(CP(=O)(O)O)CC3)c2cc1OC] | ((1-(6,7-dimethoxyquinazolin-4-yl)azepan-4-yl)methyl)phosphonic acid |
| I-4 | 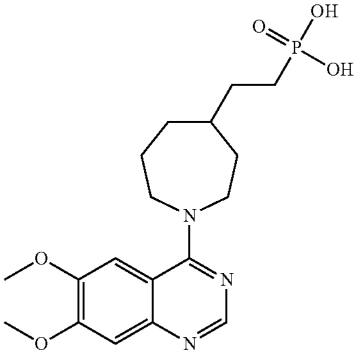 [SMILES: COc1cc2ncnc(N3CCCC(CCP(=O)(O)O)CC3)c2cc1OC] | (2-(1-(6,7-dimethoxyquinazolin-4-yl)azepan-4-yl)ethyl)phosphonic acid |
| I-5 | 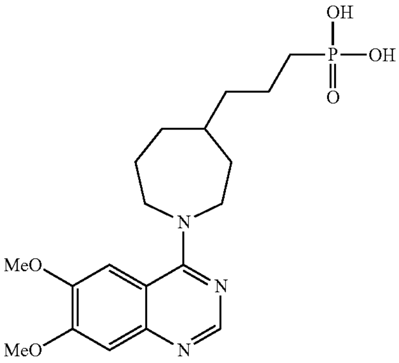 [SMILES: COc1cc2ncnc(N3CCCC(CCCP(=O)(O)O)CC3)c2cc1OC] | (3-(1-(6,7-dimethoxyquinazolin-4-yl)azepan-4-yl)propyl)phosphonic acid |
| I-6 | 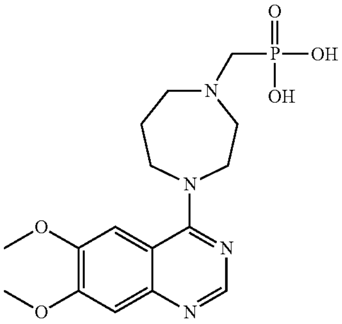 [SMILES: COc1cc2ncnc(N3CCCN(CP(=O)(O)O)CC3)c2cc1OC] | ((4-(6,7-dimethoxyquinazolin-4-yl)-1,4-diazepan-1-yl)methyl)phosphonic acid |

TABLE 1A-continued

Representative compounds of Structure (I)

| Cmpd. No. | Structure | Name |
|---|---|---|
| I-7 | 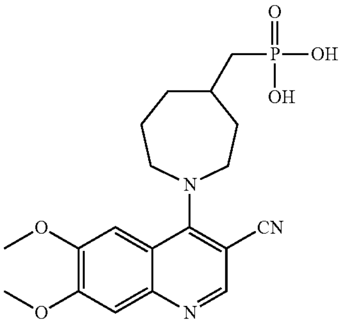 [SMILES: COc1cc2ncc(C#N)c(N3CCCC(CP(=O)(O)O)CC3)c2cc1OC] | ((1-(3-cyano-6,7-dimethoxyquinolin-4-yl)azepan-4-yl)methyl)phosphonic acid |
| I-8 | 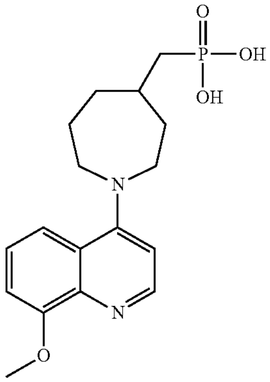 [SMILES: COc1cccc2c(N3CCCC(CP(=O)(O)O)CC3)ccnc12] | ((1-(8-methoxyquinolin-4-yl)azepan-4-yl)methyl)phosphonic acid |
| I-9 | 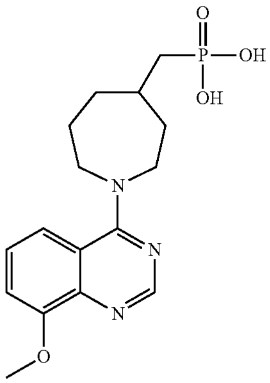 [SMILES: COc1cccc2c(N3CCCC(CP(=O)(O)O)CC3)ncnc12] | ((1-(8-methoxyquinazolin-4-yl)azepan-4-yl)methyl)phosphonic acid |

In some embodiments the compounds (e.g., compounds in Table 1A) are provided as base addition salts, such as a disodium salt.

Another embodiment provides a compound having the following Structure (II):

(II)

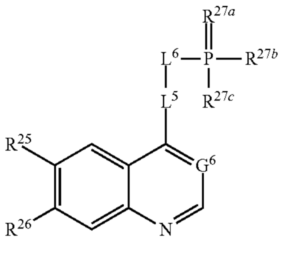

or a stereoisomer, tautomer, or pharmaceutically acceptable salt thereof, wherein:

$G^6$ is N or $CR^{28}$;

$L^5$ is $C_1$-$C_6$ alkylene, —$NR^{29}$—, —$N(R^{29})CH_2CH_2O$—, —O—, heteroarylene, or —$S(O)_t$—, wherein t is 0, 1, or 2;

$L^6$ is $C_1$-$C_6$ alkylene or $C_1$-$C_6$ alkenylene;

$R^{25}$, $R^{26}$, and $R^{28}$ are each independently hydrogen, alkyl, halo, hydroxy, cyano, haloalkyl, alkoxy, haloalkoxy, hydroxyalkyl, aminylcarbonylalkyl, or aminylalkyl, aminylcarbonyl, aminyl, alkylcarbonyl, —C(═O)Oalkyl, heterocyclyl, or heteroaryl;

$R^{27a}$ is O or S;

$R^{27b}$ and $R^{27c}$ are each independently —$O^-$, —OH, —$S^-$, —SH, or —$NR^{30a}R^{30b}$;

$R^{29}$ is hydrogen or $C_1$-$C_6$ alkyl; and $R^{30a}$ and $R^{30b}$ are, at each occurrence, independently hydrogen or alkyl.

In some embodiments, $G^6$ is N. In certain embodiments, $G^6$ is CH.

In some more specific embodiments, $R^{25}$ and $R^{26}$ are each independently hydrogen, halogen, hydroxy, alkoxy, aminylcarbonyl, aminyl, —C(═O)Oalkyl, or a 5-6 membered heteroaryl. In certain more specific embodiments, $R^{25}$ is hydrogen or alkoxy.

In some more specific embodiments, $R^{25}$ is hydrogen or methoxy.

In some embodiments, $R^{26}$ is hydrogen or alkoxy. In certain embodiments, $R^{26}$ is hydrogen or methoxy.

In some specific embodiments, $R^{27a}$ is O. In more specific embodiments, $R^{27b}$ —$O^-$ or —OH. In some embodiments, $R^{27c}$ —$O^-$ or —OH.

In certain embodiments, $L^5$ is branched $C_1$-$C_6$ alkylene. In more specific embodiments, $L^5$ is a 4-10 membered heteroarylene. In certain specific embodiments, $L^5$ is optionally substituted pyridinylene. In other embodiments, $L^5$ is —O—. In still other embodiments, $L^5$ is —NH—. In certain other embodiments, $L^5$ is —$N(CH_3)$—. In some other specific embodiments, $L^5$ is —S—. In other specific embodiments, $L^5$ is —$N(R^{29})CH_2CH_2O$—. In certain embodiments, $L^5$ is —$N(H)CH_2CH_2O$—.

In some embodiments, $L^6$ is $C_1$-$C_6$ alkylene. In some more specific embodiments, $L^6$ is unsubstituted.

In some more specific embodiments of the compound of Structure (II), the compound is selected from Table 1B, below. In any one of the foregoing embodiments, a stereoisomer, tautomer, prodrug, or pharmaceutically acceptable salt thereof is also included.

TABLE 1B

| Cmpd. No. | Structure | Name |
|---|---|---|
| Representative compounds of Structure (II) | | |
| II-1 | 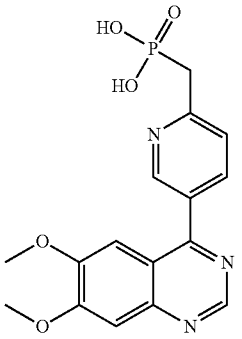 [SMILES: COc1cc2ncnc(-c3ccc(CP(=O)(O)O)nc3)c2cc1OC] | ((5-(6,7-dimethoxyquinazolin-4-yl)pyridin-2-yl)methyl)phosphonic acid |
| II-2 | 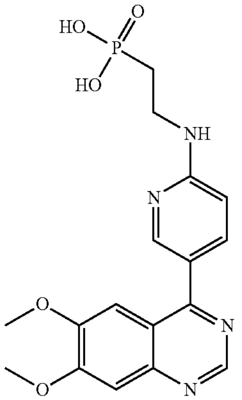 [SMILES: COc1cc2ncnc(-c3ccc(NCCP(=O)(O)O)nc3)c2cc1OC] | (2-((5-(6,7-dimethoxyquinazolin-4-yl)pyridin-2-yl)amino)ethyl) phosphonic acid |

TABLE 1B-continued

| Cmpd. No. | Structure | Name |
|---|---|---|
| Representative compounds of Structure (II) | | |
| II-3 | 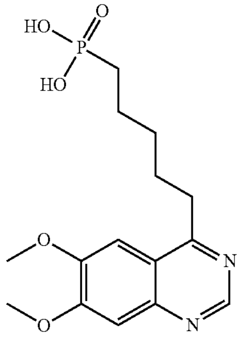 [SMILES: COc1cc2ncnc(CCCCCP(=O)(O)O)c2cc1OC] | (5-(6,7-dimethoxyquinazolin-4-yl)pentyl)phosphonic acid |
| II-4 | 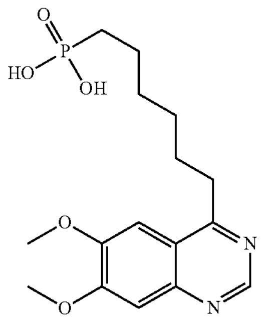 | (6-(6,7-dimethoxyquinazolin-4-yl)hexyl)phosphonic acid |
| II-5 | 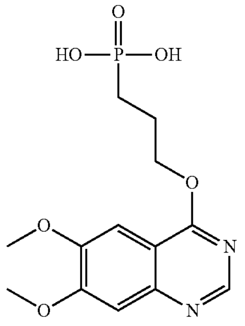 [SMILES: COc1cc2ncnc(OCCCP(=O)(O)O)c2cc1OC] | (3-((6,7-dimethoxyquinazolin-4-yl)oxy)propyl) phosphonic acid |
| II-6 | 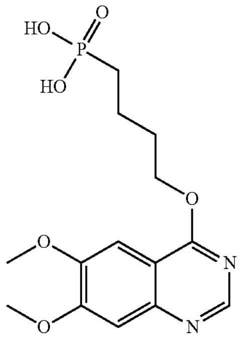 [SMILES: COc1cc2ncnc(OCCCCP(=O)(O)O)c2cc1OC] | (4-((6,7-dimethoxyquinazolin-4-yl)oxy)butyl) phosphonic acid |

TABLE 1B-continued

Representative compounds of Structure (II)

| Cmpd. No. | Structure | Name |
|---|---|---|
| II-7 | 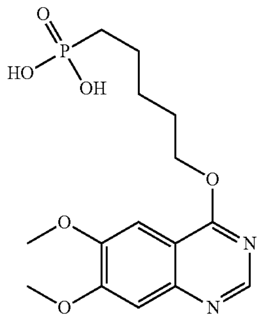 | (5-((6,7-dimethoxyquinazolin-4-yl)oxy)pentyl) phosphonic acid |
| II-8 | 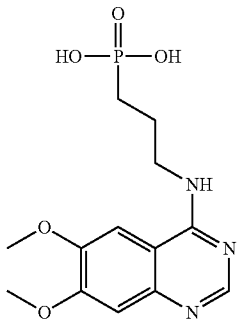 [SMILES: COc1cc2ncnc(NCCCP(=O)(O)O)c2cc1OC] | (3-((6,7-dimethoxyquinazolin-4-yl)amino)propyl) phosphonic acid |
| II-9 | 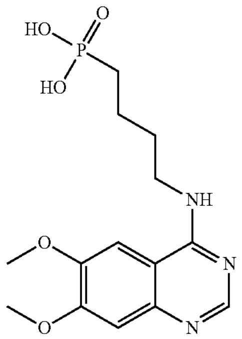 [SMILES: COc1cc2ncnc(NCCCCP(=O)(O)O)c2cc1OC] | (4-((6,7-dimethoxyquinazolin-4-yl)amino)butyl) phosphonic acid |
| II-10 | 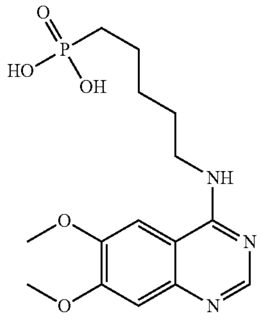 [SMILES: COc1cc2ncnc(NCCCCCP(=O)(O)O)c2cc1OC] | (5-((6,7-dimethoxyquinazolin-4-yl)amino)pentyl) phosphonic acid |
| II-11 | 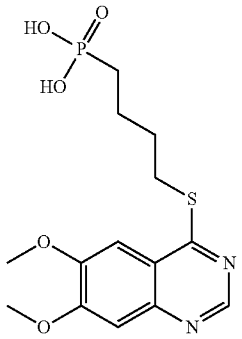 [SMILES: COc1cc2ncnc(SCCCCP(=O)(O)O)c2cc1OC] | (4-((6,7-dimethoxyquinazolin-4-yl)thio)butyl) phosphonic acid |
| II-12 | 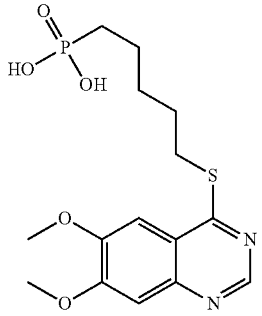 [SMILES: COc1cc2ncnc(SCCCCCP(=O)(O)O)c2cc1OC] | (5-((6,7-dimethoxyquinazolin-4-yl)thio)pentyl) phosphonic acid |
| II-13 | 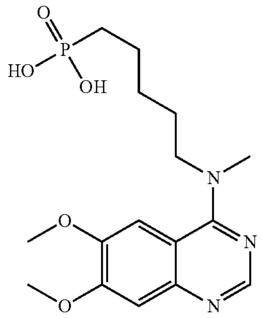 [SMILES: COc1cc2ncnc(N(C)CCCCCP(=O)(O)O)c2cc1OC] | (5-((6,7-dimethoxyquinazolin-4-yl)(methyl)amino) pentyl)phosphonic acid |
| II-14 | 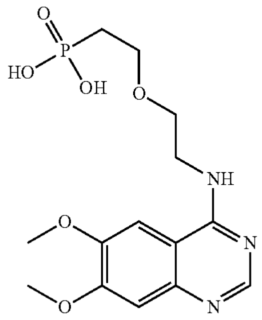 [SMILES: COc1cc2ncnc(NCCOCCP(=O)(O)O)c2cc1OC] | (2-(2-((6,7-dimethoxyquinazolin-4-yl)amino)ethoxy)ethyl) phosphonic acid |

In some embodiments the compounds (e.g., compounds in Table 1B) are provided as base addition salts, such as a disodium salt.

Pharmaceutical Compositions

Other embodiments are directed to pharmaceutical compositions. In some embodiments, the pharmaceutical composition comprises any one (or more) of the foregoing compounds of Structure (I), (II), or (III) (or pharmaceutically acceptable salt thereof) and a pharmaceutically acceptable carrier, diluent, or excipient. In some embodiments, the pharmaceutical composition is formulated for oral administration. In other embodiments, the pharmaceutical composition is formulated for injection. In still more embodiments, the pharmaceutical compositions comprise a compound as disclosed herein and an additional therapeutic agent. Non-limiting examples of such therapeutic agents are described herein below.

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound of Structure (I), (II), or (III) is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound of Structure (I), (II), or (III) is provided in the form of a rapid release formulation, in the form of an extended release formulation, or in the form of an intermediate release formulation. In yet other embodiments, the compound of Structure (I), (II), (III) is administered topically.

The compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that are used in some embodiments. An exemplary dosage is 10 to 30 mg per day. The exact dosage will depend upon the route of administration, the form in which the compound is administered, the subject to be treated, the body weight of the subject to be treated, and the preference and experience of the attending physician.

In some embodiments, a compound of the disclosure is administered in a single dose. Typically, such administration will be by injection, e.g., intravenous injection, in order to introduce the agent quickly. However, other routes are used as appropriate. A single dose of a compound of the disclosure may also be used for treatment of an acute condition.

In some embodiments, a compound of the disclosure is administered in multiple doses. In some embodiments, dosing is about once, twice, three times, four times, five times, six times, or more than six times per day. In other embodiments, dosing is about once a month, once every two weeks, once a week, or once every other day. In another embodiment a compound of the disclosure and another agent are administered together about once per day to about 6 times per day. In another embodiment the administration of a compound of the disclosure and an agent continues for less than about 7 days. In yet another embodiment the administration continues for more than about 6, 10, 14, 28 days, two months, six months, or one year. In some cases, continuous dosing is achieved and maintained as long as necessary.

Administration of the compounds of the disclosure may continue as long as necessary. In some embodiments, a compound of the disclosure is administered for more than 1, 2, 3, 4, 5, 6, 7, 14, or 28 days. In some embodiments, a compound of the disclosure is administered for less than 28, 14, 7, 6, 5, 4, 3, 2, or 1 day. In some embodiments, a compound of the disclosure is administered chronically on an ongoing basis, e.g., for the treatment of chronic effects.

In some embodiments, the compounds of the disclosure are administered in dosages. It is known in the art that due to intersubject variability in compound pharmacokinetics, individualization of dosing regimen is necessary for optimal therapy. Dosing for a compound of the disclosure may be found by routine experimentation in light of the instant disclosure.

In some embodiments, the compounds of Structure (I), (II), or (III) are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Provided herein are pharmaceutical compositions comprising a compound of Structure (I), (II), or (III) and a pharmaceutically acceptable diluent(s), excipient(s), or carrier(s). In certain embodiments, the compounds described are administered as pharmaceutical compositions in which compounds of Structure (I), (II), or (III) are mixed with other active ingredients, as in combination therapy. Encompassed herein are all combinations of actives set forth in the combination therapies section below and throughout this disclosure. In specific embodiments, the pharmaceutical compositions include one or more compounds of Structure (I), (II), or (III).

A pharmaceutical composition, as used herein, refers to a mixture of a compound of Structure (I), (II), or (III) with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of compounds of Structure (I), (II), or (III) provided herein are administered in a pharmaceutical composition to a mammal having a disease, disorder or medical condition to be treated. In specific embodiments, the mammal is a human. In certain embodiments, therapeutically effective amounts vary depending on the severity of the disease, the age and relative health of the subject, the potency of the compound used and other factors. The compounds of Structure (I), (II), or (III) are used singly or in combination with one or more therapeutic agents as components of mixtures.

In one embodiment, one or more compounds of Structure (I), (II), or (III) is formulated in an aqueous solutions. In specific embodiments, the aqueous solution is selected from, by way of example only, a physiologically compatible buffer, such as Hank's solution, Ringer's solution, or physiological saline buffer. In other embodiments, one or more compound of Structure (I), (II), or (III) is/are formulated for transmucosal administration. In specific embodiments, transmucosal formulations include penetrants that are appropriate to the barrier to be permeated. In still other embodiments wherein the compounds of Structure (I), (II), or (III) are formulated for other parenteral injections, appropriate formulations include aqueous or non-aqueous solutions. In specific embodiments, such solutions include physiologically compatible buffers and/or excipients.

In another embodiment, compounds of Structure (I), (II), or (III) are formulated for oral administration. Compounds of Structure (I), (II), or (III) are formulated by combining the active compounds with, e.g., pharmaceutically acceptable carriers or excipients. In various embodiments, the compounds of Structure (I), (II), or (III) are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the compounds of Structure (I), (II), or (III), optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds of Structure (I), (II), or (III) are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds of Structure (I), (II), or (III) are formulated for buccal or sublingual administration. Formulations suitable for buccal or sublingual administration include, by way of example only, tablets, lozenges, or gels. In still other embodiments, the compounds of Structure (I), (II), or (III) are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions are formulated in a form suitable for parenteral injection as sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the active compounds (e.g., compounds of Structure (I), (II), or (III)) are prepared as appropriate oily injection suspensions. Suitable lipophilic solvents or vehicles for use in the pharmaceutical compositions of Structure (I), (II), or (III) include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In still other embodiments, the compounds of Structure (I), (II), or (III) are administered topically. The compounds of Structure (I), (II), or (III) are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the compounds of Structure (I), (II), or (III) are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of the compounds of Structure (I), (II), or (III) is accomplished by means of iontophoretic patches and the like. In certain embodiments, transdermal patches provide controlled delivery of the compounds of Structure (I), (II), or (III). In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In other embodiments, the compounds of Structure (I), (II), or (III) are formulated for administration by inhalation. Various forms suitable for administration by inhalation include, but are not limited to, aerosols, mists or powders. Pharmaceutical compositions of any of compound of Structure (I), (II), or (III) are conveniently delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatin for use in an inhaler or insufflator is formulated containing a powder mix of the compound and a suitable powder base such as lactose or starch.

In still other embodiments, the compounds of Structure (I), (II), or (III) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are optionally used as suitable. Pharmaceutical compositions comprising a compound of Structure (I), (II), or (III) are manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one compound of Structure (I), (II), or (III), as an active ingredient. The active ingredient is in free-acid or free-base form, or in a pharmaceutically acceptable salt form. In addition, the methods and pharmaceutical compositions of Structure (I), (II), or (III) include the use of N-oxides, crystalline forms (also known as polymorphs), as well as active metabolites of these compounds having the same type of activity. All tautomers of the compounds of Structure (I), (II), or (III) are included within the scope of the compounds presented herein. Additionally, the compounds of Structure (I), (II), or (III) encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Accordingly, one embodiment provides a pharmaceutically acceptable salt of any one of the compounds of Structure (I), (II), or (III) described herein. In more specific embodiments, the pharmaceutically acceptable salt is an acid addition salt (e.g., a trifluoroacetic acid salt or a hydrochloric acid salt).

Methods for the preparation of compositions comprising the compounds of Structure (I), (II), or (III) include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions of Structure (I), (II), or (III) include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical composition comprising at least one compound of Structure (I), (II), or (III) illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, useful aqueous suspensions contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Useful pharmaceutical compositions also, optionally, include solubilizing agents to aid in the solubility of a compound of Structure (I), (II), or (III). The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, useful pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, useful compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other useful pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other useful compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other useful compositions include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, the compounds of Structure (I), (II), or (III) are delivered using a sustained-release system, such as semipermeable matrices of solid hydrophobic polymers containing the therapeutic agent. Various sustained-release materials are useful herein. In some embodiments, sustained-release capsules release the compounds for a few weeks up to over 100 days. Depending on the chemical nature and the biological stability of the therapeutic reagent, additional strategies for protein stabilization are employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (1) pentosan polysulfate and other heparinoids, (m) divalent cations such as magnesium and zinc; or (n) combinations thereof.

In some embodiments, the concentration of the compound of Structure (I), (II), or (III) provided in the pharmaceutical compositions is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of the compound of Structure (I), (II), or (III) provided in the pharmaceutical compositions is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.00010% w/w, w/v, or v/v.

In some embodiments, the concentration of the compound of Structure (I), (II), or (III) provided in the pharmaceutical compositions is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of the compound of Structure (I), (II), or (III) provided in the pharmaceutical compositions is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount the compound of Structure (I), (II), or (III) provided in the pharmaceutical compositions is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the compound of Structure (I), (II), or (III) provided in the pharmaceutical compositions is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of the compound of Structure (I), (II), or (III) provided in the pharmaceutical compositions is in the range of 0.0001-10 g, 0.0005-9 g, 0.001-8 g, 0.005-7 g, 0.01-6 g, 0.05-5 g, 0.1-4 g, 0.5-4 g, or 1-3 g.

Kits/Articles of Manufacture

For use in the therapeutic applications described herein, kits and articles of manufacture are also provided. In some embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from a variety of materials such as glass or plastic.

The articles of manufacture provided herein contain packaging materials. Packaging materials for use in packaging pharmaceutical products include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes one or more compounds of Structure (I), (II), or (III), optionally in a composition or in combination with another agent as disclosed herein. The container (s) optionally have a sterile access port (for example the container is an intravenous solution bag or a vial having a stopper pierceable by a hypodermic injection needle). Such kits optionally comprise a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound of Structure (I), (II), or (III). Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical compositions are presented in a pack or dispenser device which contains one or more unit dosage forms containing a compound provided herein. The pack for example contains metal or plastic foil, such as a blister pack. Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are prepared, placed in an appropriate container, and labeled for treatment of an indicated condition.

Methods of Treatment and Administration

Embodiments of the present disclosure provide a method for treating a disorder associated with an ENPP1 activity, CdnP activity, or both in a mammal comprising the step of administering to the mammal an effective amount of a disclosed compound, or a pharmaceutically acceptable salt, tautomer, isomer, hydrate, solvate, or polymorph thereof, or a pharmaceutical composition derived therefrom.

Other embodiments provide methods for inhibition of ENPP1 activity, CdnP activity, or both in a mammal comprising the step of administering to the mammal an effective amount of least one disclosed compound, or a pharmaceutically acceptable salt, tautomer, isomer, hydrate, solvate, or polymorph thereof, or a pharmaceutical composition derived therefrom.

Other embodiments describe methods for inhibiting ENPP1 activity, CdnP activity, or both in at least one cell, comprising the step of contacting at least one cell with an effective amount of at least one disclosed compound, or a pharmaceutically acceptable salt, tautomer, isomer, hydrate, solvate, or polymorph thereof, or a pharmaceutical composition derived therefrom.

Also disclosed are methods for treating a disorder associated with an ENPP1 activity, CdnP activity, or both in a mammal through eliciting an immunotherapeutic response in the mammal, comprising administering to the mammal an effective amount of a disclosed compound, or a pharmaceutically acceptable salt, tautomer, isomer, hydrate, solvate, or polymorph thereof, or a pharmaceutical composition derived therefrom, wherein this administration causes an immunotherapeutic response beneficial in the treatment of the disorder associated with an ENPP1 activity, CdnP activity, or both. Such a disorder can be, but is not limited to, any type of cancer or any disease caused by bacteria and/or viruses wherein ENPP1 activity, CdnP activity, or both has been implicated.

Accordingly, one embodiment provides a method for treating a disease comprising administering a compound of Structure (I) or (II), or a pharmaceutical composition comprising a compound of Structure (I) or (II) and a pharmaceutically acceptable carrier, diluent, or excipient.

In some embodiments, the disease is a mycobacterial infection. In some other embodiments, the disease is cancer (e.g., a solid tumor cancer or breast cancer). In some more specific embodiments, the method comprises inhibiting ENPP1 activity, CdnP activity, or both. In some more specific embodiments, the method comprises inhibiting CdnP activity (e.g., mycobacterial CdnP activity).

One specific embodiment provides a method for treating a mycobacterial infection comprising administering a pharmaceutical composition comprising a pharmaceutically acceptable carrier, diluent, or excipient and a compound having the following Structure (III):

(III)

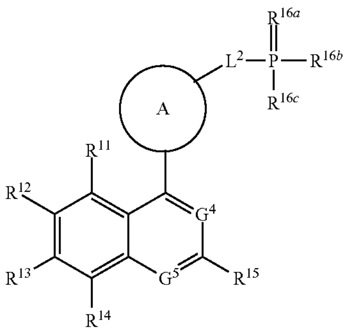

or a stereoisomer, tautomer, or pharmaceutically acceptable salt thereof, wherein:

A is $C_3$-$C_8$ cycloalkylene, 4-10 membered heterocyclylene, $C_6$-$C_{10}$ arylene, a 4-membered heteroarylene;

$L^2$ is $C_1$-$C_6$ alkylene optionally substituted with oxo;

$G^4$ is N or CH;

$G^5$ is N or CH;

$R^{11}$, $R^{12}$, $R^1$, $R^{14}$, and $R^{15}$ are each independently hydrogen, alkyl, halo, hydroxy, cyano, amino, —NH(C═O)alkyl, haloalkyl, alkoxy, haloalkoxy, hydroxyalkyl, alkenyleneheteroaryl, cycloalkyl, heterocyclyl, aryl, heteroaryl, or a combination of $R^{11}$ and $R^{12}$, $R^{12}$ and $R^{13}$, or $R^{13}$ and $R^{14}$ together with the carbons to which they are attached, join to form a 4-6 membered cycloalkyl, a 4-10 membered aryl, a 4-6 membered heterocyclyl, or a 4-10 membered heteroaryl;

$R^{16a}$ is O or S;

$R^{16b}$ and $R^{16c}$ are each independently —$O^-$, —OH, —$S^-$, —SH, or —$NR^{17a}R^{17b}$; and $R^{17a}$ and $R^{17b}$ are, at each occurrence, independently hydrogen or alkyl.

In some embodiments, A is 4-10 membered heterocyclylene. In certain embodiments, A is a 6 or 7 membered heterocyclylene. In some specific embodiments, A has one of the following structures:

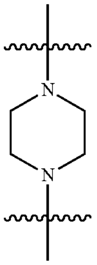 ; 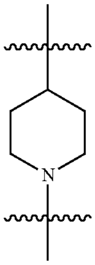 ; 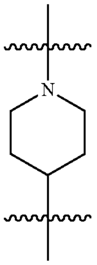 ; 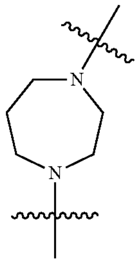 ;

-continued

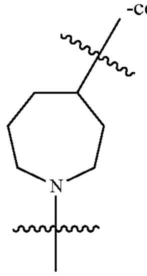 or 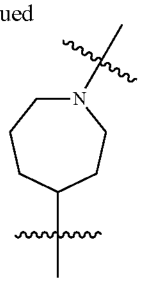 .

In certain embodiments, A has one of the following structures:

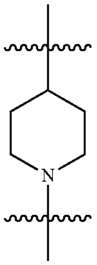 ; 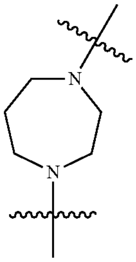 or 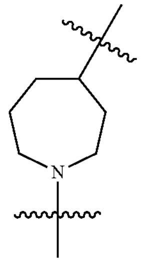 .

In some more specific embodiments, $G^4$ is N. In some embodiments, $G^4$ is CH.

In some specific embodiments, $G^5$ is N. In certain embodiments, $G^5$ is CH.

In some embodiments, $R^{11}$, $R^{12}$, $R^{13}$, $R^{14}$, and $R^{15}$ are each independently hydrogen, alkyl, halo, haloalkyl, alkoxy, haloalkoxy, or $R^2$ and $R^3$ together with the carbons to which they are attached, join to form a 4-6 membered heterocyclyl.

In some embodiments, $R^{11}$ is hydrogen or alkoxy. In certain embodiments, $R^{11}$ is hydrogen or methoxy.

In some more specific embodiments, $R^{12}$ is hydrogen or alkoxy. In some more specific embodiments, $R^{12}$ is hydrogen or methoxy.

In certain embodiments, $R^{13}$ is hydrogen or alkoxy. In some embodiments, $R^{13}$ is hydrogen or methoxy.

In certain embodiments, $R^{14}$ is hydrogen or alkoxy. In certain embodiments, $R^{14}$ is hydrogen or methoxy.

In some specific embodiments, $R^{15}$ is hydrogen.

In certain embodiments, $R^{16a}$ is O. In some embodiments, $R^{16b}$ is —$O^-$ or —OH. In certain embodiments, $R^{16c}$ is —$O^-$ or —OH.

In some embodiments, the method comprises inhibiting CdnP (e.g., mycobacterial CdnP). In some embodiments, the method comprises inhibiting ENPP1 (e.g., host ENPP1).

In more specific embodiments, the compound has one of the structures in Table 1 or Table 2. For example, in some more specific embodiments of the compound of Structure (I), the compound is selected from Table 1A, the compound of Structure (II) is selected from Table 1B, or the compound of Structure (III) is selected from Table 2, below. In any one of the foregoing embodiments, a stereoisomer, tautomer, prodrug, or pharmaceutically acceptable salt thereof is also included.

TABLE 2
| Representative compounds of Structure (III) | | |
|---|---|---|
| Cmpd. No. | Structure | Name |
| III-1 | 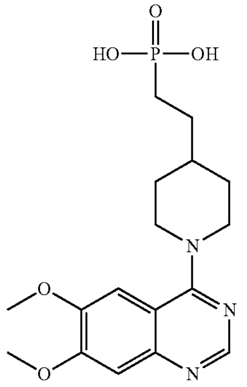 [SMILES: COc1cc2ncnc(N3CCC(CCP(=O)(O)O)CC3)c2cc1OC] | (2-(1-(6,7-dimethoxyquinazolin-4-yl)piperidin-4-yl)ethyl)phosphonic acid |
| III-2 | 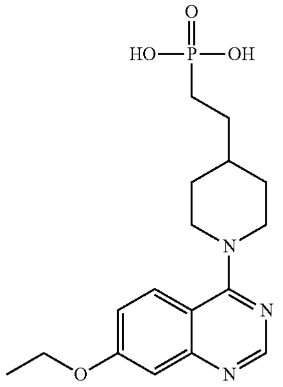 [SMILES: CCOc1ccc2c(N3CCC(CCP(=O)(O)O)CC3)ncnc2c1] | (2-(1-(7-ethoxyquinazolin-4-yl)piperidin-4-yl)ethyl)phosphonic acid |
| III-3 | 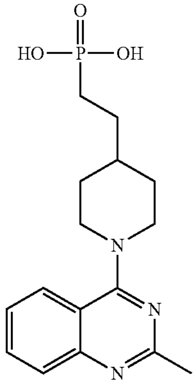 [SMILES: Cc1nc(N2CCC(CCP(=O)(O)O)CC2)c2ccccc2n1] | (2-(1-(2-methylquinazolin-4-yl)piperidin-4-yl)ethyl)phosphonic acid |
| III-4 | 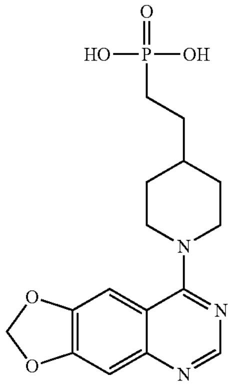 [SMILES: O=P(O)(O)CCC1CCN(c2ncnc3cc4c(cc23)OCO4)CC1] | (2-(1-([1,3]dioxolo[4,5-g]quinazolin-8-yl)piperidin-4-yl)ethyl)phosphonic acid |

TABLE 2-continued
| Representative compounds of Structure (III) | | |
| --- | --- | --- |
| Cmpd. No. | Structure | Name |
| III-5 | 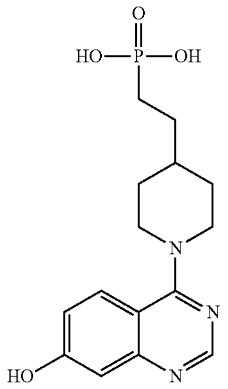 [SMILES: O=P(O)(O)CCC1CCN(c2ncnc3cc(O)ccc23)CC1] | (2-(1-(7-hydroxyquinazolin-4-yl)piperidin-4-yl)ethyl)phosphonic acid |
| III-6 | 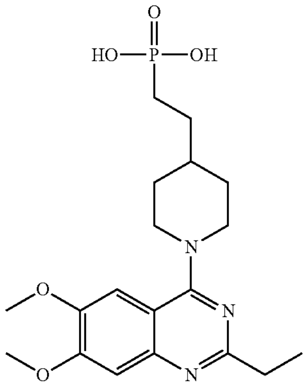 [SMILES: CCc1nc(N2CCC(CCP(=O)(O)O)CC2)c2cc(OC)c(OC)cc2n1] | (2-(1-(2-ethyl-6,7-dimethoxyquinazolin-4-yl)piperidin-4-yl)ethyl)phosphonic acid |
| III-7 | 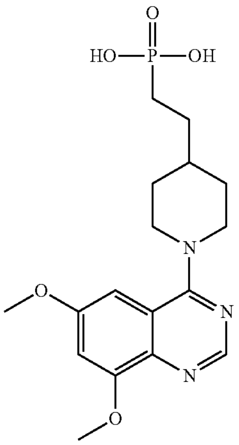 [SMILES: COc1cc(OC)c2ncnc(N3CCC(CCP(=O)(O)O)CC3)c2c1] | (2-(1-(6,8-dimethoxyquinazolin-4-yl)piperidin-4-yl)ethyl)phosphonic acid |

TABLE 2-continued
| Representative compounds of Structure (III) | | |
|---|---|---|
| Cmpd. No. | Structure | Name |
| III-8 | 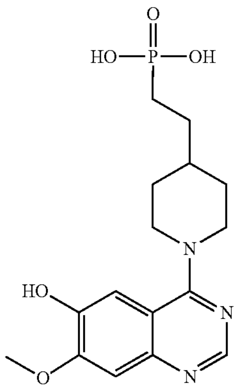 | (2-(1-(6-hydroxy-7-methoxyquinazolin-4-yl)piperidin-4-yl)ethyl)phosphonic acid |
| III-9 | 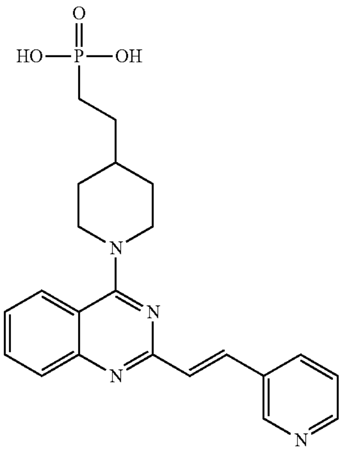 [SMILES: O=P(O)(O)CCC1CCN(c2nc(/C=C/c3cccnc3)nc3ccccc23)CC1] | (E)-(2-(1-(2-(2-(pyridin-3-yl)vinyl)quinazolin-4-yl)piperidin-4-yl)ethyl)phosphonic acid |
| III-10 | 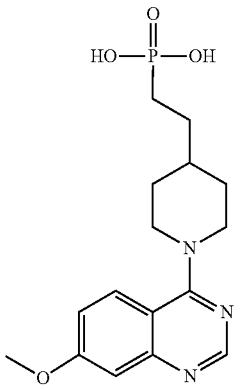 [SMILES: COc1ccc2c(N3CCC(CCP(=O)(O)O)CC3)ncnc2c1] | (2-(1-(7-methoxyquinazolin-4-yl)piperidin-4-yl)ethyl)phosphonic acid |

TABLE 2-continued
| Cmpd. No. | Structure | Name |
|---|---|---|
| | Representative compounds of Structure (III) | |
| III-11 | 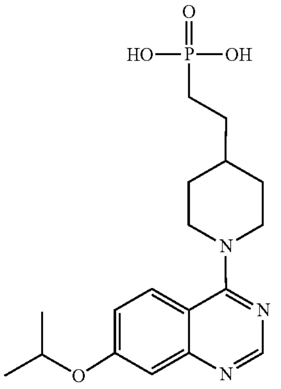 | (2-(1-(7-isopropoxyquinazolin-4-yl)piperidin-4-yl)ethyl)phosphonic acid |
| III-12 | 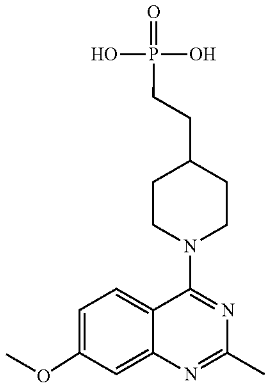 | (2-(1-(7-methoxy-2-methylquinazolin-4-yl)piperidin-4-yl)ethyl)phosphonic acid |
| III-13 | 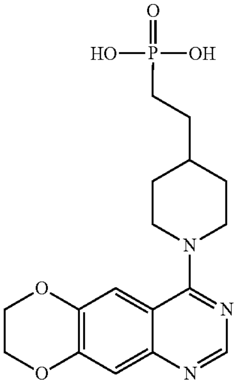 [SMILES: O=P(O)(O)CCC1CCN(c2ncnc3cc4c(cc23)OCCO4)CC1] | (2-(1-(7,8-dihydro-[1,4]dioxino[2,3-g]quinazolin-4-yl)piperidin-4-yl)ethyl) phosphonic acid |
| III-14 | 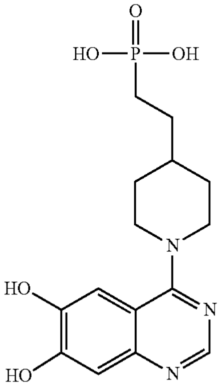 | (2-(1-(6,7-dihydroxyquinazolin-4-yl)piperidin-4-yl)ethyl)phosphonic acid |

TABLE 2-continued
| Representative compounds of Structure (III) | | |
|---|---|---|
| Cmpd. No. | Structure | Name |
| III-15 | 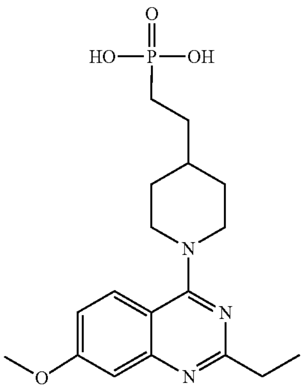 [SMILES: CCc1nc(N2CCC(CCP(=O)(O)O)CC2)c2ccc(OC)cc2n1] | (2-(1-(2-ethyl-7-methoxyquinazolin-4-yl)piperidin-4-yl)ethyl)phosphonic acid |
| III-16 | 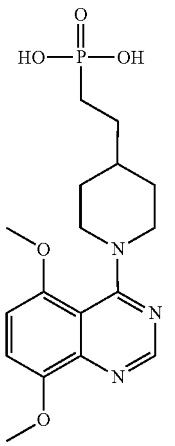 [SMILES: COc1ccc(OC)c2c(N3CCC(CCP(=O)(O)O)CC3)ncnc12] | (2-(1-(5,8-dimethoxyquinazolin-4-yl)piperidin-4-yl)ethyl)phosphonic acid |
| III-17 | 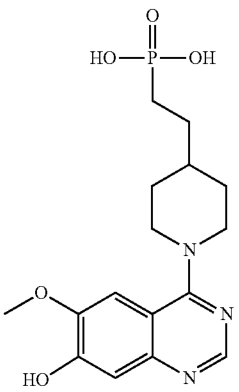 | (2-(1-(7-hydroxy-6-methoxyquinazolin-4-yl)piperidin-4-yl)ethyl)phosphonic acid |

TABLE 2-continued
| Representative compounds of Structure (III) | | |
|---|---|---|
| Cmpd. No. | Structure | Name |
| III-18 | 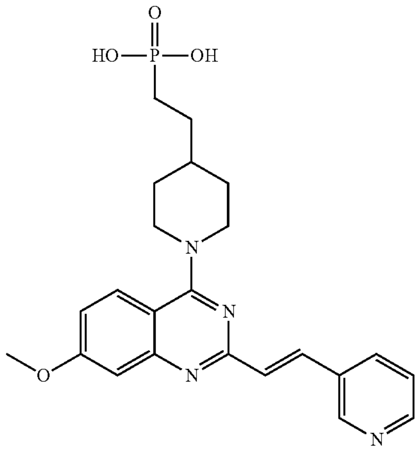 [SMILES: COc1ccc2c(N3CCC(CCP(=O)(O)O)CC3)nc(/C=C/c3cccnc3)nc2c1] | (E)-(2-(1-(7-methoxy-2-(2-(pyridin-3-yl)vinyl)quinazolin-4-yl)piperidin-4-yl)ethyl)phosphonic acid |
| III-19 | 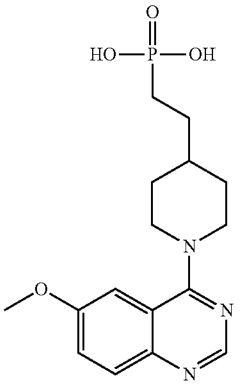 | (2-(1-(6-methoxyquinazolin-4-yl)piperidin-4-yl)ethyl)phosphonic acid |
| III-20 | 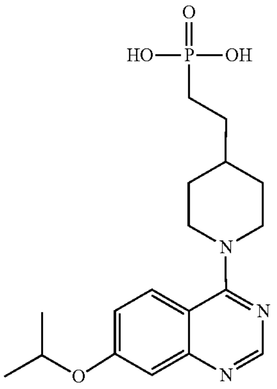 | (2-(1-(7-isopropoxyquinazolin-4-yl)piperidin-4-yl)ethyl)phosphonic acid |

TABLE 2-continued
| Representative compounds of Structure (III) | | |
|---|---|---|
| Cmpd. No. | Structure | Name |
| III-21 | 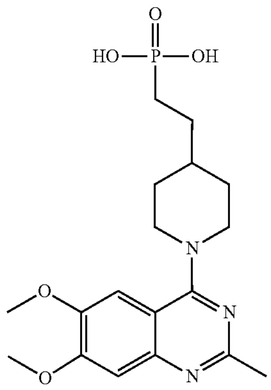 | (2-(1-(6,7-dimethoxy-2-methylquinazolin-4-yl)piperidin-4-yl)ethyl)phosphonic acid |
| III-22 | 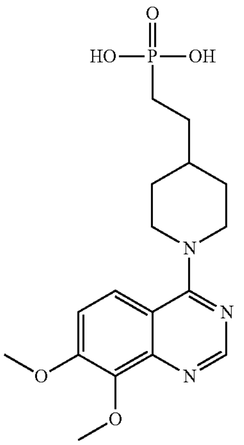 [SMILES: COc1ccc2c(N3CCC(CCP(=O)(O)O)CC3)ncnc2c1OC] | (2-(1-(7,8-dimethoxyquinazolin-4-yl)piperidin-4-yl)ethyl)phosphonic acid |
| III-23 | 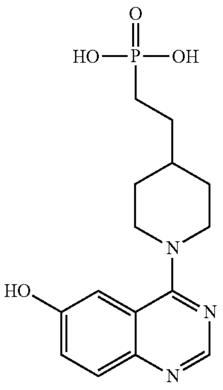 [SMILES: O=P(O)(O)CCC1CCN(c2ncnc3ccc(O)cc23)CC1] | (2-(1-(6-hydroxyquinazolin-4-yl)piperidin-4-yl)ethyl)phosphonic acid |

TABLE 2-continued
| Representative compounds of Structure (III) | | |
|---|---|---|
| Cmpd. No. | Structure | Name |
| III-24 | 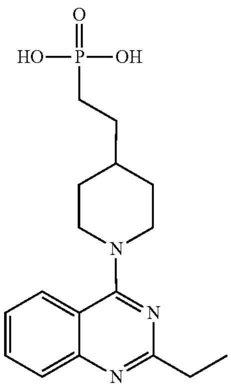 [SMILES: CCc1nc(N2CCC(CCP(=O)(O)O)CC2)c2ccccc2n1] | (2-(1-(2-ethylquinazolin-4-yl)piperidin-4-yl)ethyl)phosphonic acid |
| III-25 | 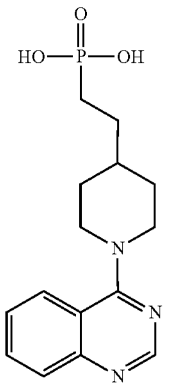 [SMILES: O=P(O)(O)CCC1CCN(c2ncnc3ccccc23)CC1] | (2-(1-(quinazolin-4-yl)piperidin-4-yl)ethyl)phosphonic acid |
| III-26 | 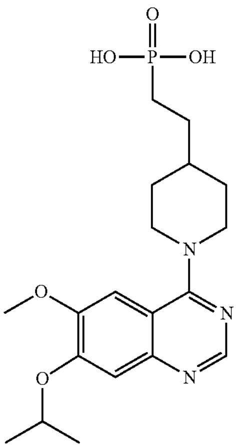 [SMILES: COc1cc2c(N3CCC(CCP(=O)(O)O)CC3)ncnc2cc1OC(C)C] | (2-(1-(7-isopropoxy-6-methoxyquinazolin-4-yl)piperidin-4-yl)ethyl)phosphonic acid |

TABLE 2-continued
| Representative compounds of Structure (III) | | |
|---|---|---|
| Cmpd. No. | Structure | Name |
| III-27 | 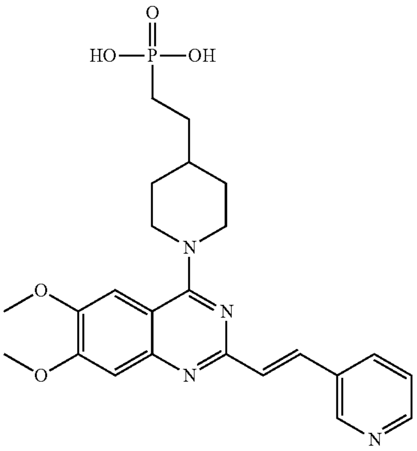 [SMILES: COc1cc2nc(/C=C/c3cccnc3)nc(N3CCC(CCP(=O)(O)O)CC3)c2cc1OC] | (E)-(2-(1-(6,7-dimethoxy-2-(2-(pyridin-3-yl)vinyl)quinazolin-4-yl)piperidin-4-yl)ethyl)phosphonic acid |
| III-28 | 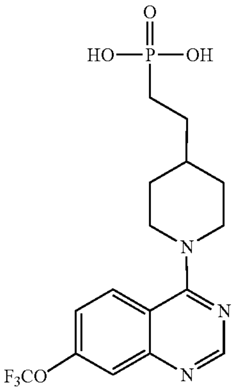 [SMILES: O=P(O)(O)CCC1CCN(c2ncnc3cc(OC(F)(F)F)ccc23)CC1] | (2-(1-(7-(trifluoromethoxy)quinazolin-4-yl)piperidin-4-yl)ethyl)phosphonic acid |
| III-29 | 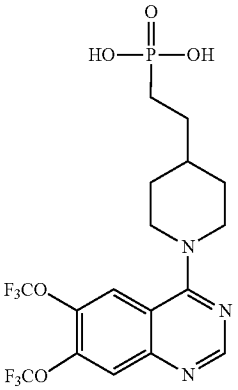 [SMILES: O=P(O)(O)CCC1CCN(c2ncnc3cc(OC(F)(F)F)c(OC(F)(F)F)cc23)CC1] | (2-(1-(6,7-bis(trifluoromethoxy)quinazolin-4-yl)piperidin-4-yl)ethyl)phosphonic acid |

TABLE 2-continued
| Cmpd. No. | Structure | Name |
|---|---|---|
| | Representative compounds of Structure (III) | |
| III-30 | 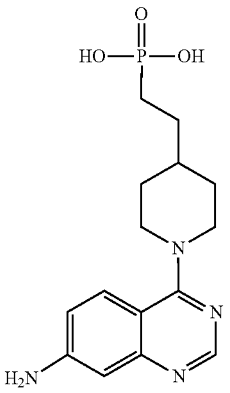 [SMILES: Nc1ccc2c(N3CCC(CCP(=O)(O)O)CC3)ncnc2c1] | (2-(1-(7-aminoquinazolin-4-yl)piperidin-4-yl)ethyl)phosphonic acid |
| III-31 | 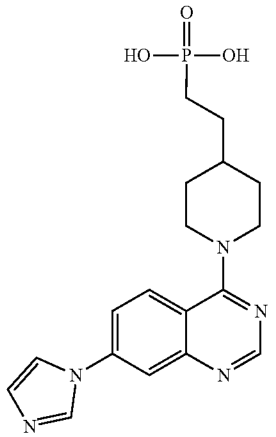 [SMILES: O=P(O)(O)CCC1CCN(c2ncnc3cc(-n4ccnc4)ccc23)CC1] | (2-(1-(7-(1H-imidazol-1-yl)quinazolin-4-yl)piperidin-4-yl)ethyl)phosphonic acid |
| III-32 | 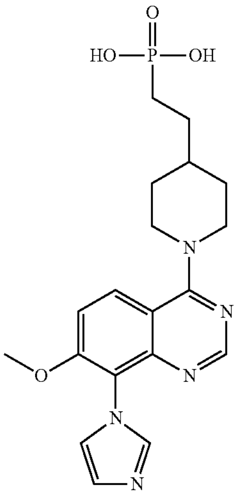 [SMILES: COc1ccc2c(N3CCC(CCP(=O)(O)O)CC3)ncnc2c1-n1ccnc1] | (2-(1-(8-(1H-imidazol-1-yl)-7-methoxyquinazolin-4-yl)piperidin-4-yl)ethyl)phosphonic acid |

TABLE 2-continued
| Representative compounds of Structure (III) | | |
|---|---|---|
| Cmpd. No. | Structure | Name |
| III-33 | 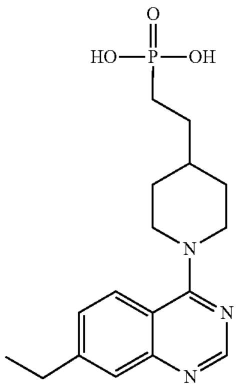 [SMILES: CCc1ccc2c(N3CCC(CCP(=O)(O)O)CC3)ncnc2c1] | (2-(1-(7-ethylquinazolin-4-yl)piperidin-4-yl)ethyl)phosphonic acid |
| III-34 | 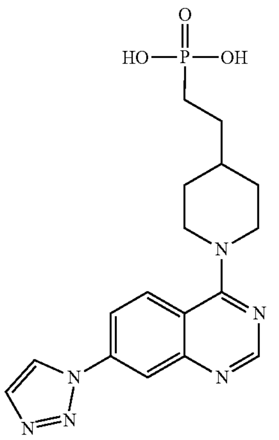 | (2-(1-(7-(1H-1,2,3-triazol-1-yl)quinazolin-4-yl)piperidin-4-yl)ethyl)phosphonic acid |
| III-35 | 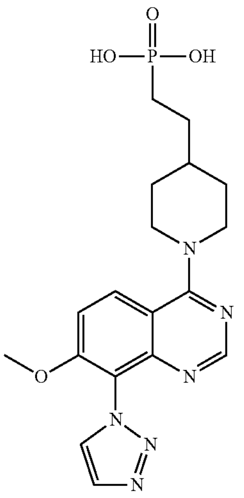 [SMILES: COc1ccc2c(N3CCC(CCP(=O)(O)O)CC3)ncnc2c1-n1ccnn1] | (2-(1-(7-methoxy-8-(1H-1,2,3-triazol-1-yl)quinazolin-4-yl)piperidin-4-yl)ethyl)phosphonic acid |

TABLE 2-continued
| Representative compounds of Structure (III) | | |
|---|---|---|
| Cmpd. No. | Structure | Name |
| III-36 | 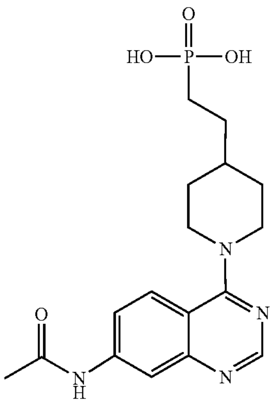 [SMILES: CC(=O)Nc1ccc2c(N3CCC(CCP(=O)(O)O)CC3)ncnc2c1] | (2-(1-(7-acetamidoquinazolin-4-yl)piperidin-4-yl)ethyl)phosphonic acid |
| III-37 | 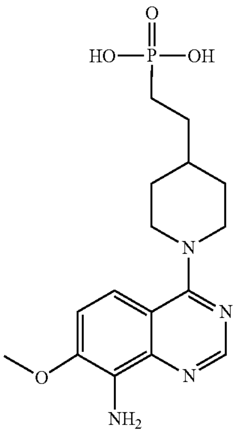 [SMILES: COc1ccc2c(N3CCC(CCP(=O)(O)O)CC3)ncnc2c1N] | (2-(1-(8-amino-7-methoxyquinazolin-4-yl)piperidin-4-yl)ethyl)phosphonic acid |
| III-38 | 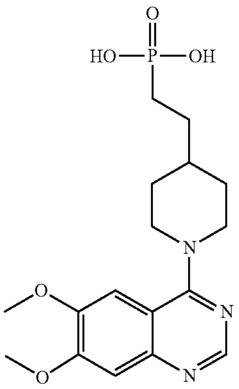 [SMILES: COc1cc2ncnc(N3CCC(CCP(=O)(O)O)CC3)c2cc1OC] | (2-(1-(6,7-dimethoxyisoquinolin-1-yl)piperidin-4-yl)ethyl)phosphonic acid |

TABLE 2-continued
| Representative compounds of Structure (III) | | |
|---|---|---|
| Cmpd. No. | Structure | Name |
| III-39 | 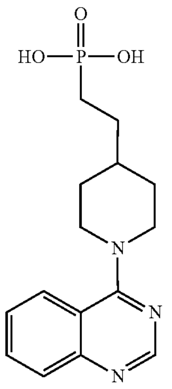 [SMILES: O=P(O)(O)CCC1CCN(c2ncnc3ccccc23)CC1] | (2-(4-(quinazolin-4-yl)piperazin-1-yl)ethyl)phosphonic acid |
| III-40 | 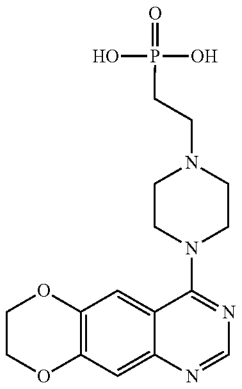 [SMILES: O=P(O)(O)CCN1CCN(c2ncnc3cc4c(cc23)OCCO4)CC1] | (2-(4-(7,8-dihydro-[1,4]dioxino[2,3-g]quinazolin-4-yl)piperazin-1-yl)ethyl)phosphonic acid |
| III-41 | 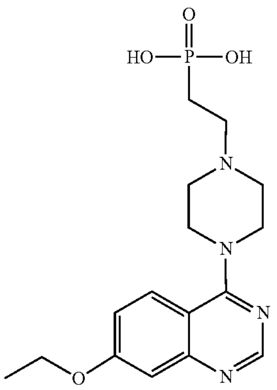 [SMILES: CCOc1ccc2c(N3CCN(CCP(=O)(O)O)CC3)ncnc2c1] | (2-(4-(7-ethoxyquinazolin-4-yl)piperazin-1-yl)ethyl)phosphonic acid |

TABLE 2-continued
| Representative compounds of Structure (III) | | |
|---|---|---|
| Cmpd. No. | Structure | Name |
| III-42 | 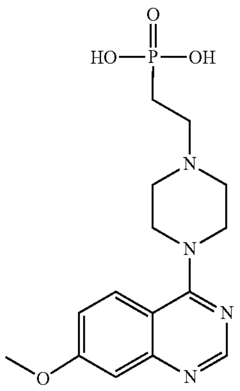 | (2-(4-(7-methoxyquinazolin-4-yl)piperazin-1-yl)ethyl)phosphonic acid |
| III-43 | 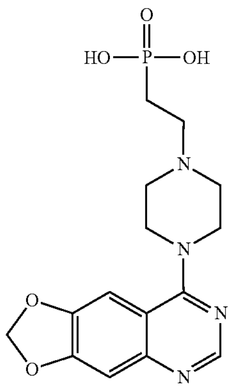 [SMILES: O=P(O)(O)CCN1CCN(c2ncnc3cc4c(cc23)OCO4)CC1] | (2-(4-([1,3]dioxolo[4,5-g]quinazolin-8-yl)piperazin-1-yl)ethyl)phosphonic acid |
| III-44 | 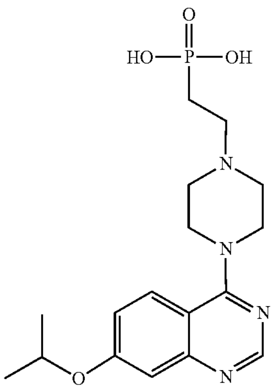 [SMILES: CC(C)Oc1ccc2c(N3CCN(CCP(=O)(O)O)CC3)ncnc2c1] | (2-(4-(7-isopropoxyquinazolin-4-yl)piperazin-1-yl)ethyl)phosphonic acid |

TABLE 2-continued
| Representative compounds of Structure (III) | | |
|---|---|---|
| Cmpd. No. | Structure | Name |
| III-45 | 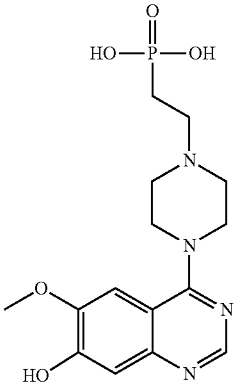 [SMILES: COc1cc2c(N3CCN(CCP(=O)(O)O)CC3)ncnc2cc1O] | (2-(4-(7-hydroxy-6-methoxyquinazolin-4-yl)piperazin-1-yl)ethyl)phosphonic acid |
| III-46 | 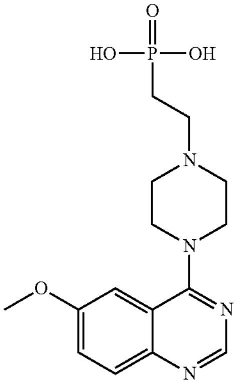 [SMILES: COc1ccc2ncnc(N3CCN(CCP(=O)(O)O)CC3)c2c1] | (2-(4-(6-methoxyquinazolin-4-yl)piperazin-1-yl)ethyl)phosphonic acid |
| III-47 | 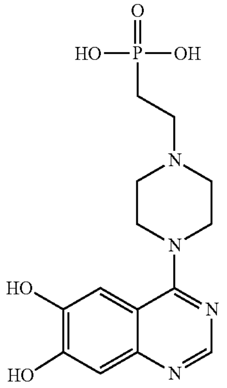 [SMILES: O=P(O)(O)CCN1CCN(c2ncnc3cc(O)c(O)cc23)CC1] | (2-(4-(6,7-dihydroxyquinazolin-4-yl)piperazin-1-yl)ethyl)phosphonic acid |
| III-48 | 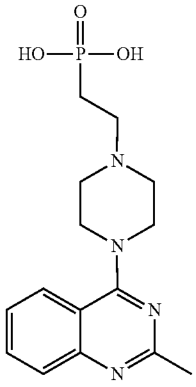 [SMILES: Cc1nc(N2CCN(CCP(=O)(O)O)CC2)c2ccccc2n1] | (2-(4-(2-methylquinazolin-4-yl)piperazin-1-yl)ethyl)phosphonic acid |

TABLE 2-continued
| Representative compounds of Structure (III) | | |
|---|---|---|
| Cmpd. No. | Structure | Name |
| III-49 | 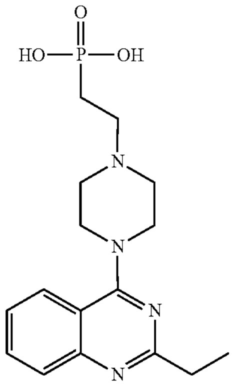 [SMILES: CCc1nc(N2CCN(CCP(=O)(O)O)CC2)c2ccccc2n1] | (2-(4-(2-ethylquinazolin-4-yl)piperazin-1-yl)ethyl)phosphonic acid |
| III-50 | 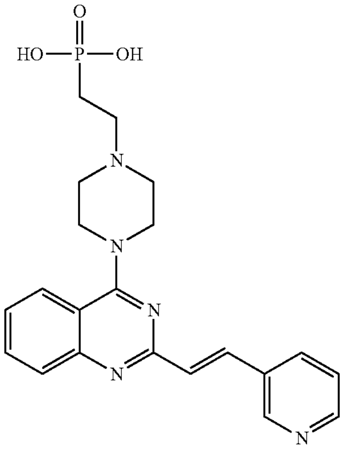 [SMILES: O=P(O)(O)CCN1CCN(c2nc(/C=C/c3cccnc3)nc3ccccc23)CC1] | (E)-(2-(4-(2-(2-(pyridin-2-yl)vinyl)quinazolin-4-yl)piperazin-1-yl)ethyl)phosphonic acid |
| III-51 | 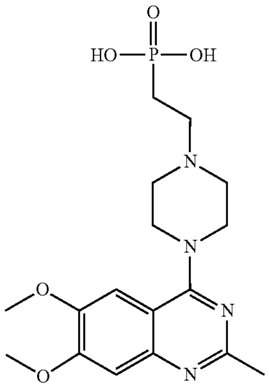 | (2-(4-(6,7-dimethoxy-2-methylquinazolin-4-yl)piperazin-1-yl)ethyl)phosphonic acid |

TABLE 2-continued
| Representative compounds of Structure (III) | | |
|---|---|---|
| Cmpd. No. | Structure | Name |
| III-52 | 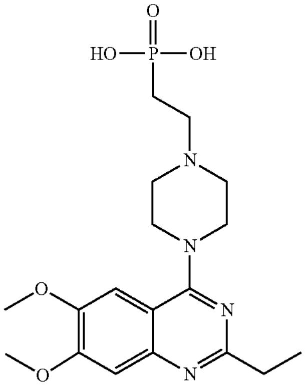 [SMILES: CCc1nc(N2CCN(CCP(=O)(O)O)CC2)c2cc(OC)c(OC)cc2n1] | (2-(4-(2-ethyl-6,7-dimethoxyquinazolin-4-yl)piperazin-1-yl)ethyl)phosphonic acid |
| III-53 | 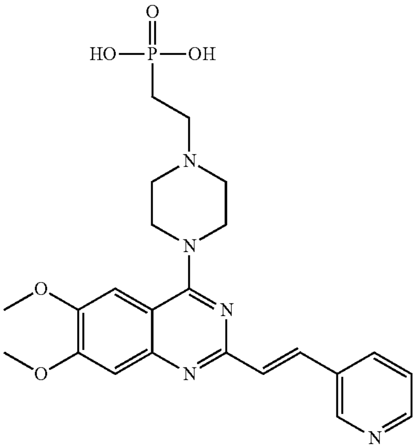 [SMILES: COc1cc2nc(/C=C/c3cccnc3)nc(N3CCN(CCP(=O)(O)O)CC3)c2cc1OC] | (E)-(2-(4-(6,7-dimethoxy-2-(2-(pyridin-3-yl)vinyl)quinazolin-4-yl)piperazin-1-yl)ethyl)phosphonic acid |
| III-54 | 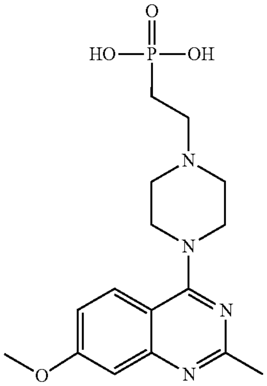 | (2-(4-(7-methoxy-2-methylquinazolin-4-yl)piperazin-1-yl)ethyl)phosphonic acid |

TABLE 2-continued
| Representative compounds of Structure (III) | | |
|---|---|---|
| Cmpd. No. | Structure | Name |
| III-55 | 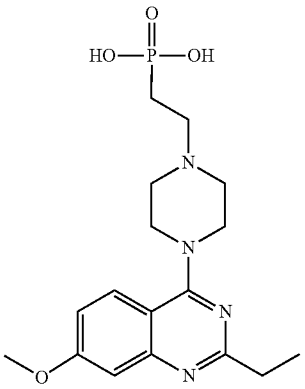 [SMILES: CCc1nc(N2CCN(CCP(=O)(O)O)CC2)c2ccc(OC)cc2n1] | (2-(4-(2-ethyl-7-methoxyquinazolin-4-yl)piperazin-1-yl)ethyl)phosphonic acid |
| III-56 | 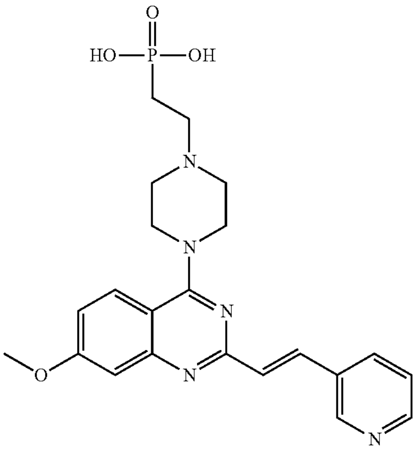 [SMILES: COc1ccc2c(N3CCN(CCP(=O)(O)O)CC3)nc(/C=C/c3cccnc3)nc2c1] | (E)-(2-(4-(7-methoxy-2-(2-(pyridin-3-yl)vinyl)quinazolin-4-yl)piperazin-1-yl)ethyl)phosphonic acid |
| III-57 | 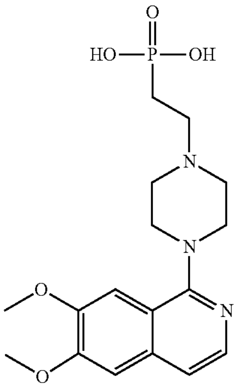 [SMILES: COc1cc2ccnc(N3CCN(CCP(=O)(O)O)CC3)c2cc1OC] | (2-(4-(6,7-dimethoxyisoquinolin-1-yl)piperazin-1-yl)ethyl)phosphonic acid |

TABLE 2-continued
| Representative compounds of Structure (III) | | |
|---|---|---|
| Cmpd. No. | Structure | Name |
| III-58 | 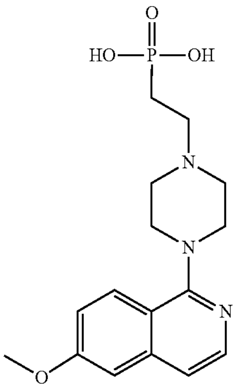 [SMILES: COc1ccc2c(N3CCN(CCP(=O)(O)O)CC3)nccc2c1] | (2-(4-(6-methoxyisoquinolin-1-yl)piperazin-1-yl)ethyl)phosphonic acid |
| III-59 | 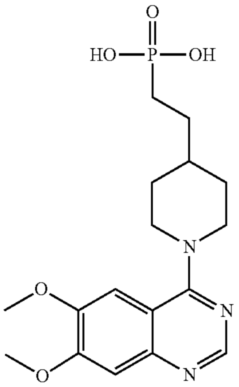 [SMILES: COc1cc2ncnc(N3CCC(CCP(=O)(O)O)CC3)c2cc1OC] | (2-(1-(6,7-dimethoxyquinazolin-4-yl)piperidin-4-yl)ethyl)phosphonic acid |
| III-60 | 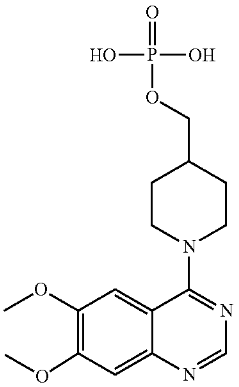 | (1-(6,7-dimethoxyquinazolin-4-yl)piperidin-4-yl)methyl dihydrogen phosphate |

TABLE 2-continued
| Representative compounds of Structure (III) | | |
|---|---|---|
| Cmpd. No. | Structure | Name |
| III-61 | 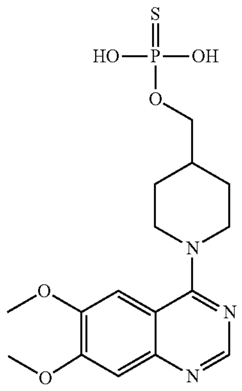 [SMILES: COc1cc2ncnc(N3CCC(COP(=O)(O)O)CC3)c2cc1OC] | O-((1-(6,7-dimethoxyquinazolin-4-yl)piperidin-4-yl)methyl) O,O-dihydrogen phosphorothioate |
| III-62 | 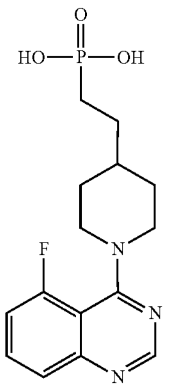 [SMILES: O=P(O)(O)CCC1CCN(c2ncnc3cccc(F)c23)CC1] | (2-(1-(5-fluoroquinazolin-4-yl)piperidin-4-yl)ethyl)phosphonic acid |
| III-63 | 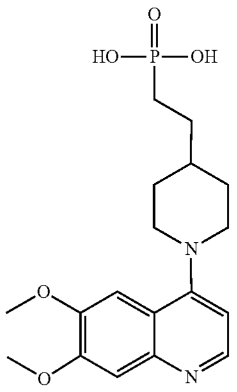 [SMILES: COc1cc2nccc(N3CCC(CCP(=O)(O)O)CC3)c2cc1OC] | (2-(1-(6,7-dimethoxyquinolin-4-yl)piperidin-4-yl)ethyl)phosphonic acid |

TABLE 2-continued
| Representative compounds of Structure (III) | | |
|---|---|---|
| Cmpd. No. | Structure | Name |
| III-64 | 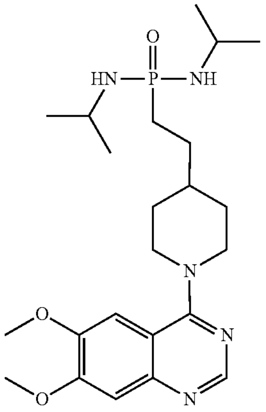 [SMILES: COc1cc2ncnc(N3CCC(CCP(=O)(NC(C)C)NC(C)C)CC3)c2cc1OC] | (2-(1-(6,7-dimethoxyquinazolin-4-yl)piperidin-4-yl)ethyl-N-diisopropylphosphanediamine |
| III-65 | 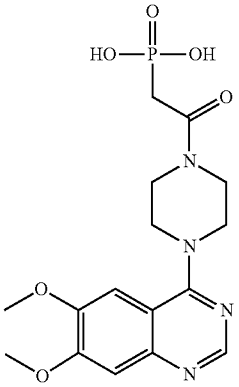 [SMILES: COc1cc2ncnc(N3CCN(C(=O)CP(=O)(O)O)CC3)c2cc1OC] | (2-(4-(6,7-dimethoxyquinazolin-4-yl)piperazin-1-yl)-2-oxoethyl)phosphonic acid |
| III-66 | 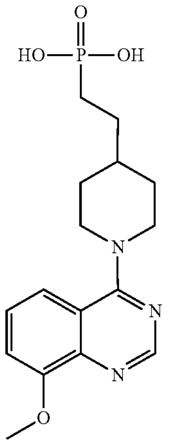 [SMILES: COc1cccc2c(N3CCC(CCP(=O)(O)O)CC3)ncnc12] | (2-(1-(8-methoxyquinazolin-4-yl)piperidin-4-yl)ethyl)phosphonic acid |

TABLE 2-continued
| Representative compounds of Structure (III) | | |
|---|---|---|
| Cmpd. No. | Structure | Name |
| III-67 | 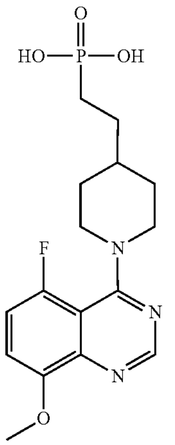 [SMILES: COc1ccc(F)c2c(N3CCC(CCP(=O)(O)O)CC3)ncnc12] | (2-(1-(5-fluoro-8-methoxyquinazolin-4-yl)piperidin-4-yl)ethyl)phosphonic acid |
| III-68 | 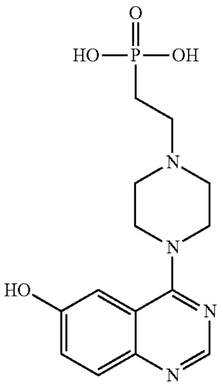 [SMILES: O=P(O)(O)CCN1CCN(c2ncnc3ccc(O)cc23)CC1] | (2-(4-(6-hydroxyquinazolin-4-yl)piperazin-1-yl)ethyl)phosphonic acid |
| III-69 | 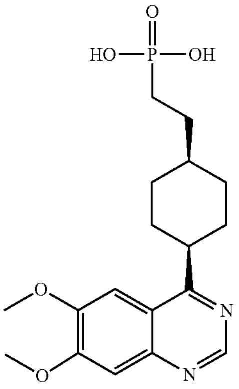 [SMILES: COc1cc2ncnc([C@H]3CC[C@@H](CCP(=O)(O)O)CC3)c2cc1OC] | (2-((1s,4s)-4-(6,7-dimethoxyquinazolin-4-yl)cyclohexyl)ethyl)phosphonic acid |

TABLE 2-continued
Representative compounds of Structure (III)
| Cmpd. No. | Structure | Name |
|---|---|---|
| III-70 | 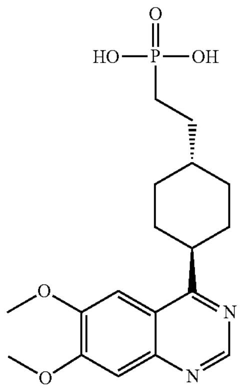 [SMILES: COc1cc2ncnc([C@H]3CC[C@H](CCP(=O)(O)O)CC3)c2cc1OC] | (2-((1r,4r)-4-(6,7-dimethoxyquinazolin-4-yl)cyclohexyl)ethyl)phosphonic acid |
| III-71 | 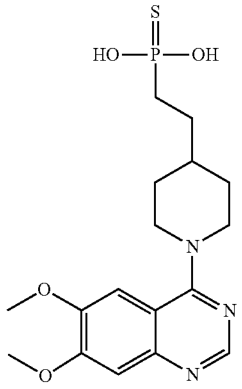 | (2-(1-(6,7-dimethoxyquinazolin-4-yl)piperidin-4-yl)ethyl)phosphonothioic O,O-acid |
| III-72 | 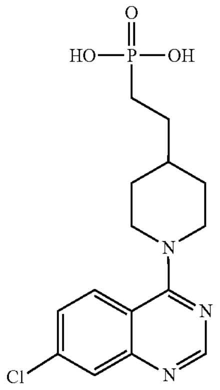 [SMILES: O=P(O)(O)CCC1CCN(c2ncnc3cc(Cl)ccc23)CC1] | (2-(1-(7-chloroquinazolin-4-yl)piperidin-4-yl)ethyl)phosphonic acid |

TABLE 2-continued
| Representative compounds of Structure (III) | | |
|---|---|---|
| Cmpd. No. | Structure | Name |
| III-73 | 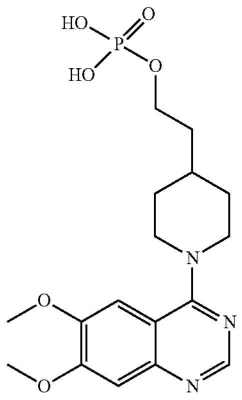 [SMILES: COc1cc2ncnc(N3CCC(CCOP(=O)(O)O)CC3)c2cc1OC] | 2-(1-(6,7-dimethoxyquinazolin-4-yl)piperidin-4-yl)ethyl dihydrogen phosphate |
| III-74 | 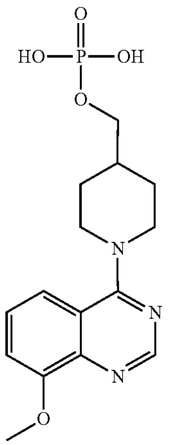 [SMILES: COc1cccc2c(N3CCC(COP(=O)(O)O)CC3)ncnc12] | (1-(8-methoxyquinazolin-4-yl)piperdin-4-yl)methyl dihydrogen phosphate |
| III-75 | 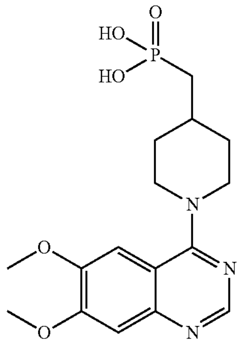 [SMILES: COc1cc2ncnc(N3CCC(CP(=O)(O)O)CC3)c2cc1OC] | ((1-(6,7-dimethoxyquinazolin-4-yl)piperidin-4-yl)methyl)phosphonic acid |

TABLE 2-continued
| Representative compounds of Structure (III) | | |
|---|---|---|
| Cmpd. No. | Structure | Name |
| III-76 | 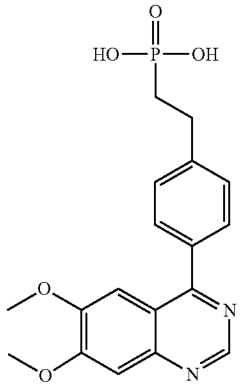 [SMILES: COc1cc2ncnc(-c3ccc(CCP(=O)(O)O)cc3)c2cc1OC] | (4-(6,7-dimethoxyquinazolin-4-yl)phenethyl)phosphonic acid |
| III-77 | 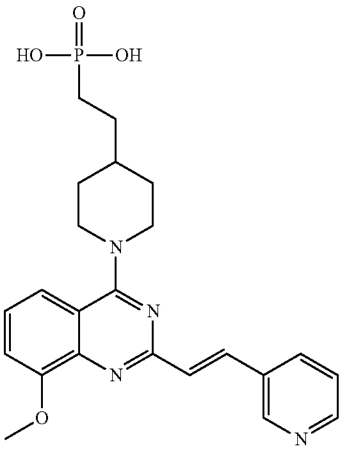 [SMILES: COc1cccc2c(N3CCC(CCP(=O)(O)O)CC3)nc(/C=C/c3cccnc3)nc12] | (E)-(2-(1-(8-methoxy-2-(2-(pyridin-3-yl)vinyl)quinazolin-4-yl)piperidin-4-yl)ethyl)phosphonic acid |
| III-78 | 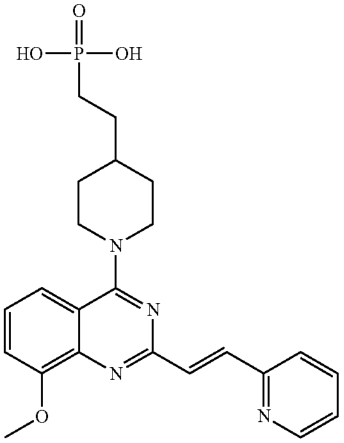 [SMILES: COc1cccc2c(N3CCC(CCP(=O)(O)O)CC3)nc(/C=C/c3ccccn3)nc12] | (E)-(2-(1-(8-methoxy-2-(2-(pyridin-2-yl)vinyl)quinazolin-4-yl)piperidin-4-yl)ethyl)phosphonic acid |

TABLE 2-continued
| Representative compounds of Structure (III) | | |
|---|---|---|
| Cmpd. No. | Structure | Name |
| III-79 | 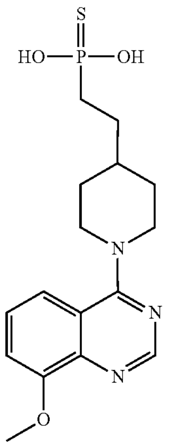 [SMILES: COc1cccc2c(N3CCC(CCP(O)(O)=S)CC3)ncnc12] | (2-(1-(8-methoxyquinazolin-4-yl)piperidin-4-yl)ethyl)phosphonothioic O,O-acid |
| III-80 | 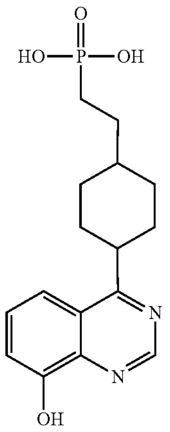 [SMILES: O=P(O)(O)CCC1CCC(c2ncnc3c(O)cccc23)CC1] | (2-(4-(8-hydroxyquinazolin-4-yl)cyclohexyl)ethyl)phosphonic acid |
| III-81 | 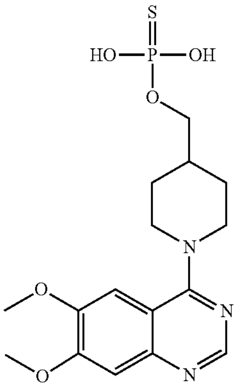 | O-((1-(6,7-dimethoxyquinazolin-4-yl)piperidin-4-yl)methyl) O,O-dihydrogen phosphorothioate |

TABLE 2-continued

| Representative compounds of Structure (III) | | |
|---|---|---|
| Cmpd. No. | Structure | Name |
| III-82 | 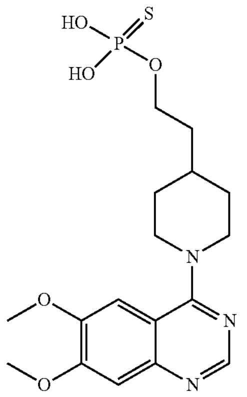 [SMILES: COc1cc2ncnc(N3CCC(CCOP(O)(O)=S)CC3)c2cc1OC] | O-(2-(1-(6,7-dimethoxyquinazolin-4-yl)piperidin-4-yl)ethyl) O,O-dihydrogen phosphorothioate |

In some embodiments the compounds (e.g., compounds in Table 2) are provided as base addition salts, such as a disodium salt.

Inhibition or loss of ENPP1 can attenuate bacterial or viral virulence. Further, bacterial or viral infection leads to reduced IFN-β and NF-κB particularly in cells expressed in high ENPP1. Examination of the molecular mechanisms of ENPP1 during viral or bacterial infection revealed that the ENPP1 involved in hydrolysis of cGAMP in infected or transfected cells and that leads to inhibition of IRF3 phosphorylation, thus reducing IFN-β secretion. These results, combined with human cGAS, further validate the hypothesis that the ENPP1 acts through cGAS to maintain the cGAMP levels and contributes to viral or bacterial infection. Still more embodiments include pharmaceutical compositions comprising a pharmaceutically acceptable carrier and an effective amount of a disclosed compound, or a pharmaceutically acceptable salt, tautomer, isomer, hydrate, solvate, or polymorph thereof.

Also disclosed are kits comprising at least one disclosed compound, or a pharmaceutically acceptable salt, tautomer, isomer, hydrate, solvate, or polymorph thereof.

Also disclosed are methods for manufacturing a medicament comprising, combining at least one disclosed compound or at least one disclosed product with a pharmaceutically acceptable carrier or diluent. In another embodiment, the present disclosure relates to the use of a disclosed compound in the manufacture of a medicament for the treatment of a disorder associated with an ENPP1 activity dysfunction, CdnP activity dysfunction, or both. In another embodiment, the present disclosure relates to the uses of disclosed compounds in the manufacture of a medicament for the treatment of a disorder of uncontrolled cellular proliferation.

Also disclosed are uses of a disclosed compound or a disclosed product in the manufacture of a medicament for the treatment of a disorder associated with an ENPP1 dysfunction in a mammal.

The present disclosure also provides a method for the treatment of a disorder of uncontrolled cellular proliferation in a mammal, the method comprising the step of administering to the mammal an effective amount of any of the compounds of the present disclosure.

The present disclosure also provides a method for decreasing ENPP1 activity, CdnP activity, or both in a mammal, the method comprising the step of administering to the mammal an effective amount of any of the compounds of the present disclosure.

The present disclosure also provides a method for inhibiting ENPP1 activity, CdnP activity, or both in a mammal, the method comprising the step of administering to the mammal an effective amount of any of the compounds of the present disclosure (i.e., a compound of Structure (I) or Structure (II) or Structure (III)).

In the treatment conditions which require inhibition or negative modulation of ENPP1 protein activity an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted-to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present disclosure is further directed to a method for the manufacture of a medicament for inhibiting or negatively modulating ENPP1 protein activity, CdnP protein activity, or both (e.g., treatment of a disorder of uncontrolled cellular proliferation, or one or more neurodegenerative disorders associated with ENPP1 and/or CdnP dysfunction)

in mammals (e.g., humans) comprising combining one or more disclosed compounds, products, or compositions with a pharmaceutically acceptable carrier or diluent. Thus, in one embodiment, this disclosure relates to a method for manufacturing a medicament comprising combining at least one disclosed compound or at least one disclosed product with a pharmaceutically acceptable carrier or diluent.

The compounds disclosed herein are useful for treating, preventing, ameliorating, controlling or reducing the risk of a variety of disorders wherein the patient or subject would benefit from inhibition or negative modulation of ENPP1, CdnP, or both. In one embodiment is provided a method of treating or preventing a disorder in a subject comprising the step of administering to the subject at least one disclosed compound; at least one disclosed pharmaceutical composition; and/or at least one disclosed product in a dosage and amount effective to treat the disorder in the subject.

Also provided is a method for the treatment of one or more disorders, for which ENPP1/CdnP inhibition is predicted to be beneficial, in a subject comprising the step of administering to the subject at least one disclosed compound; at least one disclosed pharmaceutical composition; and/or at least one disclosed product in a dosage and amount effective to treat the disorder in the subject.

In another embodiment, provided is a method for treating a disorder of uncontrolled cellular proliferation, comprising: administering to a subject at least one disclosed compound; at least one disclosed pharmaceutical composition; and/or at least one disclosed product in a dosage and amount effective to treat the disorder in the subject. In another embodiment, provided is a method for treating or preventing a neurodegenerative disorder, comprising: administering to a subject at least one disclosed compound; at least one disclosed pharmaceutical composition; and/or at least one disclosed product in a dosage and amount effective to treat the disorder in the subject. Also provided is a method for the treatment of a disorder in a mammal comprising the step of administering to the mammal at least one disclosed compound, composition, or medicament.

The present disclosure is directed at the use of described chemical compositions to treat diseases or disorders in patients (preferably human) wherein ENPP1 inhibition would be predicted to have a therapeutic effect, such as disorders of uncontrolled cellular proliferation (e.g., cancers), neurodegenerative disorders such as Alzheimer's disease, Huntington's disease, and Parkinson's disease, diseases caused by bacteria and/or viruses, by administering one or more disclosed compounds or products.

The compounds of the present disclosure can also be used for immunotherapy.

In one embodiment, the compounds of the present disclosure treat disorders of uncontrolled cellular proliferation, and/or diseases caused by bacteria and/or viruses through immunotherapy, meaning that the compounds elicit immunotherapeutic response which results in the treatment of these diseases.

The compounds disclosed herein are useful for treating, preventing, ameliorating, controlling or reducing the risk of a variety of disorders of uncontrolled cellular proliferation.

Also provided is a method of use of a disclosed compound, composition, or medicament. In one embodiment, the method of use is directed to the treatment of a disorder. In another embodiment, the disclosed compounds can be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

Examples of disorders treatable with the provided compounds include a disorder of uncontrolled cellular proliferation. In an embodiment, the disorder of uncontrolled cellular proliferation is cancer. In a specific embodiment, the cancer is a leukemia. In another specific embodiment, the cancer is a sarcoma. In yet another specific embodiment, the cancer is a solid tumor. In another specific embodiment, the cancer is a lymphoma.

It is understood that cancer refers to or describes the physiological condition in mammals that is typically characterized by unregulated cell growth. The cancer may be multi-drug resistant (MDR) or drug-sensitive. Examples of cancer include, but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer.

In various other embodiments, further examples of cancers are basal cell carcinoma, biliary tract cancer; bone cancer; brain and CNS cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas In another embodiment, the cancer is a hematological cancer. In yet another embodiment, the hematological cancer is selected from acute myeloid leukemia (AML), acute lymphoblastic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), Hodgkin lymphoma, Non-Hodgkin lymphoma, multiple myeloma, solitary myeloma, localized myeloma, and extramedullary myeloma. In yet another embodiment, the cancer is selected from chronic lymphocytic leukemia, small lymphocytic lymphoma, B-cell non-Hodgkin lymphoma, and large B-cell lymphoma.

In another embodiment, the cancer is a cancer of the brain. In a specific embodiment, the cancer of the brain is selected from a glioma, medulloblastoma, primitive neuroectodermal tumor (PNET), acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, and metastatic brain tumor. In a yet another embodiment, the glioma is selected from ependymoma, astrocytoma, oligodendroglioma, and oligoastrocytoma. In yet another embodiment, the glioma is selected from juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, multifocal gliomatous tumor, multicentric glioblastoma multiforme tumor, paraganglioma, and ganglioglioma.

In one embodiment, the cancer can be a cancer selected from cancers of the blood, brain, genitourinary tract, gastrointestinal tract, colon, rectum, breast, kidney, lymphatic system, stomach, lung, pancreas, and skin. In another embodiment, the cancer is selected from prostate cancer, glioblastoma multiforme, endometrial cancer, breast cancer, and colon cancer. In another embodiment, the cancer is selected from a cancer of the breast, ovary, prostate, head, neck, and kidney. In yet another embodiment, the cancer is selected from cancers of the blood, brain, genitourinary tract, gastrointestinal tract, colon, rectum, breast, liver, kidney, lymphatic system, stomach, lung, pancreas, and skin. In another embodiment, the cancer is selected from a cancer of the lung and liver. In still another embodiment, the cancer is selected from a cancer of the breast, ovary, testes and prostate.

In other embodiments, disorders associated with an ENPP1 dysfunction include neurodegenerative disorders. In another embodiment, the neurodegenerative disease is selected from Alzheimer's disease, Parkinson's disease, and Huntington's disease.

The compounds are further useful in a method for the prevention, treatment, control, amelioration, or reduction of risk of the diseases, disorders and conditions noted herein. The compounds are further useful in a method for the prevention, treatment, control, amelioration, or reduction of risk of the aforementioned diseases, disorders and conditions in combination with other agents.

The present disclosure is further directed to administration of an ENPP1 inhibitor for improving treatment outcomes in the context of disorders of uncontrolled cellular proliferation, including cancer. That is, in one embodiment, this disclosure relates to a co-therapeutic method comprising the step of administering to a mammal an effective amount and dosage of at least one compound of the present disclosure in combination with cancer therapy.

In another embodiment, administration improves treatment outcomes in the context of cancer therapy. Administration in connection with cancer therapy can be continuous or intermittent. Administration need not be simultaneous with therapy and can be before, during, and/or after therapy. For example, cancer therapy can be provided within 1, 2, 3, 4, 5, 6, 7 days before or after administration of the compound. As a further example, cancer therapy can be provided within 1, 2, 3, or 4 weeks before or after administration of the compound. As a still further example, cognitive or behavioral therapy can be provided before or after administration within a period of time of 1, 2, 3, 4, 5, 6, 7, 8, 9, or 10 half-lives of the administered compound.

In an embodiment, the disclosed compounds can be used in combination with one or more other drugs in the treatment, prevention, control, amelioration, or reduction of risk of diseases or conditions for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present disclosure. When a compound of the present disclosure is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly.

Accordingly, the pharmaceutical compositions include those that contain one or more other active ingredients, in addition to a compound of the present disclosure.

The above combinations include combinations of a disclosed compound not only with one other active compound, but also with two or more other active compounds. Likewise, disclosed compounds can be used in combination with other drugs that are used in the prevention, treatment, control, amelioration, or reduction of risk of the diseases or conditions for which disclosed compounds are useful. Such other drugs can be administered, by a route and in an amount commonly used therefor, contemporaneously or sequentially with a compound of the present disclosure. When a compound of the present disclosure is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present disclosure.

The weight ratio of a disclosed compound to the second active ingredient can be varied and will depend upon the effective dose of each ingredient. Generally, an effective dose of each will be used. Thus, for example, when a compound of the present disclosure is combined with another agent, the weight ratio of a disclosed compound to the other agent will generally range from about 1000:1 to about 1;1000, preferably about 200:1 to about 1:200. Combinations of a compound of the present disclosure and other active ingredients will generally also be within the aforementioned range, but in each case, an effective dose of each active ingredient should be used.

In such combinations a disclosed compound and other active agents can be administered separately or in conjunction. In addition, the administration of one element can be prior to, concurrent to, or subsequent to the administration of other agent(s).

Accordingly, the subject compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent can be coadministered, either in concomitant therapy or in a fixed combination.

In one embodiment, the compound can be employed in combination with anti-cancer therapeutic agents or other known therapeutic agents.

In the treatment of conditions which require inhibition or negative modulation of ENPP1, an appropriate dosage level will generally be about 0.01 to 1000 mg per kg patient body weight per day which can be administered in single or multiple doses. Preferably, the dosage level will be about 0.1 to about 250 mg/kg per day; more preferably about 0.5 to about 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Thus, in one embodiment, the present disclosure relates to methods for inhibiting or negatively modulating ENPP1 in at least one cell, comprising the step of contacting the at least one cell with at least one compound of the disclosure, in an amount effective to modulate or activate ENPP1 activity response, e.g., in the at least one cell. In another embodiment, the cell is mammalian, for example human. In another embodiment, the cell has been isolated from a subject prior to the contacting step. In another embodiment, contacting is via administration to a subject.

In one embodiment, the present disclosure relates to methods for inhibiting or negatively modulating CdnP in at least one cell, comprising the step of contacting the at least one cell with at least one compound of the disclosure, in an amount effective to modulate or activate CdnP activity response, e.g., in the at least one cell. In another embodiment, the cell is mammalian, for example human. In another embodiment, the cell has been isolated from a subject prior to the contacting step. In another embodiment, contacting is via administration to a subject.

Methods of Preparation

Compounds of Structure (I), (II), or (III) can be prepared according to methods known in the art and according to methods disclosed herein. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)).

General Reaction Scheme 1

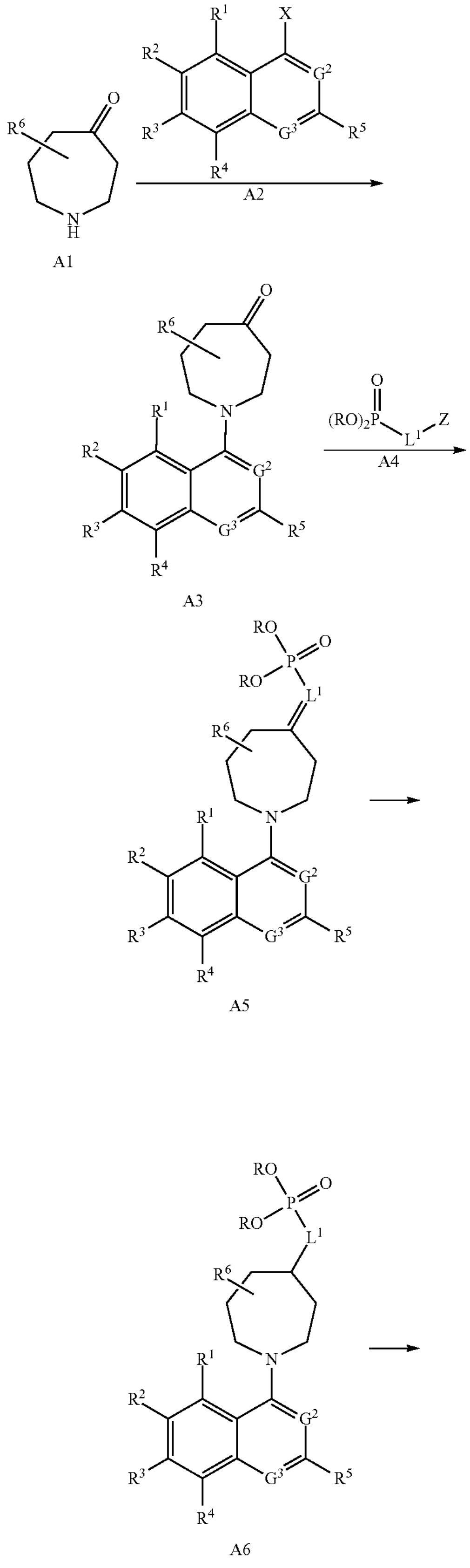

-continued

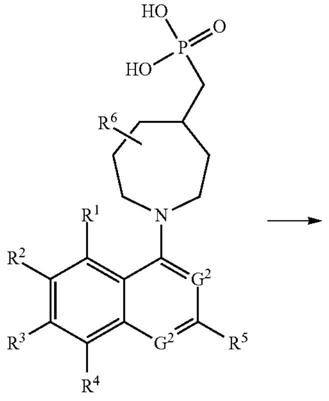

A7

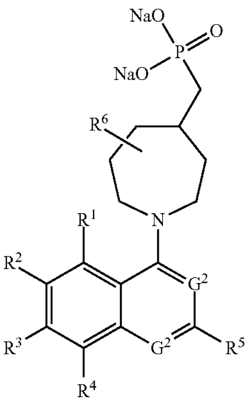

A8

General Reaction Scheme 1 provides an exemplary method for the preparation of compounds of structure (I), wherein $R^{7a}$ is O, and $R^{7b}$ and $R^{7c}$ are each, independently —$O^-$ or —OH. $L^1$, $G^2$, $G^3$, $R^1$, $R^2$, $R^3$, $R^4$, $R^5$ and $R^6$ in General Reaction Scheme 1 are as defined herein. The X group on A2 is a reactive moiety selected to facilitate the base promoted coupling reaction between A1 and A2 (e.g., where X is Br, Cl or OTf and the base used in the reaction is, for example, TEA or $K_2CO_3$). The Z group on A4 represents a transient functional group capable of promoting the condensation reaction between A3 and A4 to provide A5 (e.g., where A4 is tetraethyl methylenediphosphonate and the reaction takes place in the presence of base, for example NaH, or KOtBu). A5 is reduced under standard conditions (e.g., $H_2$, Pd/C) to provide A6 which undergoes hydrolysis to provide phosphonic acid A7, using, for example TMS-Br in DCM or NaBr and TMS-Cl in NMP. Conversion of A7 to salt A8, wherein $M^+$ represents an appropriate cationic specie, can be accomplished, for example, by treating A7 with an appropriate base (e.g., NaOH, wherein $M^+$ is $Na^+$). Compounds A7 and A8 are each compounds of structure (I).

General Reaction Scheme 2

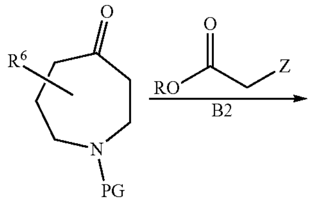

B1

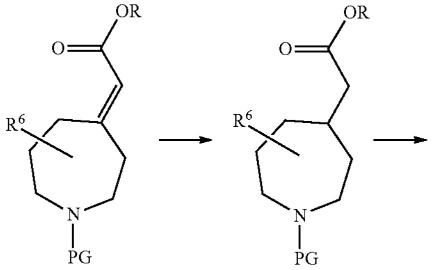

B3 B4

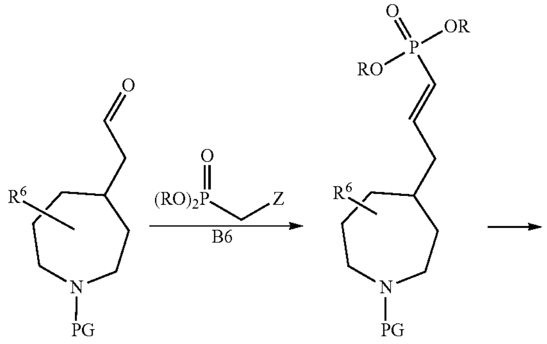

B5 B7

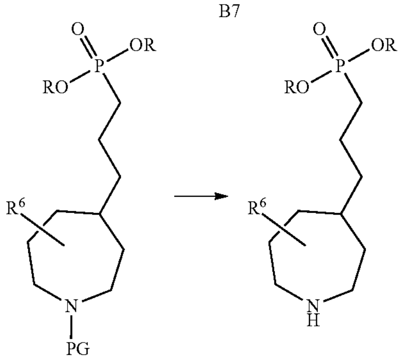

B8 B9

General Reaction Scheme 2 provides an exemplary method for the preparation of precursors of compounds of structure (I), wherein $R^{7a}$ is O, and $R^{7b}$ and $R^{7c}$ are each, independently, —$O^-$ or —OH. $R^6$ in General Reaction Scheme 2 is as defined herein. Compound B1 contains a protecting group (PG) on the nitrogen atom to attenuate its reactivity. PG can be selected (and, alternatively, modified if necessary) based on compatibility with other synthetic steps (e.g., the conditions required to couple B5 and B6 to form B7) in view of the entire reaction scheme. PG may include, but is not limited to, Boc, benzyl, DMB, or Cbz. The Z group on B2 represents a transient functional group capable of promoting the condensation reaction between B1 and B2 to provide B3 (e.g., where B2 is ethyl 2-(diethoxyphosphoryl) acetate and the reaction takes place in the presence of base, for example NaH, or KOtBu). B3 is reduced under standard conditions (e.g., $H_2$, Pd/C) to provide B4 which undergoes further reduction to provide aldehyde B5, using, for example DIBAL-H in DCM at −78° C. Another Z group promoted condensation between B5 and B6 provides unsaturated phosphonate B7 (e.g., where B6 is tetraethyl methylenediphosphonate and the reaction takes place in the presence of base, for example NaH, or KOtBu). B7 is reduced under standard conditions (e.g., $H_2$, Pd/C) to provide B8 which is deprotected (e.g., with TFA in $CH_2$—$Cl_2$ if PG is Boc) to provide secondary amine B9.

One of skill in the art will recognize the utility of General Reaction Scheme 2 to provide a facile method of synthesizing compounds of structure (I) with varying $L^1$ groups, as described herein. One of ordinary skill will be able to select a desired $L^1$ group by making modifications to the above sequence through the judicious selection of reagents and substrates to obtain secondary amine precursor B9. Compounds of structure (I) can be prepared from B9 using coupling methods described herein, and as shown below in General Reaction Scheme 3.

General Reaction Scheme 3

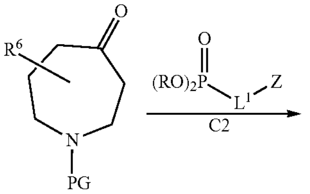

C1

C2

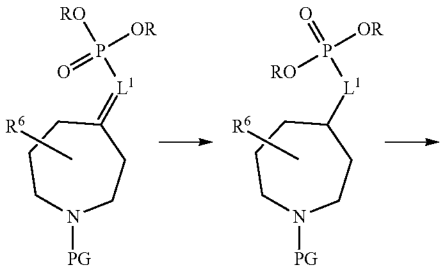

C3

C4

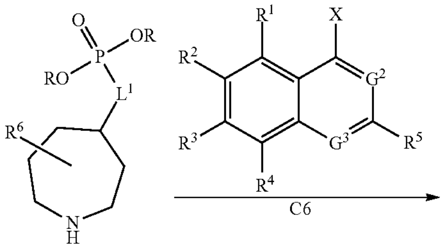

C6

C5

-continued

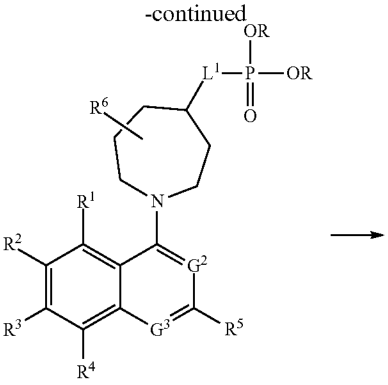

C7

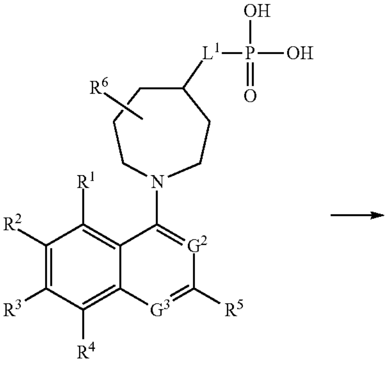

C8

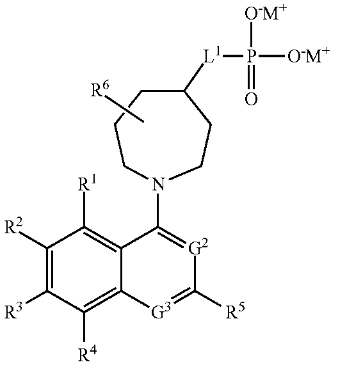

C9

General Reaction Scheme 3 provides an exemplary method for the preparation of compounds of structure (I), wherein $R^{7a}$ is O, and $R^{7b}$ and $R^{7c}$ are each, independently —$O^-$ or —OH. $L^1$, $G^2$, $G^3$, $R^1$, $R^2$, $R^3$, $R^4$, $R^5$ and $R^6$ in General Reaction Scheme 1 are as defined herein. Heterocycle C1 contains a protecting group (PG) on the nitrogen atom to attenuate its reactivity. PG can be selected (and, alternatively, modified if necessary) based on compatibility with other synthetic steps (e.g., the conditions required to couple C1 and C2 to form C3) in view of the entire reaction scheme. PG may include, but is not limited to, Boc, benzyl, DMB, or Cbz. The Z group on C2 represents a transient functional group capable of promoting the condensation reaction between C1 and C2 to provide C3 (e.g., where C2 is tetraethyl methylenediphosphonate and the reaction takes place in the presence of base, for example NaH, or KOtBu). C3 is reduced under standard conditions (e.g., $H_2$, Pd/C) to provide C4 which is subsequently deprotected (e.g., with TFA in $CH_2Cl_2$ if PG is Boc) to provide secondary amine C5. The X group on C6 is a reactive moiety selected to facilitate the desired base promoted coupling reaction between C5 and C6 (e.g., where X is Br, C1 or OTf and the base used in the reaction is, for example, TEA or $K_2CO_3$) to provide C7. Compound C7 then undergoes hydrolysis to provide phosphonic acid C8, using for example, TMS-Br in DCM; or NaBr and TMS-C1 in NMP. Conversion of C8 to salt C9, wherein $M^+$ represents an appropriate cationic specie, is can be accomplished, for example, by treating A7 with an appropriate base (e.g., NaOH, wherein $M^+$ is $Na^+$). Compounds C8 and C9 are each compounds of structure (I).

It should be noted that various alternative strategies for preparation of compounds of Structure (I) or (III) are available to those of ordinary skill in the art. For example, other compounds of Structure (I) or (III) can be prepared according to analogous methods using the appropriate starting material. It will also be appreciated by those skilled in the art that in the processes for preparing the compounds of Structure (I) or (III), the functional groups of intermediate compounds may need to be protected by suitable protecting groups. Such functional groups include, but are not limited to, hydroxy, amino, mercapto and carboxylic acid.

Compound of Structure (III) can be made using various strategies available to those of ordinary skill in the art; namely, as outlined in PCT Publication No. WO 2019/051269, which is hereby incorporated by reference in its entirety.

General Reaction Scheme 4

Example conversion of $G_1$

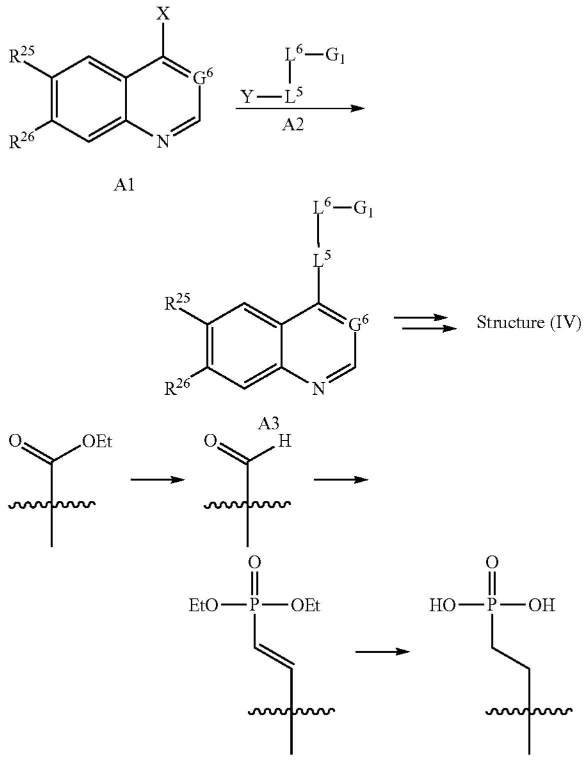

A1

A3

General Reaction Scheme 1 provides an exemplary method for the preparation of compounds of structure (II) wherein $G^6$, $L^5$, $L^6$, $R^{25}$ and $R^{26}$ are as defined herein. Compounds A1 and A2 are commercially available or prepared according to methods known in the art. $G_1$ is a functional group able to withstand the conditions of the reaction scheme and which can be converted, through removal of protecting groups, or additional chemical conversion(s) to provide a compound of structure (II). The X group on A1 and the Y group on A2 are complementary reactive moieties selected to facilitate the coupling reaction between A1 and A2 to give the coupled product A3. Depending on the nature of $G_1$, one or more steps may be required to convert A3 to a compound of Structure (II).

In some instances, X is a halogen atom or a reactive equivalent (e.g., Cl, Br, OTf) and Y is —OH and the coupling reaction proceeds under basic conditions (e.g., NaH in dioxane) to afford A3.

In other instances, X is a halogen atom or a reactive equivalent (e.g., Cl, Br, OTf) and Y is $—NH_2$ and the coupling reaction proceeds under basic conditions (e.g., excess amine in TIF) to afford A3.

In still more instances, X is thiol group (—SH) and Y is a halogen atom or a reactive equivalent (e.g., Cl, Br, OTf) and the coupling reaction proceeds under basic conditions (e.g., $K_2CO_3$ in DMF, or NaH in THF) to afford A3.

In some instances, X is a halogen atom or a reactive equivalent (e.g., Cl, Br, OTf) and Y is $—NHR_x$, where in $R_x$ is alkyl, and the coupling reaction proceeds under basic conditions (e.g., $K_2CO_3$ in DMF, or NaH in dioxane) to afford A3.

In other instances, X is a halogen atom or a reactive equivalent (e.g., Cl, Br, OTf) and Y is a boronic acid, a boronic acid ester, or trifluoroborate salt (e.g., $—B^-F_3K^+$) and the reaction proceeds under palladium catalyzed cross coupling conditions (e.g., $Pd(dppf)Cl_2$, $Na_2CO_3$ in dioxane: $H_2O$, or XPhos Pd G2, $K_3PO_4$ in THF:$H_2O$) to afford A3

It should be noted that various alternative strategies for preparation of compounds of Structure (II) are available to those of ordinary skill in the art. For example, other compounds of Structure (II) can be prepared according to analogous methods using the appropriate starting material. It will also be appreciated by those skilled in the art that in the processes for preparing the compounds of Structure (II), the functional groups of intermediate compounds may need to be protected by suitable protecting groups. Such functional groups include, but are not limited to, hydroxy, amino, mercapto and carboxylic acid.

Suitable protecting groups for hydroxy include, but are not limited to, trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl ("Boc"), benzyloxycarbonyl, and the like. Protecting groups are optionally added or removed in accordance with standard techniques, which are known to one skilled in the art and as described herein. The use of protecting groups is described in detail in Green, T. W. and P. G. M. Wutz, Protective Groups in Organic Synthesis (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this disclosure may not possess pharmacological activity as such, they may be administered to a mammal and thereafter metabolized in the body to form compounds of the disclosure which are pharmacologically active. Such derivatives may therefore be described as "prodrugs". Prodrugs of compounds of this disclosure are included within the scope of embodiments of the disclosure.

The examples and preparations provided below further illustrate and exemplify the compounds of Structure (I) and methods of preparing such compounds. It is to be understood that the scope of the present disclosure is not limited in any way by the scope of the following examples and preparations. In the following examples, and throughout the specification and claims, molecules with a single stereocenter, unless otherwise noted, exist as a racemic mixture. Those molecules with two or more stereocenters, unless otherwise noted, exist as a racemic mixture of diastereomers. Single enantiomers/diastereomers may be obtained by methods known to those skilled in the art.

EXAMPLES

The following examples are provided for exemplary purposes. Other compounds of Structure (I) exemplified in Table 1 were prepared according to analogous procedures, routine in the art. For examples below which result in a compound of Structure (I), General Reaction Scheme I, as described above, was generally used, unless otherwise noted.

Example 1

Synthesis of (((2-(1-(6,7-dimethoxyquinazolin-4-yl)piperidin-4-yl)ethyl)phosphoryl)bis(oxy))bis(methylene) bis(2-methylpropanoate) (compound 1-3)

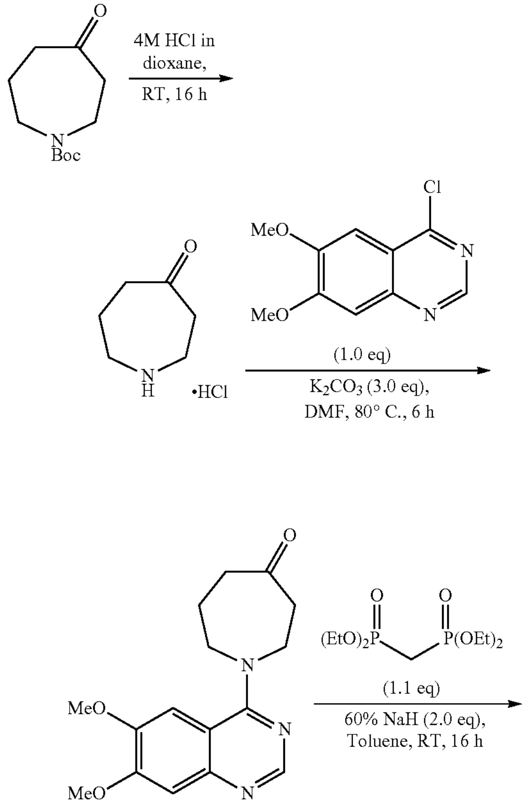

-continued

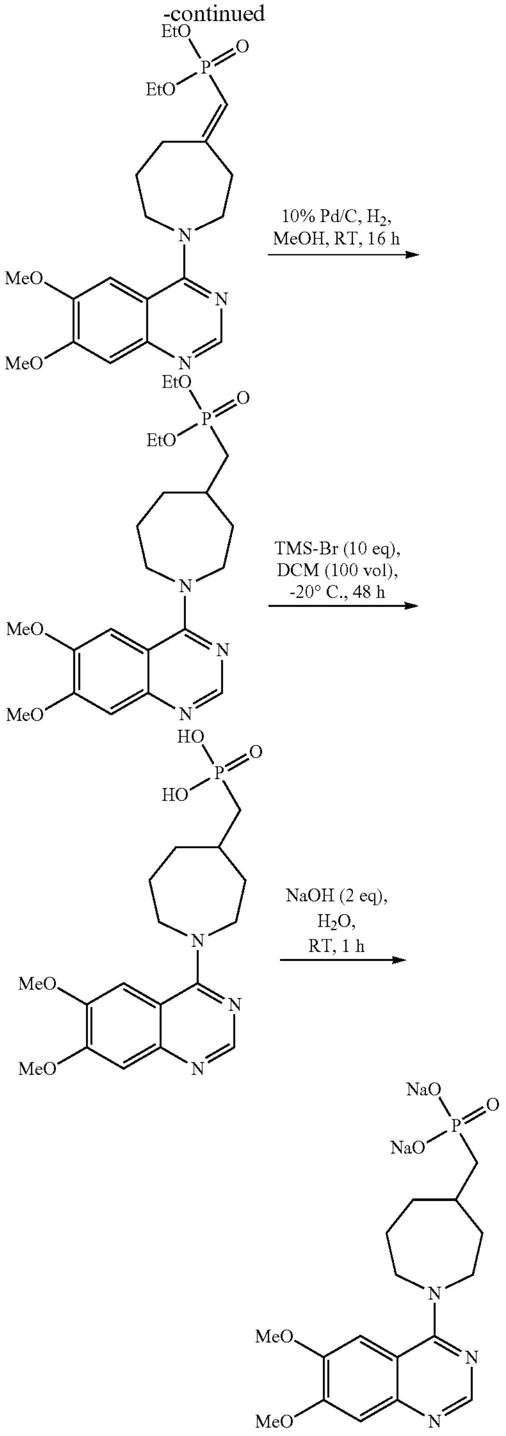

Synthesis of Azepan-4-one hydrochloride

To a stirred solution of tert-butyl 4-oxoazepane-1-carboxylate (3 g, 14.08 mmol) in 1,4-dioxane (10 mL) was added 4M HCl in dioxane (5.0 mL) at RT, and the reaction stirred at RT for 16 h. The progress of the reaction was monitored by TLC. After completion of the reaction, the mixture was concentrated under reduced pressure to afford the crude compound. The crude material was triturated with ether to obtain azepan-4-one hydrochloride (1.5 g, 10.06 mmol, 71% yield) as a light brown solid.

$^1$H NMR: (400 MHz, DMSO) 9.45 (s, 2H), 3.19-3.36 (m, 4H), 2.74-2.77 (m, 2H), 2.59-2.62 (m, 2H), 1.90-1.96 (m, 2H).

Synthesis of 1-(6,7-dimethoxyquinazolin-4-yl)azepan-4-one

To a stirred solution of 4-chloro-6,7-dimethoxyquinazoline (2 g, 8.9 mmol) in DMF (20 mL) was added potassium carbonate (3 g, 22.25 mmol) and azepan-4-one hydrochloride (1.5 g, 13.35 mmol) and the reaction was stirred at 80° C. for 6 h. The progress of the reaction was monitored by TLC. After completion of the reaction, water was added (100 mL) and the mixture was extracted with ethyl acetate (2×50 mL). The combined organic phase was washed with brine (50 mL), dried over sodium sulfate and concentrated under reduced pressure. The crude material was purified through combi flash chromatography to afford pure 1-(6,7-dimethoxyquinazolin-4-yl)azepan-4-one (950 mg, 3.15 mmol, 35% yield) as a light yellow solid.

$^1$H NMR: (400 MHz, DMSO) δ 8.44 (s, 1H), 7.17 (s, 1H), 7.12 (s, 1H), 3.99 (t, 2H), 3.86-3.90 (m, 8H), 2.82-2.85 (m, 2H), 2.62-2.65 (m, 2H), 2.03-2.05 (m, 2H).

LCMS: $(M+H)^+$: m/Z: 302.2.

Synthesis of Diethyl (E)-((1-(6,7-dimethoxyquinazolin-4-yl)azepan-4-ylidene)methyl)phosphonate To a stirred solution of tetraethyl methylenebis(phosphonate) (0.545 mL, 2.19 mmol) in toluene (6 mL) was added 60% NaH (159 mg, 3.98 mmol) at 0° C. and the mixture stirred for 15 min, then 1-(6,7-dimethoxyquinazolin-4-yl) azepan-4-one (600 mg, 1.99 mmol) was added at 0° C. in one portion. The reaction mixture was stirred at RT for 16 h. The progress of the reaction was monitored by TLC. After completion of the reaction, water was added (50 mL) and the mixture was extracted with ethyl acetate (2×20 mL). The combined organic phase was washed with brine (10 mL), dried over sodium sulfate and concentrated under reduced pressure. The crude material was purified through combi flash chromatography to afford pure diethyl (E)-((1-(6,7-dimethoxyquinazolin-4-yl)azepan-4-ylidene)methyl)phosphonate (300 mg, 0.689 mmol, 35% yield) as a pale brown solid.

LCMS: $(M+H)^+$: m/Z: 436.4.

Synthesis of diethyl ((1-(6,7-dimethoxyquinazolin-4-yl)azepan-4-yl)methyl)phosphonate To a stirred solution of diethyl (E)-((1-(6,7-dimethoxyquinazolin-4-yl)azepan-4-ylidene)methyl)phosphonate (300 mg, 0.68 mmol) in methanol (15 mL) was added 10% Pd/C (60 mg) and the reaction mixture was stirred under balloon hydrogen atmosphere at room temperature for 16 h. The progress of the reaction was monitored by TLC. After completion of the reaction, the mixture was filtered through Celite and the filter bed was washed with 5% methanol in dichloromethane (50 mL). The filtrate was concentrated under reduced pressure to afforded diethyl ((1-(6,7-dimethoxyquinazolin-4-yl)azepan-4-yl)methyl)phosphonate (500 mg, 1.689 mmol, 98% yield) as a yellow solid.

$^1$H NMR: (400 MHz, DMSO) δ 8.37 (s, 1H), 7.3 (s, 1H), 7.14 (s, 1H), 4.07 (m, 4H), 3.97-3.98 (m, 6H), 2.5 (s, 1H), 2.4 (m, 2H), 2.2 (m, 2H), 1.38 (m, 2H), 1.94-1.90 (m, 2H), 1.78-1.72 (m, 2H), 1.27-1.19 (m, 6H).

LCMS: $(M+H^+)$: m/Z: 438.4

Synthesis of ((1-(6,7-dimethoxyquinazolin-4-yl) azepan-4-yl)methyl)phosphonic acid To a stirred solution of diethyl ((1-(6,7-dimethoxyquinazolin-4-yl)azepan-4-yl)methyl)phosphonate (400 mg, 0.915 mmol) in DCM (100 vol) was added TMS-Br (1.2 mL, 10.0 eq) at −20° C. dropwise. The reaction mixture was stirred at room temperature for 48 h. After completion of the reaction (monitored by TLC), excess solvent was evaporated under reduced pressure to provide the crude product. The crude material was washed with ether to afford ((1-(6,7-dimethoxyquinazolin-4-yl)azepan-4-yl)methyl)phosphonic acid (250 mg, 0.656 mmol, 71% yield) as a pale brown solid

$^1$H NMR: (400 MHz, DMSO) δ 8.73 (s, 1H), 7.48 (s, 1H), 7.17 (s, 1H), 4.27-4.31 (m, 2H), 3.96 (s, 3H),), 3.92 (s, 3H), 3.85-3.89 (m, 2H), 2.31-2.32 (m, 1H), 2.03-2.05 (m, 1H), 2.02-1.91 (m, 3H), 2.0 (m, 2H), 2.0 (m, 2H), 1.27-1.29 (m, 1H).

LCMS: $(M+H)^+$: m/Z: 382.0.

Synthesis of Sodium ((1-(6,7-dimethoxyquinazolin-4-yl)azepan-4-yl)methyl) phosphonate (I-3)

To a stirred solution of ((1-(6,7-dimethoxyquinazolin-4-yl)azepan-4-yl)methyl) phosphonic acid (25 mg, 0.065 mmol) in $H_2O$ (2 mL) at 0° C. was added NaOH (5 mg, 1.8 eq). The reaction mixture was stirred at room temperature for 1 h, then the reaction mixture was kept under lyophilization to afford I-3 (26 mg, 0.027 mmol, 96% yield) as a pale brown solid.

$^1$H NMR: (400 MHz, DMSO) δ 8.03 (s, 1H), 6.69-6.84 (m, 2H), 3.81-3.82 (m, 3H), 3.82-3.84 (m, 5H), 3.47-3.63 (m, 2H),), 2.11 (m, 1H), 2.0 (m, 2H), 1.8 (brs, 2H), 1.5 (m, 1H), 1.36 (dd, 2H), 1.12-1.21 (m, 1H).

LCMS: $(M+H)^+$: m/Z: 382.3.

Example 2

Synthesis of Sodium (3-(1-(6,7-dimethoxyquinazolin-4-yl)azepan-4-yl)propyl)phosphonate (Compound i-5)

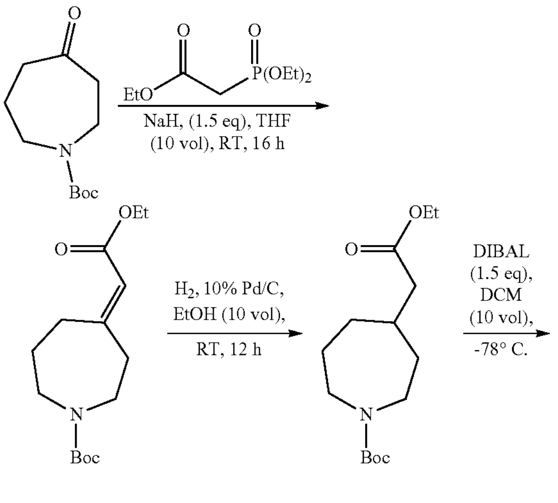

-continued

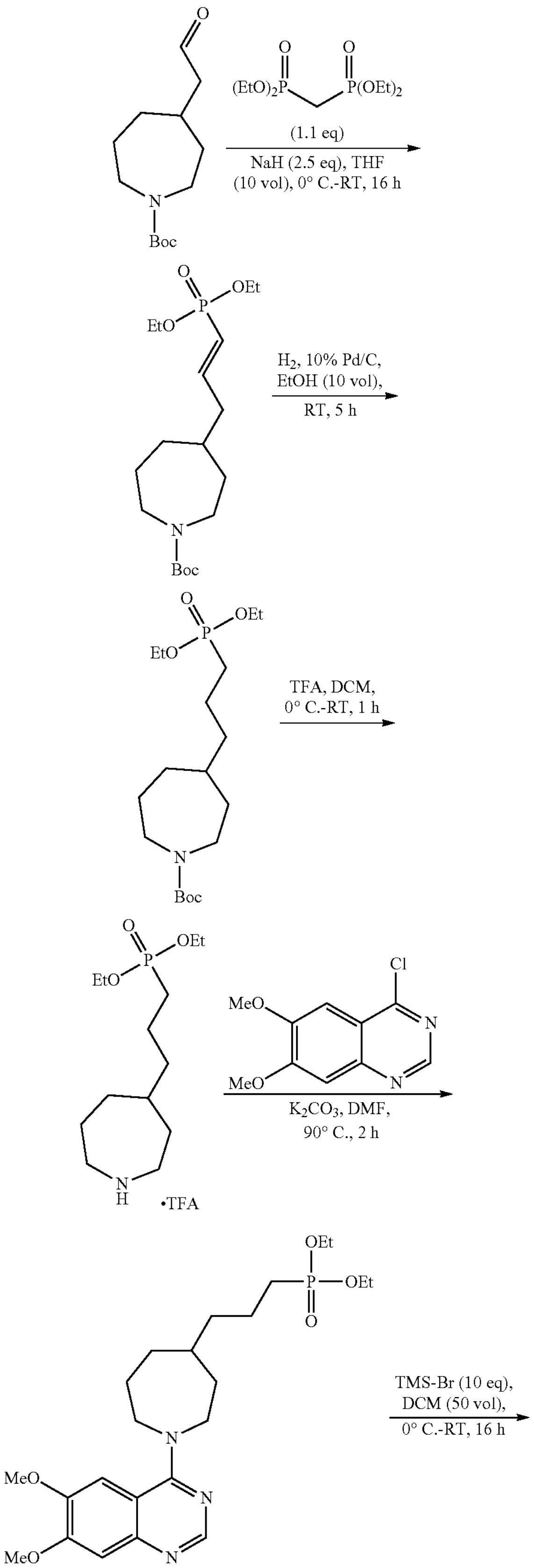

-continued

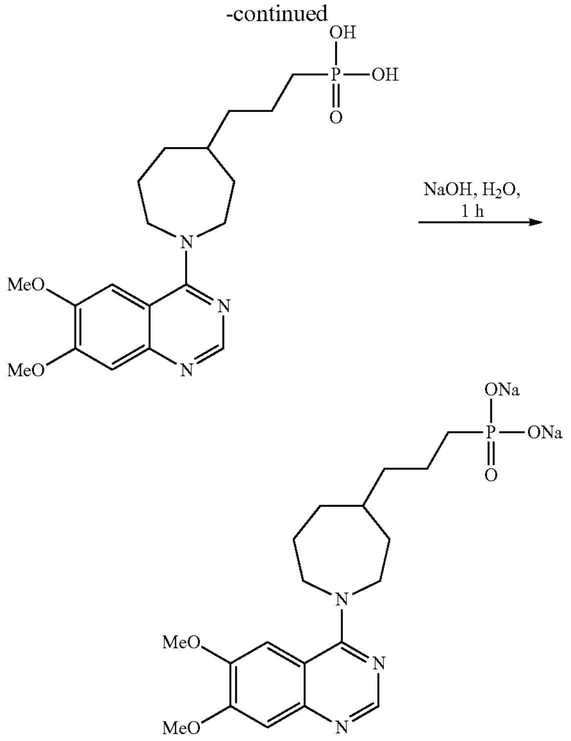

Synthesis of tert-butyl (E)-4-(2-ethoxy-2-oxoethylidene)azepane-1-carboxylate To a stirred solution of ethyl 2-(diethoxyphosphoryl) acetate (31 g, 140.8 mmol) in tetrahydrofuran (70 mL) was added 60% NaH (3.7 g, 93.9 mmol) at 0° C. and the mixture was stirred for 30 min, then tert-butyl 4-oxoazepane-1-carboxylate (10 g, 46.95 mmol) was added at 0° C. portion wise. The reaction mixture was stirred at room temperature for 16 h. The progress of the reaction was monitored by TLC. After completion of the reaction, water was added (500 mL) and the mixture was extracted with ethyl acetate (2×300 mL). The combined organic phase was washed with brine (400 mL), dried over sodium sulfate and concentrated under reduced pressure to afford the crude compound. The crude material was purified through combi-flash chromatography, eluting with 10% ethyl acetate in pet. ether to afford pure tert-butyl (E)-4-(2-ethoxy-2-oxoethylidene)azepane-1-carboxylate (8 g, 28.26 mmol, 61% yield) as a colorless oily liquid.

$^1$H NMR: (400 MHz, DMSO) δ 5.683-5.770 (m, 1H), 4.138-4.192 (m, 2H), 3.351-3.521 (m, 5H), 3.063-3.092 (m, 1H), 2.819-2.833 (m, 1H), 2.516-2.543 (m, 1H), 2.383-2.412 (m, 1H), 1.754-1.830 (m, 2H), 1.451 (s, 9H), 1.265-1.313 (m, 3H).

Synthesis of tert-butyl 4-(2-ethoxy-2-oxoethyl)azepane-1-carboxylate

To a stirred solution of tert-butyl (E)-4-(2-ethoxy-2-oxoethylidene)azepane-1-carboxylate (4.1 g, 14.49 mmol) in ethanol (50 mL) was added 10% Pd/C (500 mg, 10% w/w) and the reaction mixture was stirred under balloon hydrogen atmosphere at room temperature for 16 h. The progress of the reaction was monitored by TLC. After completion of the reaction, the mixture was filtered through Celite and the filter bed was washed with 10% methanol in dichloromethane (50 mL). The filtrate was concentrated under reduced pressure to afford tert-butyl 4-(2-ethoxy-2-oxoethyl) azepane-1-carboxylate (2 g, 7.017 mmol, 48% yield) as a colorless oily liquid.

$^1$H NMR: (400 MHz, DMSO) δ 3.901-4.053 (m, 2H), 3.086-3.432 (m, 2H), 1.651-1.978 (m, 3H), 1.320-1.535 (m, 6H), 1.145-1.264 (m, 5H), 0.797-0.842 (m, 1H).

Synthesis of tert-butyl 4-(2-oxoethyl) azepane-1-carboxylate

To a stirred solution of tert-butyl 4-(2-ethoxy-2-oxoethyl) azepane-1-carboxylate (2 g, 7.017 mmol) in dichloromethane (40 mL) was added 1M DIBAL-H (10.5 mL, 10.5 mmol) at −78° C. and the reaction mixture was stirred for 1 h. The progress of the reaction was monitored by TLC. After completion of the reaction, the reaction mixture was quenched with saturated ammonium chloride solution (100 mL) and extracted with dichloromethane (2×100 mL). The combined organic phase was washed with brine (200 mL), dried over sodium sulfate and concentrated under reduced pressure. The crude material was purified through combiflash chromatography, eluting with 20% ethyl acetate in pet. ether to afford tert-butyl 4-(2-oxoethyl) azepane-1-carboxylate (700 mg, 2.904 mmol, 41% yield) as a colorless oily liquid.

$^1$H NMR: (400 MHz, DMSO) δ 9.775 (s, 1H), 3.155-3.831 (m, 7H), 2.410-2.427 (d, 2H), 2.327-2.345 (d, 1H), 2.033-2.095 (bs, 1H), 1.823-1.869 (m, 4H), 1.702-1.757 (m, 1H), 1.486 (s, 9H), 1.267-1.327 (m, 2H).

Synthesis of tert-butyl (E)-4-(3-(diethoxy phosphoryl) allyl) azepane-1-carboxylate To a stirred solution of tetraethyl methylene bis(phosphonate) (1.25 g, 4.357 mmol) in toluene (10 mL) was added 60% NaH (174 mg, 2.904 mmol) at 0° C. and the mixture was stirred for 30 min, then tert-butyl 4-(2-oxoethyl) azepane-1-carboxylate (700 mg, 2.904 mmol) was added at 0° C. portion wise and reaction mixture was stirred at room temperature for 16 h. The progress of the reaction was monitored by TLC. After completion of the reaction, water was added (100 mL) and the mixture was extracted with ethyl acetate (2×100 mL). The combined organic phase was washed with brine (100 mL), dried over sodium sulfate and concentrated under reduced pressure to afford the crude compound of tert-butyl (E)-4-(3-(diethoxy phosphoryl)allyl) azepane-1-carboxylate (1.2 g, crude) as a pale brown oily liquid.

$^1$H NMR: (400 MHz, DMSO) δ 6.675-6.767 (m, 1H), 5.594-5.700 (dt, 1H), 4.036-4.202 (m, 5H), 3.214-3.619 (m, 5H), 2.176-2.2.209 (t, 2H), 1.690-1.890 (m, 4H), 1.459 (s, 9H), 1.309-1.371 (t, 6H).

Synthesis of tert-butyl 4-(3-(diethoxyphosphoryl) propyl)azepane-1-carboxylate To a stirred solution of tert-butyl (E)-4-(3-(diethoxyphosphoryl)allyl)azepane-1-carboxylate (1.2 g, 3.2 mmol) in ethanol (30 mL) was added 10% Pd/C (200 mg, 10% w/w) and the reaction mixture was stirred under balloon hydrogen atmosphere at room temperature for 16 h. The progress of the reaction was monitored by TLC. After completion of the reaction, the mixture was filtered through Celite and the filter bed was washed with 10% methanol in dichloromethane (50 mL). The filtrate was concentrated under reduced pressure to afford tert-butyl 4-(3-(diethoxyphosphoryl)propyl)azepane-1-carboxylate (700 mg, 1.856 mmol, 63% yield over two steps) as a colorless oily liquid.

$^1$H NMR: (400 MHz, DMSO) δ 3.899-3.998 (m, 4H), 3.076-3.442 (m, 4H), 1.610-1.739 (m, 5H), 1.405-1.530 (m, 3H), 1.374 (s, 8H), 1.275-1.287 (m, 2H), 1.184-1.220 (t, 6H), 1.060-1.143 (m, 1H).

Synthesis of diethyl (3-(azepan-4-yl) propyl) phosphonate trifluoroacetate salt To a stirred solution of tert-butyl 4-(3-(diethoxy phosphoryl)propyl)azepane-1-carboxylate (80 mg, mmol) in dichloromethane (2 mL) was added trifluoroaceticacid (0.2 mL) at 0° C., then stirred at room temperature for 3 h. The progress of the reaction was monitored by TLC. After completion of the reaction, the mixture was concentrated under reduced pressure to afford the crude compound of diethyl (3-(azepan-4-yl) propyl) phosphonate trifluoroacetate salt (105 mg, crude) as a pale brown oily liquid.

$^1$H NMR: (400 MHz, DMSO) δ 8.402-8.489 (d, 1H), 3.947-4.042 (m, 3H), 2.903-3.234 (m, 2H), 1.657-1.847 (m, 4H), 1.322-1.560 (m, 5H), 1.214-1.262 (t, 6H).

Synthesis of diethyl (3-(1-(6,7-dimethoxyquinazolin-4-yl)azepan-4-yl)propyl)phosphonate To a stirred solution of 4-chloro-6,7-dimethoxyquinazoline (410 mg, 1.833 mmol) in DMF (10 mL) was added potassium carbonate (760 mg, 5.499 mmol) and diethyl (3-(azepan-4-yl)propyl)phosphonate trifluoroacetate salt (900 mg, 1.833 mmol) and the reaction was stirred at 90° C. for 2 h. The progress of the reaction was monitored by TLC. After completion of the reaction, water was added (100 mL) and the mixture was extracted with ethyl acetate (2×50 mL). The combined organic phase was washed with brine (50 mL), dried over sodium sulfate and concentrated under reduced pressure. The crude material was purified through combi flash chromatography eluting with 5% methanol in dichloromethane to afford pure diethyl (3-(1-(6,7-dimethoxyquinazolin-4-yl)azepan-4-yl)propyl)phosphonate (550 mg, 1.182 mmol, 64% yield) as a brown gummy solid.

$^1$H NMR: (400 MHz, DMSO) δ 8.529 (s, 1H), 7.254-7.264 (d, 1H), 7.206 (s, 1H), 3.965-4.132 (m, 5H), 3.991 (s, 3H), 3.965 (s, 3H), 3.673-3.734 (m, 2H), 3.493 (s, 1H), 2.034-2.071 (m, 2H), 1.869-1.929 (m, 2H), 1.685-1.757 (m, 4H), 1.338-1.427 (m, 2H), 1.261-1.320 (t, 3H).

Synthesis of (3-(1-(6,7-dimethoxyquinazolin-4-yl) azepan-4-yl)propyl)phosphonic acid To a stirred solution of diethyl (3-(1-(6,7-dimethoxyquinazolin-4-yl)azepan-4-yl)propyl)phosphonate (40 mg, 0.086 mmol) in dichloromethane (4 mL) was added TMS-Br (132 mg, 0.860 mmol) at 0° C. dropwise and the reaction mixture was stirred at room temperature for 48 h. After completion of the reaction, the mixture was concentrated under reduced pressure to afford the crude product. The crude material was washed with ether to afford (3-(1-(6,7-dimethoxyquinazolin-4-yl)azepan-4-yl)propyl)phosphonic acid (25 mg, 0.061 mmol, 71% yield) as a brown solid.

LCMS: $(M+H)^+$: m/Z: 410.39.

Synthesis of Sodium (3-(1-(6,7-dimethoxyquinazolin-4-yl)azepan-4-yl)propyl) phosphonate (I-5)

To a stirred solution of (3-(1-(6,7-dimethoxyquinazolin-4-yl)azepan-4-yl)propyl)phosphonic acid (25 mg, 0.061 mmol) in acetonitrile (0.5 mL) and water (0.5 mL) was added NaOH (4.6 mg, 0.116 mmol) at 0° C. and the reaction was stirred under lyophilisation for 16 h to afford pure sodium (3-(1-(6,7-dimethoxyquinazolin-4-yl)azepan-4-yl) propyl)phosphonate I-5 (27 mg, 0.059 mmol, 98% yield) as an off white solid.

$^1$H NMR: (400 MHz, DMSO) δ 8.118 (s, 1H), 6.945 (s, 1H), 6.854 (s, 1H), 3.917 (s, 3H), 3.801 (s, 3H), 3.705-3.774 (m, 2H), 3.474-3.570 (m, 2H), 2.001-2.026 (m, 2H), 1.783-1.871 (m, 2H), 1.440-1.513 (m, 6H), 1.297-1.325 (bs, 2H), 1.139-1.186 (m, 1H).

LCMS: $(M+H)^+$: m/Z: 410.50 $(M-2Na^+)$.

Example 3

Synthesis of Sodium ((1-(3-cyano-6,7-dimethoxy-quinolin-4-yl)azepan-4-yl)methyl)phosphonate (compound 1-7)

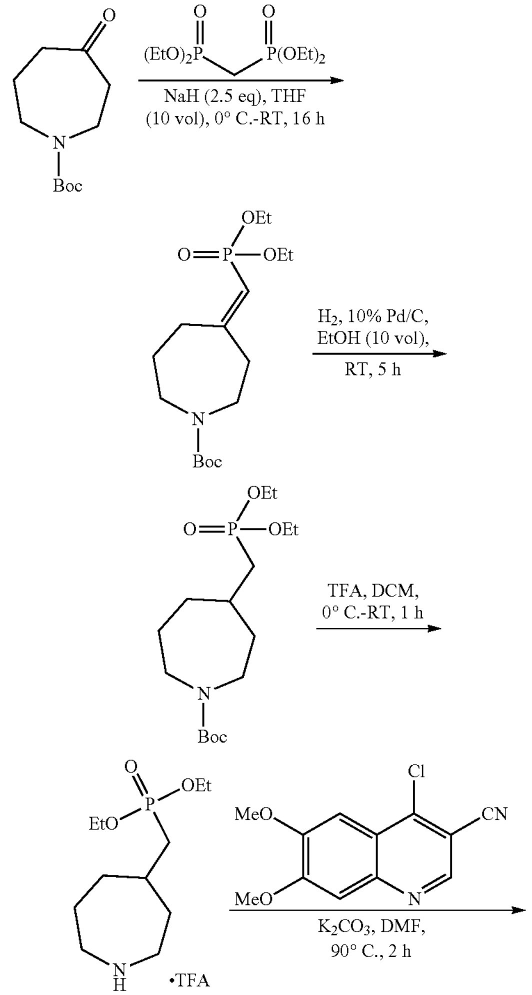

-continued

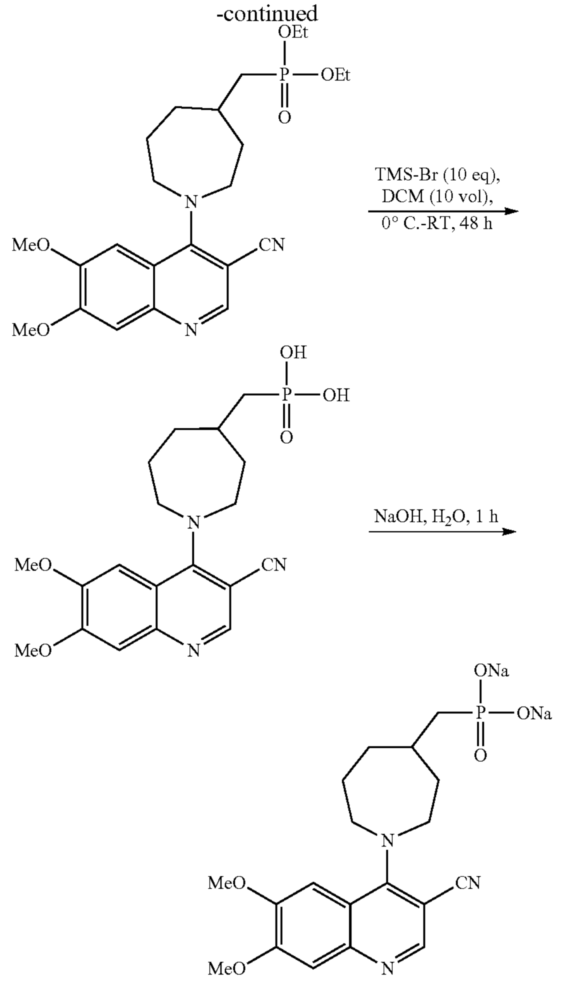

Synthesis of tert-butyl (E)-4-((diethoxy phosphoryl) methylene) azepane-1-carboxylate To a stirred solution of tetraethyl methylenebis(phosphonate) (1 g, 3.52 mmol) in toluene (10 mL) was added 60% NaH (141 mg, 5.868 mmol) at 0° C. and the mixture was stirred for 30 min, then tert-butyl 4-oxoazepane-1-carboxylate (500 mg, 2.347 mmol) was added at 0° C. in one portion. The reaction mixture was stirred at room temperature for 16 h. The progress of the reaction was monitored by TLC. After completion of the reaction, water was added (100 mL) and the mixture was extracted with ethyl acetate (2×100 mL). The combined organic phase was washed with brine (100 mL), dried over sodium sulfate and concentrated under reduced pressure to afford the crude compound of tert-butyl (E)-4-((diethoxy phosphoryl)methylene)azepane-1-carboxylate (500 mg, crude) as a pale brown gummy liquid.

$^1$H NMR: (400 MHz, DMSO) δ 5.672-5.686 (m, 1H), 4.038-4.134 (m, 4H), 3.475-3.492 (m, 4H), 2.283-2.573 (m, 4H), 1.461 (s, 9H), 1.294-1.370 (t, 3H), 0.829-0.881 (m, 2H).

Tert-butyl 4-((diethoxy phosphoryl) methyl) azepane-1-carboxylate

To a stirred solution of tert-butyl (E)-4-((diethoxy phosphoryl) methylene) azepane-1-carboxylate (500 mg, 1.441 mmol) in ethanol (10 mL) was added 10% Pd/C (70 mg) and the reaction mixture was stirred under balloon hydrogen atmosphere at room temperature for 16 h. The progress of the reaction was monitored by TLC. After completion of the reaction, the mixture was filtered through Celite and the filter bed was washed with 10% methanol in dichloromethane (50 mL). The filtrate was concentrated under reduced pressure to afford tert-butyl 4-((diethoxy phosphoryl) methyl) azepane-1-carboxylate (250 mg, 0.716 mmol, 30% yield over two steps) as a colorless oily liquid.

$^1$H NMR: (400 MHz, DMSO) δ 3.900-3.999 (m, 4H), 3.107-3.408 (m, 4H), 1.897 (s, 1H), 1.652-1.774 (m, 5H), 1.469-1.495 (m, 1H), 1.378 (s, 9H), 1.317-1.3352 (m, 1H), 1.162-1.262 (m, 7H).

Synthesis of diethyl (azepan-4-ylmethyl)phosphonate compound trifluoroacetate salt To a stirred solution of tert-butyl 4-((diethoxyphosphoryl) methyl)azepane-1-carboxylate (200 mg, 0.573 mmol) in dichloromethane (2 mL) was added trifluoroacetic acid (0.5 mL) at 0° C., and the reaction was stirred at room temperature for 3 h. The progress of the reaction was monitored by TLC. After completion of the reaction, the mixture was concentrated under reduced pressure to afford the crude compound of diethyl (azepan-4-ylmethyl)phosphonate compound trifluoroacetate salt (320 mg, crude) as a pale brown oily liquid.

$^1$H NMR: (400 MHz, DMSO) δ 8.481-8.534 (d, 2H), 3.936-4.043 (m, 4H), 3.120-3.186 (m, 2H), 2.963-3.057 (m, 2H), 1.911-2.042 (m, 3H), 1.557-1.854 (m, 5H), 0.323-1.413 (m, 1H), 1.216-1.251 (m, 6H).

Synthesis of diethyl ((1-(3-cyano-6,7-dimethoxyquinolin-4-yl)azepan-4-yl)methyl)phosphonate To a stirred solution of 4-chloro-6,7-dimethoxyquinoline-3-carbonitrile (232 mg, 0.936 mmol) in DMF (5 mL) was added potassium carbonate (452 mg, 3.278 mmol) and diethyl (azepan-4-ylmethyl)phosphonate compound trifluoroacetate salt (340 mg, 0.936 mmol) and the reaction was stirred at 90° C. for 2 h. The progress of the reaction was monitored by TLC. After completion of the reaction, water was added (100 mL) and the mixture was extracted with ethyl acetate (2×50 mL). The combined organic phase was washed with brine (50 mL), dried over sodium sulfate and concentrated under reduced pressure. The crude material was purified through combi flash chromatography to afford pure diethyl ((1-(3-cyano-6,7-dimethoxyquinolin-4-yl)azepan-4-yl)methyl)phosphonate (200 mg, 2.169 mmol, 46% yield) as a brown gummy solid.

$^1$H NMR: (400 MHz, DMSO) δ 8.626 (s, 1H), 7.369 (s, 1H), 7.325 (s, 1H), 3.940-4.006 (m, 10H), 3.55-3.3.70 (m, 4H), 1.557-2.166 (m, 9H), 1.20-1.1.25 (t, 6H).

LCMS: $(M+H)^+$: m/Z: 462.33.

Synthesis of ((1-(3-cyano-6,7-dimethoxyquinolin-4-yl)azepan-4-yl)methyl)phosphonic acid To a stirred solution of diethyl ((1-(3-cyano-6,7-dimethoxyquinolin-4-yl)azepan-4-yl)methyl)phosphonate (200 mg, 0.433 mmol) in dichloromethane (15 mL) was added TMS-Br (465 mg, 3.036 mmol) at 0° C. dropwise. The reaction mixture was stirred at room temperature for 48 h. After completion of the reaction, the mixture was concentrated under reduced pressure to afford the crude product. The crude material was washed with ether to afford ((1-(3-cyano-6,7-dimethoxyquinolin-4-yl)azepan-4-yl)methyl) phosphonic acid (70 mg, 0.173 mmol, 40% yield) as a pale brown gummy solid.

LCMS: $(M+H)^+$: m/Z: 406.0.

Synthesis of Sodium ((1-(3-cyano-6,7-dimethoxyquinolin-4-yl)azepan-4-yl)methyl) phosphonate (I-7)

To a stirred solution of ((1-(3-cyano-6,7-dimethoxyquinolin-4-yl)azepan-4-yl)methyl)phosphonic acid (70 mg, 0.173 mmol) in acetonitrile (0.5 mL) and water (0.5 mL) NaOH (14 mg, 0.35 mmol) was added and the reaction was then stirred under lyophilisation for 16 h to afford the crude compound. The crude material was purified through prep HPLC method. But during prep HPLC disodium salt dissociated into free acid ((1-(3-cyano-6,7-dimethoxyquinolin-4-yl)azepan-4-yl)methyl)phosphonic acid I-7 (20 mg, 0.044 mmol, 23% yield) as a pale yellow solid.

$^1$H NMR: (400 MHz, DMSO) δ 8.615 (s, 1H), 7.361 (s, 1H), 7.340 (s, 1H), 3.938 (s, 3H), 3.932 (s, 3H), 3.654-3.710 (t, 2H), 3.553-3.587 (t, 2H), 2.052-2.174 (m, 3H), 1.912-1.964 (m, 1H), 1.746-1.832 (m, 1H), 1.489-1.746 (m, 4H).

LCMS: $(M+H)^+$: m/Z: 406.0.

Example 4

Synthesis of ((((1-(6,7-dimethoxyquinazolin-4-yl)azepan-4-yl)methyl)phosphoryl)bis(oxy))bis(methylene) bis(2-methylpropanoate) (Compound i-10)

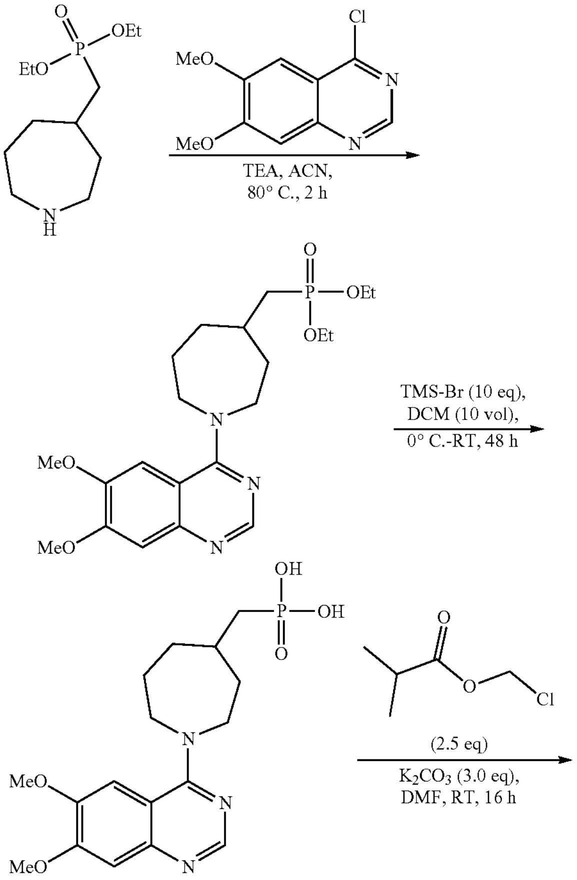

-continued

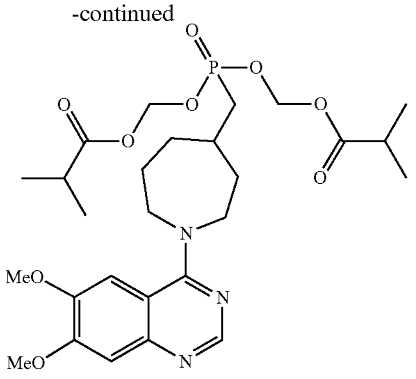

Synthesis of diethyl ((1-(6,7-dimethoxyquinazolin-4-yl)azepan-4-yl)methyl) phosphonate To a stirred solution of 4-chloro-6,7-dimethoxyquinazoline (300 mg, 1.33 mmol) in acetonitrile (3 mL) was added triethylamine (0.56 mL, 4.01 mmol) and diethyl (azepan-4-ylmethyl)phosphonate (360 mg, 1.469 mmol, prepared according to Example 3 as the freebase) and the reaction was stirred at 80° C. for 2 h. The progress of the reaction was monitored by TLC. After completion of the reaction, water was added (100 mL) and the mixture was extracted with ethyl acetate (2×50 mL). The combined organic phase was washed with brine (50 mL), dried over sodium sulfate and concentrated under reduced pressure. The crude material was purified through combi flash chromatography to afford pure diethyl ((1-(6,7-dimethoxyquinazolin-4-yl)azepan-4-yl)methyl)phosphonate (400 mg, 0.915 mmol, 68% yield) as a pale yellow solid.

LCMS: $(M+H)^+$: m/Z: 438.1.

Synthesis of ((1-(6,7-dimethoxyquinazolin-4-yl) azepan-4-yl)methyl)phosphonic acid To a stirred solution of diethyl ((1-(6,7-dimethoxyquinazolin-4-yl)azepan-4-yl)methyl)phosphonate (400 mg, 0.915 mmol) in DCM (100 vol) was added TMS-Br (1.2 mL, 10.0 eq) at −20° C. dropwise. The reaction mixture was stirred at room temperature for 48 h. After completion of the reaction was monitored by TLC, the mixture was concentrated under reduced pressure to provide the crude product. The crude material was washed with ether to afford ((1-(6,7-dimethoxyquinazolin-4-yl)azepan-4-yl)methyl)phosphonic acid (250 mg, 0.656 mmol, 71% yield) as a pale brown solid.

$^1$H NMR: (400 MHz, DMSO) δ 8.73 (s, 1H), 7.48 (s, 1H), 7.17 (s, 1H), 4.27-4.31 (m, 2H), 3.96 (s, 3H),), 3.92 (s, 3H), 3.85-3.89 (m, 2H), 2.31-2.32 (m, 1H), 2.03-2.05 (m, 1H), 2.02-1.91 (m, 3H), 2.0 (m, 2H), 2.0 (m, 2H), 1.27-1.29 (m, 1H).

LCMS: $(M+H)^+$: m/Z: 382.0.

Synthesis of ((((1-(6,7-dimethoxyquinazolin-4-yl) azepan-4-yl)methyl)phosphoryl) bis(oxy))bis(methylene) bis(2-methylpropanoate) (I-10)

To a stirred solution of ((1-(6,7-dimethoxyquinazolin-4-yl)azepan-4-yl)methyl)phosphonic acid (150 mg, 0.393 mmol) in DMF (5 mL) was added $K_2CO_3$ (190 mg, 1.37 mmol) and chloromethyl isobutyrate (240 mg, 0.979 mmol) and the reaction was stirred at RT for 16 h. The progress of the reaction was monitored by TLC. After completion of the reaction, water was added (100 mL) and the mixture was extracted with ethyl acetate (2×50 mL). The combined organic phase was washed with brine (50 mL), dried over sodium sulfate and concentrated under reduced pressure. The crude material was submitted to prep-HPLC to afford pure I-10 (30 mg, 0.051 mmol, 13% yield) as an off-white solid.

$^1$H NMR: (400 MHz, DMSO) δ 8.37 (s, 1H), 8.16 (s, 1H), 7.30 (s, 1H), 7.15 (s, 1H), 5.55-5.62 (m, 5H), 3.38-3.98 (m, 10H), 3.62-3.73 (s, 4H), 2.12-2.15 (m, 3H), 1.89-1.93 (m, 12H), 1.36-1.41 (m, 2H), 1.06-1.09 (m, 12H).

LCMS: $(M+H)^+$: m/Z: 582.0.

Example 5

ENPP1 Inhibition Assay

Materials:

Assay Buffer: 1 mM $CaCl_2$), 0.2 mM $ZnCl_2$, 50 mM Tris, pH 9.0. Substrate: 8 mM Thymidine 5'-monophosphate p-nitrophenol ester sodium salt (Sigma Cat #T4510). Enzyme: 5 ng/L Recombinant Human ENPP-1 Protein (R&D Cat #6136-EN-010) in DMSO in 96-well clear assay plates.

Methods:

An eight point serial dilution of drugs was prepared in 10× in assay buffer with the final assay concentrations starting at 10 μM, 3 μM, 1 μM, 0.3 μM and 0 μM. A dilution of DMSO was included as a control. The assay plate was set up as follows with each well in duplicate: 81 μL assay buffer+10 μL ENPP1 inhibitor or DMSO+5 μL Substrate+4 μL Enzyme. Both the enzyme and substrate was added to opposite sides of the well to ensure that there was no interaction until all wells had both components. The plate was then centrifuged gently for 10 seconds, followed by an incubation at 37° C. for 45 minutes. The reaction was quantified by measuring absorbance at 405 nm using an Envision plate reader.

$IC_{50}$ Calculation:

$IC_{50}$ values are determined using GraphPad Prism 5 software. The data were entered as an X-Y plot into the software as percent inhibition for each concentration of the drug. The concentration values of the drug were log transformed and the nonlinear regression was carried out using the "sigmoidal dose-response (variable slope)" option within the GraphPad software to model the data and calculate $IC_{50}$ values. The $IC_{50}$ values reported are the concentration of drug at which 50% inhibition was reached.

TABLE 3

Inhibition of ENPP1

| Cmpd No. | $IC_{50}$ (nM) |
|---|---|
| I-1 | ++ |
| I-2 | + |
| I-3 | ++ |
| I-4 | +++ |
| I-5 | ++ |
| I-6 | + |
| I-7 | +++ |
| — | — |
| I-8 | + |

TABLE 3-continued

| Inhibition of ENPP1 | |
|---|---|
| Cmpd No. | $IC_{50}$ (nM) |
| I-9 | +++ |
| I-10 | + |
| — | — |

+++ indicates an $IC_{50}$ value up to 10 nM
++ indicates an $IC_{50}$ value from 10 to 100 nM
+ indicates an $IC_{50}$ value greater than 100 nM.

Example 6

CndP Assay with BPNPP Substrate

Materials:

Assay Buffer: 50 mM Hepes, 150 mM NaCl, 2 mM KCl, 5 mM $MnCl_2$, pH 8.0 (Add $MnCl_2$ after setting pH). Substrate: 1 mM Bis(p-nitrophenyl) phosphate sodium salt (BPNPP) (Stock: 10 mM (10×)). Enzyme: 8 ng/μL Recombinant CndP (Stock: 2.343 mg/mL)

DMSO 96-well clear assay plates

Methods:

A ten-point serial dilution of drugs was prepared in 10× in assay buffer with the final assay concentrations starting at 100 μM, 30 μM, 10 μM, 3 μM, 1 uM, 0.3 uM, 0.1 μM, 0.03 μM, 0.01 μM and 0.003 μM. A dilution of DMSO was included as a control. The assay plate was set up as follows with each well in duplicate: 70 μL assay buffer+10 μL Enzyme (80 ng)+10 μL drug or DMSO+10 μL Substrate. The plate was then centrifuged gently for 10 seconds, followed by an incubation at 37° C. for 45 minutes. The reaction was quantified by measuring absorbance at 405 nm using an Envision plate reader. The data was analyzed using GraphPad Prism 8.0.

TABLE 4

| Inhibition of CdnP | |
|---|---|
| Cmpd No. | $IC_{50}$ (nM) |
| I-1 | ++ |
| I-2 | ++ |
| I-3 | ++ |
| I-4 | +++ |
| I-5 | ++ |
| I-6 | + |
| I-7 | +++ |
| — | — |
| I-8 | ++ |
| I-9 | ++ |
| I-10 | + |
| — | — |

+++ indicates an $IC_{50}$ value up to 100 nM
++ indicates an $IC_{50}$ value from 100 to 1,000 nM
+ indicates an $IC_{50}$ value greater than 1,000 nM.

Example 7

CdnP HPLC Assay with C-DI-AMP Substrate

Materials:

Assay Buffer: 50 mM TRIS pH 7.5, 1 mM $MnCl_2$. Substrate: 1000 μM c-di-AMP (Invivogen: tlrl-nacda). Enzyme: 20 μM Recombinant CdnP Protein (Stock: 2.343 mg/mL)

AMP (Sigma: A1752-5G)

5'-pApA sodium salt (Invivogen: tlrl-napapa)

DMSO

Stop Buffer: 0.5 M EDTA (Thermo: AM9261)

Water HPLC grade (Fisher Scientific, catalog: W5-4)

Acetonitrile HPLC grade (Fisher Scientific, catalog: A955-4)

HCOOH (Sigma Aldrich, Catalog F0507)

Method:

An eight-point serial dilution of drugs was prepared in 10× in assay buffer with the final assay concentrations starting at 10 μM, 3 μM, 1 μM, 0.3 μM, 0.1 μM, 0.03 μM, 0.01 μM and 0.003 μM. A dilution of DMSO was included as a control. The assay was set up as follows with each tube in duplicate: 14 μL assay buffer+2 μL CdnP inhibitor or DMSO+2 μL Substrate+2 μL Enzyme (2 μM). The tubes were centrifuged gently for 10 seconds, followed by an incubation at 37° C. for 120 minutes. The reaction was quenched with 2 μL EDTA and diluted with 78 μL of water. Next, 20 μL of each sample was analyzed by an Agilent 1100 series HPLC equipped with a C-18 reverse phase column (4.6×100 mm, 3.5 μm, Eclipse pulse C-18, Agilent PN: 959961-902) at room temperature. Mobile phase B (0.1% HCOOH in Water) and mobile phase C (100% Acetonitrile) solutions were degassed using an ultrasonic instrument. Flow rate of the mobile phase was 0.7 mL/min. HPLC separation was achieved using continuous gradient elution. The elution program was as follows: 0 min 100% B, 0% C; 10 min 100% B, 0% C; 20 min 95% B, 5% C; 25 min 90% B, 10% C; 30 min 50% B, 50% C; 35 min 50% B, 10% C and 37 min 100% B, 0% C. Peaks were detected at 254 nm and the peak area was calculated using Agilent ChemStation 1100 HPLC software equipped with the instrument. AMP, c-di-AMP and pApA in the samples were identified by comparison with retention time of standards. AMP standard curve was made to check the linear response of the HPLC method. Eight dilutions of AMP (500, 200, 100, 50, 20, 10, 5 and 2 μM) was prepared in water from stock solutions. 20 μL of each sample was injected in HPLC and peak area was calculated to prepare the standard curve of AMP peak area vs concentration. The standard curve exhibited a perfectly linear response. AMP peak area in the control reaction (reaction with substrate and enzyme only; no drug) was considered as 100% enzymatic activity. Percent inhibition in the presence of drug was determined by calculating AMP peak area in that reaction and comparing with the control reaction. Results for representative compounds are shown below in Table 5.

TABLE 5

| Inhibition percentage of CdnP | | | |
|---|---|---|---|
| Compound | 100 μM | 10 μM | 1 μM |
| I-1 | +++ | +++ | + |
| II-1 | +++ | | |

+++ indicates greater than 50% inhibition
++ indicates between 20-50% inhibition
+ indicates up to 20% inhibiton Example 8

Pharmaceutical Composition Examples

“Active ingredient” as used throughout these examples relates to one or more of the compounds of the present disclosure, or a pharmaceutically acceptable salt, solvate, polymorph, hydrate and the stereochemically isomeric form thereof, or pharmaceutical composition derived therefrom.

Typical examples of recipes for the formulations are as given below. Various other dosage forms can be applied herein such as a filled gelatin capsule, liquid emulsion/suspension, ointments, suppositories or chewable tablet form employing the disclosed compounds in desired dosage amounts in accordance with the present disclosure. Various conventional techniques for preparing suitable dosage forms can be used to prepare the pharmaceutical compositions, such as those disclosed herein and in standard reference texts, for example the British and US Pharmacopoeias, Remington's Pharmaceutical Sciences (Mack Publishing Co.) and Martindale The Extra Pharmacopoeia (London The Pharmaceutical Press). The disclosure of this reference is hereby incorporated herein by reference.

a. Pharmaceutical Composition for Oral Administration

A table can be prepared as follows:

| Component | Amount |
| --- | --- |
| Active ingredient | 10 to 500 mg |
| Lactose | 100 mg |
| Crystalline cellulose | 60 mg |
| Magnesium stearate | 5 mg |
| Starch (e.g., potato starch | Amount necessary to yield total weight below |
| Total per tablet | 1000 mg |

Alternatively, about 100 mg of a disclosed compound, 50 mg of lactose (monohydrate), 50 mg of maize starch (native), 10 mg of polyvinylpyrrolidone (PVP 25) (e.g., from BASF, Ludwigshafen, Germany) and 2 mg of magnesium stearate are used per tablet. The mixture of active component, lactose and starch is granulated with a 5% solution (m/m) of the PVP in water. After drying, the granules are mixed with magnesium stearate for 5 min. This mixture is moulded using a customary tablet press (e.g., tablet format: diameter 8 mm, curvature radius 12 mm). The moulding force applied is typically about 15 kN.

Alternatively, a disclosed compound can be administered in a suspension formulated for oral use. For example, about 100-5000 mg of the desired disclosed compound, 1000 mg of ethanol (96%), 400 mg of xanthan gum, and 99 g of water are combined with stirring. A single dose of about 10-500 mg of the desired disclosed compound according can be provided by 10 mL of oral suspension.

In these Examples, active ingredient can be replaced with the same amount of any of the compounds according to the present disclosure, in particular by the same amount of any of the exemplified compounds. In some circumstances it may be desirable to use a capsule, e.g., a filled gelatin capsule, instead of a tablet form. The choice of tablet or capsule will depend, in part, upon physicochemical characteristics of the particular disclosed compound used.

Examples of alternative useful carriers for making oral preparations are lactose, sucrose, starch, talc, magnesium stearate, crystalline cellulose, methyl cellulose, hydroxypropyl cellulose, hydroxypropylmethyl cellulose, carboxymethyl cellulose, glycerin, sodium alginate, gum arabic, etc. These alternative carriers can be substituted for those given above as required for desired dissolution, absorption, and manufacturing characteristics.

The amount of a disclosed compound per tablet for use in a pharmaceutical composition for human use is determined from both toxicological and pharmacokinetic data obtained in suitable animal models, e.g., rat and at least one non-rodent species, and adjusted based upon human clinical trial data. For example, it could be appropriate that a disclosed compound is present at a level of about 10 to 1000 mg per tablet dosage unit.

b. Pharmaceutical Composition for Injectable Use

A parenteral composition can be prepared as follows:

| Component | Amount |
| --- | --- |
| Active ingredient | 10 to 500 mg |
| Sodium carbonate | 560 mg* |
| Sodium hydroxide | 80 mg* |
| Distilled sterile water | Quantity sufficient to prepare the total volume indicated below |
| Total | 10 mL per sample |

*Amount adjusted as required to maintain physiological pH in the context of the amount of active ingredient, and form of active ingredient, e.g., a particular salt form of the active ingredient.

Alternatively, a pharmaceutical composition for intravenous injection can be used, with composition comprising about 100-5000 mg of a disclosed compound, 15 g polyethylenglycol 400 and 250 g water in saline with optionally up to about 15% Cremophor EL, and optionally up to 15% ethyl alcohol, and optionally up to 2 equivalents of a pharmaceutically suitable acid such as citric acid or hydrochloric acid are used. The preparation of such an injectable composition can be accomplished as follows: The disclosed compound and the polyethylenglycol 400 are dissolved in the water with stirring. The solution is sterile filtered (pore size 0.22 m) and filled into heat sterilized infusion bottles under aseptic conditions. The infusion bottles are sealed with rubber seals.

In a further example, a pharmaceutical composition for intravenous injection can be used, with composition comprising about 10-500 mg of a disclosed compound, standard saline solution, optionally with up to 15% by weight of Cremophor EL, and optionally up to 15% by weight of ethyl alcohol, and optionally up to 2 equivalents of a pharmaceutically suitable acid such as citric acid or hydrochloric acid. Preparation can be accomplished as follows: a desired disclosed compound is dissolved in the saline solution with stirring. Optionally Cremophor EL, ethyl alcohol or acid are added. The solution is sterile filtered (pore size 0.22 m) and filled into heat sterilized infusion bottles under aseptic conditions. The infusion bottles are sealed with rubber seals.

In this Example, active ingredient can be replaced with the same amount of any of the compounds according to the present disclosure, in particular by the same amount of any of the exemplified compounds.

The amount of a disclosed compound per ampule for use in a pharmaceutical composition for human use is determined from both toxicological and pharmacokinetic data obtained in suitable animal models, e.g., rat and at least one non-rodent species, and adjusted based upon human clinical trial data. For example, it could be appropriate that a disclosed compound is present at a level of about 10 to 1000 mg per tablet dosage unit.

Carriers suitable for parenteral preparations are, for example, water, physiological saline solution, etc. which can be used with tris(hydroxymethyl)aminomethane, sodium carbonate, sodium hydroxide or the like serving as a solubilizer or pH adjusting agent. The parenteral preparations contain preferably 50 to 1000 mg of a disclosed compound per dosage unit.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

U.S. Provisional Application 63/123,287, filed Dec. 9, 2020 and U.S. Provisional Application 63/123,304, filed Dec. 9, 2020, are incorporated herein by reference, in their entirety.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A compound having the following Structure (I):

(I)

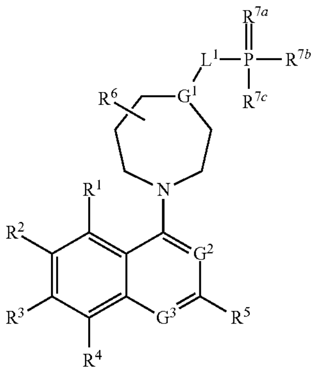

or a stereoisomer, tautomer, or pharmaceutically acceptable salt thereof, wherein:

$G^1$ is N or CH;

$G^2$ is N or $CR^9$;

$G^3$ is N or $CR^{10}$;

$L^1$ is a direct bond, $C_1$-$C_6$ alkylene, or $C_1$-$C_6$ aminylalkylene, provided that $L^1$ is a direct bond only if $G^1$ is CH;

$R^1$, $R^2$, $R^3$, $R^4$, $R^5$, $R^9$ and $R^{10}$ are each independently hydrogen, alkyl, halo, hydroxy, cyano, haloalkyl, alkoxy, haloalkoxy, hydroxyalkyl, aminylcarbonylalkyl, aminylalkyl, aminylcarbonyl, aminyl, alkylcarbonyl, —C(═O)Oalkyl, heterocyclyl, or heteroaryl;

$R^6$ is hydrogen, alkyl, halo, hydroxy, cyano, haloalkyl, alkoxy, haloalkoxy, or hydroxyalkyl;

$R^{7a}$ is O or S;

$R^{7b}$ and $R^{7c}$ are each independently —$O^-$, —OH, —$S^-$, —SH, or —$NR^{8a}R^{8b}$, and $R^{8a}$ and $R^{8b}$ are, at each occurrence, independently hydrogen or alkyl.

2. The compound of claim 1, wherein $R^1$, $R^2$, $R^3$, $R^4$, and $R^5$ are each independently hydrogen, halogen, hydroxy, alkoxy, aminylcarbonyl, aminyl, —C(═O)Oalkyl, or a 5-6 membered heteroaryl.

3. The compound of claim 1, having one of the following structures:

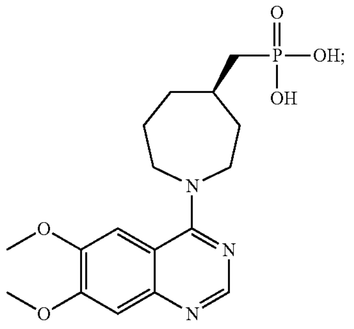

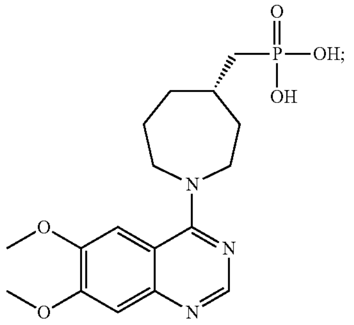

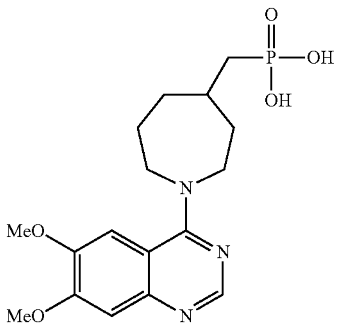

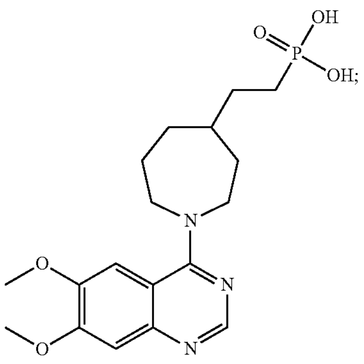

-continued
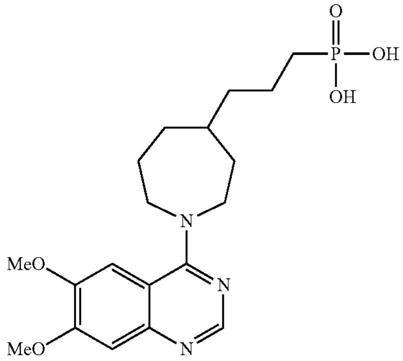
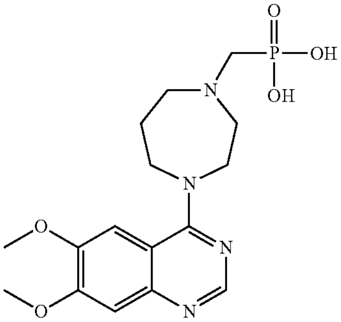
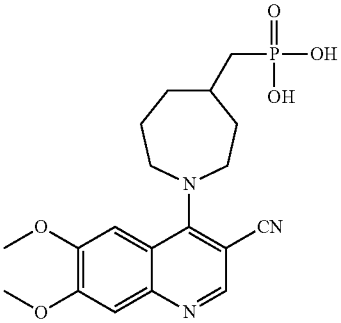
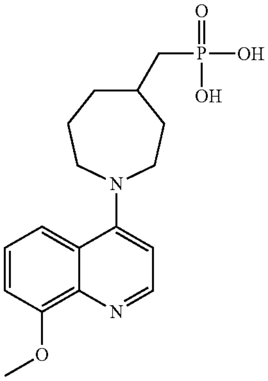
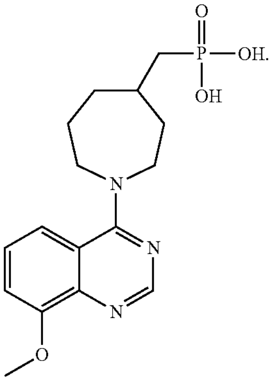
4. The compound, having one of the following structures:
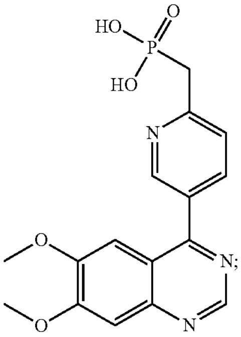
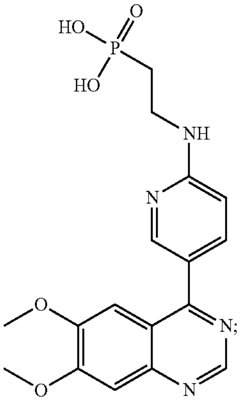
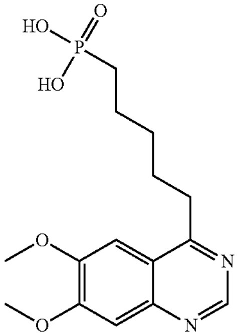
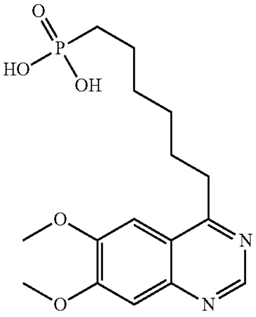
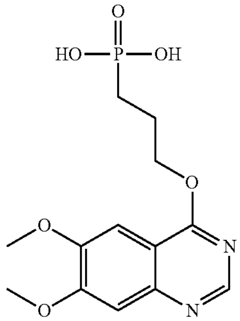
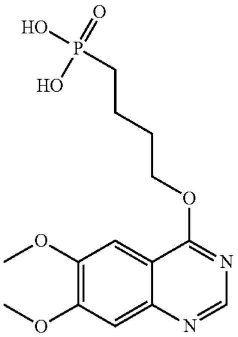
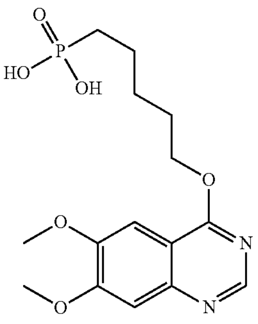
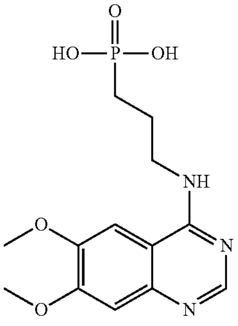

-continued
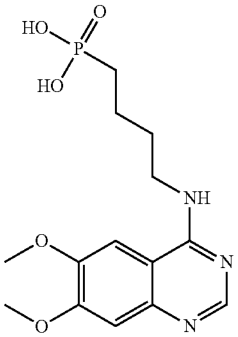
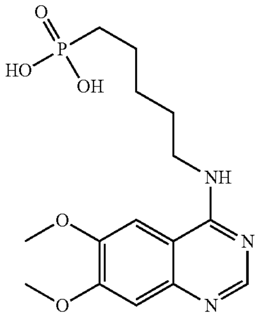
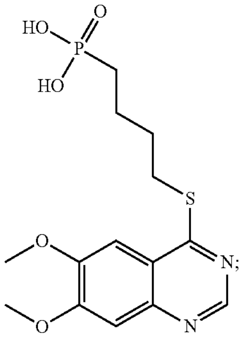
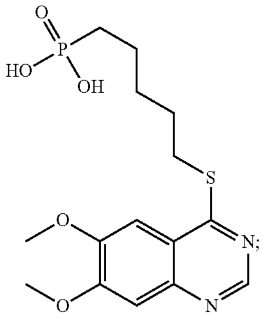
-continued
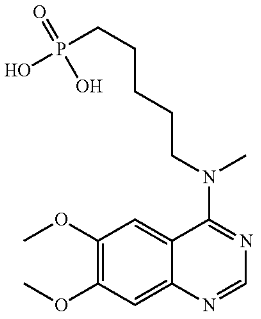
or
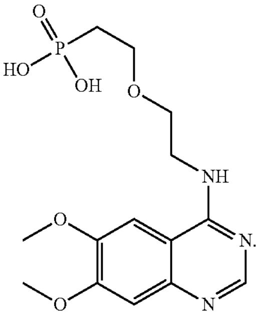
5. A pharmaceutical composition comprising a compound of claim 1 and a pharmaceutically acceptable carrier, diluent, or excipient.
6. A pharmaceutical composition comprising a compound of claim 4 and a pharmaceutically acceptable carrier, diluent, or excipient.
* * * * *